US011591376B2

(12) United States Patent
Gasch et al.

(10) Patent No.: US 11,591,376 B2
(45) Date of Patent: Feb. 28, 2023

(54) OVER-EXPRESSION OF AZF1 IMPROVES THE RATE OF ANAEROBIC XYLOSE FERMENTATION IN ENGINEERED YEAST STRAINS

(71) Applicant: Wisconsin Alumni Research Foundation, Madison, WI (US)

(72) Inventors: Audrey P. Gasch, Madison, WI (US); Kevin Myers, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 44 days.

(21) Appl. No.: 16/156,463

(22) Filed: Oct. 10, 2018

(65) Prior Publication Data
US 2019/0106469 A1 Apr. 11, 2019

Related U.S. Application Data

(60) Provisional application No. 62/570,851, filed on Oct. 11, 2017.

(51) Int. Cl.
| | | |
|---|---|---|
| *C07K 14/47* | (2006.01) | |
| *C12P 7/06* | (2006.01) | |
| *C07K 14/395* | (2006.01) | |
| *C12P 7/10* | (2006.01) | |

(52) U.S. Cl.
CPC .......... *C07K 14/47* (2013.01); *C07K 14/395* (2013.01); *C12P 7/06* (2013.01); *C12P 7/10* (2013.01)

(58) Field of Classification Search
CPC ....... C12N 15/09; C12N 15/8216; C12P 7/06; C12P 7/10
See application file for complete search history.

(56) References Cited

U.S. PATENT DOCUMENTS

| | | | | |
|---|---|---|---|---|
| 5,900,362 | A * | 5/1999 | Eberz ................ | C12Q 1/66 435/37 |
| 6,127,600 | A * | 10/2000 | Beach ............... | C12N 15/8251 435/320.1 |
| 2005/0251879 | A1 * | 11/2005 | Hofius .............. | C12N 15/8283 800/280 |
| 2006/0263864 | A1 * | 11/2006 | Busby .............. | C12P 17/06 435/125 |
| 2010/0050292 | A1 * | 2/2010 | Launhardt ........ | C12N 9/1051 800/278 |
| 2010/0285993 | A1 * | 11/2010 | Prelich ............. | C12N 15/1093 506/14 |
| 2014/0244228 | A1 * | 8/2014 | Lee .................. | G16B 30/00 703/11 |
| 2016/0130590 | A1 * | 5/2016 | Chen ................ | C12P 7/16 435/471 |

OTHER PUBLICATIONS

Brohl et al. (1994) A New Nuclear Suppressor System for a Mitochondrial RNA Polymerase Mutant Identifies an Unusual Zinc-Finger Protein and a Polyglutamine Domain Protein in *Saccharomyces cerevisiae*Yeast, vol. 10, pp. 1-13.*
Reference (2020) AZF1 Azf1p [ *Saccharomyces cerevisiae* S288C ], pp. 1-5.*
Mirzaei et al. (2013) Systematic measurement of transcription factor-DNA interactions by targeted mass spectrometry identifies candidate gene regulatory proteins, Proc. Natl. Acad. Sci, vol. 110, No. 9, pp. 3645-3650.*
Peytavi et al. (2005) Correlation between microarray DNA hybridization efficiency and the position of short capture probe on the target nucleic acid, BioTechique, vol. 39. No.1, pp. 89-96.*
Hill et al. (1986) Yeast/*E. coli* Shuttle Vectors with Multiple Unique Restriction Sites, Yeast, vol. 2, pp. 163-167.*
Ho et al. (2009) A molecular barcoded yeast ORF library enables mode-of-action analysis of bioactive compounds, Nat Biotechnol. vol. 27, No. 4, pp. 1-19.*
Cromie et al. (Aug. 2017) Transcriptional Profiling of Biofilm Regulators Identified by an Overexpression Screen in *Saccharomyces cerevisiae*, Genes Genomes & Genetics, vol. 7, pp. 2845-2854.*
Magtanong LJ. (2011) A Novel Gene Overexpression Plasmid Library and its application in Mapping Genetic Networks by Systematic Dosage Suppression, A thesis for Ph.D degree, Depart. Mol. Genetics (2011) University of Toronto, pp. 1-136.*
Newcomb et al. (2002) AZF1 Is a Glucose-Dependent Positive Regulator of CLN3 Transcription in *Saccharomyces cerevisiae*, Mol. Cell. Biol., vol. 22, No. 5, pp. 1607-1614.*
Sun et al. (2021) "Xylose Assimilation for the Efficient Production of Biofuels and Chemicals by Engineered *Saccharomyces cerevisiae*, " Biotechnol. J., 16, 2000142, pp. 1-11.*
Myers et al. (2019) Rewired cellular signaling coordinates sugar and hypoxic responses for anaerobic xylose fermentation in yeast, PLOS Genetics, vol. 15, No. 3, e1008037, pp. 1-33.*
Slattery et al. (2006) The Function and Properties of the Azf1 Transcriptional Regulator Change with Growth Conditions in *Saccharomyces cerevisiae*, Eukary. Cell, vol. 5, No. 2, pp. 313-320.*
Kim, Soo Rin, et al., "High expressicn cf XYL2ceding fcr xylitcl dehydrogenase is necessary fcr efficient xylcse fermentaticn by engineered *Saccharomyces cerevisiae*", Metabolic Engineering, 14(4), (2012), 336-343.
Kuyper, Marko, et al., "Metabolic engineering of a xylose-isomerase-expressing *Saccharomyces cerevisiae* strain for rapid anaerobic xylose fermentation", *FEMS Yeast Research*, 5, (2005), 399-409.

(Continued)

*Primary Examiner* — Iqbal H Chowdhury
(74) *Attorney, Agent, or Firm* — Schwegman Lundberg & Woessner, P.A.

(57) ABSTRACT

The present invention provides an isolated AZF1 gene sequence, recombinant vectors, and recombinant yeast which are useful in methods of enhanced biofuel production, particularly ethanol production. Methods of bioengineering recombinant yeast with isolated AZF1 gene sequence useful for biofuel production are also provided.

12 Claims, 22 Drawing Sheets
Specification includes a Sequence Listing.

(56) References Cited

OTHER PUBLICATIONS

Parachin, Nádia S., et al., "Kinetic modelling reveals current limitations in the production of ethanol from xylose by recombinant *Saccharomyces cerevisiae*", *Metabolic Engineering*, 13(5), (2011), 508-517.

Zhou, Hang, et al., "Xylose isomerase overexpression along with engineering of the pentose phosphate pathway and evolutionary engineering enable rapid xylose utilization and ethanol production by *Saccharomyces cerevisiae*", *Metabolic Engineering*, 14(6), (Nov. 2012), 611-622.

\* cited by examiner

SEQUENCE LISTING

<160> NUMBER OF SEQ ID NOS: 2

<210> SEQ ID NO 1
<211> LENGTH: 2745
<212> TYPE: DNA
<213> ORGANISM: Saccharomyces cerevisiae

<400> SEQUENCE: 1

```
atgcctcctc caactgcaca gttcatgggc cctacgcagg cgggacaaaa tgaaagccaa      60
aatcaatcat caggcgaagc tggggagcaa aaccaggagc atgggcaagg ccctactcct     120
attcttaatc aaagtcaacc ggcttcttct caaccgcaac atcaacaaca aaggaatgag     180
tcgatttcat attatacaaa tttcaaccag ccacgatatt ccacggacgc ctctatcaac     240
tcattcttga acatatctga taacgtacca gtaacaagta caggaggacc tagttctggc     300
ggcgcctatt ccaatcttcc acgattatcc acttcaagta cacatcaacc gccagacctg     360
tcgcaaatcg gacgcggctt ttccattgta aacaacctct tcccacaaca acagcagctt     420
caaaatcagc atcggcaaca gcagcaacaa caacaacagc agtcgcacca gcagcctccc     480
ttcaagaccc cttcattttc gacgggatta acgggaagtt cttctcaata tcaattttta     540
ccaagaaatg ataatacttc gcagccacct tcaaaaagaa actctgttta tcttggacct     600
aatgatgggc ctgattttga atttttcagt atgcagcagt cacagcaacc gcagttccag     660
cctagcagta gaagagaatc aaactctatg agacctccac tgttaatacc tgcagcaact     720
actaaaagcc agtccaatgg caccaataat agtgggaata tgaacacaaa tgcagattat     780
gaatcatttt ttaatactgg tacaaacaac agtaattcta atcagaaccc gtacttttg      840 agttcaagaa ataattcttt gaagtttaat cctgaagatt tcgattttca attcaaaagg     900
cggaattctt tgttagagg tactttggac catagcagcc aaaatgcgtt tatacctgaa      960
tcaagattaa actcactatc cgttaacaac aaagctaatg tgatcctgt cgcggataat     1020 gttaccaata acatgaaagg aaaaagtaat gaagttgaca atgatgatgg caatgacagt    1080
agcaataaca ataacaacaa caacaacaac aacaacaatg aaaacaacaa tgacaacaat    1140
aatgataata acgacaatag tattaattcc gccaccagta ctaatatccc aaaccaagag    1200
gaccatagcc ttgcttctac cgataccaca agcaatagta ggaaagatct aaaagaaata    1260
gaacaaagac ttcgaaaaca tttgaatgat gaggataatt actctagtgc tatatcaaga    1320
ccattggata aaaacgacgt aattgaaggc agtgagggat tgaacaaaca tatagacgag    1380
```

```
tctggtatgc aacctaatat tatcaagaaa aggaaaaagg atgattctac tgtgtacgtc    1440
aagaatgaga tgccccgtac tgatccccg atgagtaaag acaattctac ttctgctgaa    1500
ggagcagcaa tggcaaactt ttctggtaaa gaacctccta tacctgacat aagttcagta    1560
agtgatgatg ctactaacct gataggtgca acaaaggtcg accaactaat gttgattatt    1620
caagcaagaa agaaaggttt cacggagaaa gtaaatacca ctcaagatgg agacttactg    1680
tttaaccaaa cgatggacat tttaccacct aaaagcgaac tagtaggtgg tgtggagaaa    1740
ccaaaaggca cacaaaatac acgagcagtt aaaaacatg aatgtcccta ttgtcatcgg    1800
cttttttcgc aagcgactca tctggaggtt cacgttcgtt ctcataggg gtacaaacca    1860 ttcgtttgtg attattgtgg caaacgtttt actcagggtg ggaacttaag aactcatgaa    1920
cgactacaca caggtgaaaa accgtattca tgtgatattt gtgataaaaa attttctagg    1980
aaagggaact tagctgctca cttggttact caccaaaaat tgaaaccatt tgtttgcaag    2040
cttgaaaact gcaacaagac cttcactcaa ctaggaaata tgaaggccca tcaaaataga    2100
tttcataagg aaacattaaa tgccttaacg gcaaaattag ctgagatgaa tccatctgag    2160
aatattccac ttgaagagcg gcaacttttg gagtactttg cgtccattta taaaaattca    2220
aacaggggaa ttaaaggtag aggaaaaggt gtaggaacca aaaaatcaac aatttcctca    2280
ccagaaaacc atcctgcgag cacaattttg aatccaaata caaatgcaaa taatgctatt    2340
gctaatgatt ctgaaaataa cggcaacccct gaaggtaaca ttgacagcag tagtaacagc    2400
aatccgggct cacatagtat gatttcgccg acgcaaaaag acatgggtac gttgcaatca    2460
caatttatcc aaaataattt taacaattct gtgaacagtt cgaatccgtc caaccaacca    2520
atcataaact acaattacac cacacttcct cattctagat taggaagtag tagttccagc    2580
aataccaaca ataataacag caacttttcg gtaggtgcag ctccgggtgt attaatggcg    2640
ccaaccacca ataatgactt cagtttcaac ttggatcaat ctaatgataa tgaaagatct    2700
caacaagaac aagtgagatt taagaacatt aattacaaaa gctag               2745
```

<210> SEQ ID NO 2
<211> LENGTH: 3906
<212> TYPE: DNA
<213> ORGANISM: Artificial Sequence
<220> FEATURE:
<223> OTHER INFORMATION: AZF1 gene and flanking sequence in the MoBY
      2.01 plasmid

<400> SEQUENCE: 2

```
atagtactgc agattcggaa gatgtgaaag atattgattt tgagaattac ggttgtgatg      60
aagaggatat gaataaagaa gacaatttgt tagccgcaca attttttaaat aatttacgtt     120 taaattctcc ctcagcaaca acaccaagta acattaccga gagcgaaatt gattccgccc     180
aggatggaag tggatgggac gacctcagcg ataccgatgg ctttattaca aatggtacca     240
cagaatcctt cgatgaaaca acaaaccctg taacaaccgc aagcaccccca aaattattcg     300 gaaaacctat taaattaat aaaagttgga atgatgagtt gaatgatgat ggctggattc      360
aagatgaaag cggcccatca aaggtgcctc aaaaacacac aaggccacaa aattcaacgt     420
tggcaaaatc catcgctcct agctcaaggc tttctatcaa gaagaagaaa acaacgatcc     480
tagcaccaag aaacattgct agtaactcta ctgttaccac caaatcgtca ctgtccaata     540
aaactgcaag aagtaagcct ataagtagta tccgcggctc ggtaaccaag aaaggaaatg     600
ttgacggctg ggatgatgat ggggattcag actcctggga tacgaattgg tgatcccaag     660
```

```
acttatatag ccctacgtat tgtagaagga tatattcagt gttaatcgtt atttagaaac    720
attacgcccg tgccccgcga tttcgcttct ttgagaagtg gaggaaaaga agggtccctt    780
taattccagt agaaatgaag cataagcaag aagagtcatc agaaaaggga accttgtagt    840
actatagatg gtcccacaga gaaattaatt gggacaaaaa cagctacaca agcgatatac    900
ttcaaaagat tcagatattg aaaaattacc agccatgcct cctccaactg cacagttcat    960
gggccctacg caggcgggac aaaatgaaag ccaaaatcaa tcatcaggcg aagctgggga   1020
gcaaaaccag gagcatgggc aaggccctac tcctattctt aatcaaagtc aaccggcttc   1080
ttctcaaccg caacatcaac aacaaaggaa tgagtcgatt tcatattata caaatttcaa   1140
ccagccacga tattccacgg acgcctctat caactcattc ttgaacatat ctgataacgt   1200
accagtaaca agtacaggag gacctagttc tggcggcgcc tattccaatc ttccacgatt   1260
atccacttca agtacacatc aaccgccaga cctgtcgcaa atcggacgcg cttttccat    1320 tgtaaacaac ctcttcccac aacaacagca gcttcaaaat cagcatcggc aacagcagca   1380
acaacaacaa cagcagtcgc accagcagcc tcccttcaag accccttcat tttcgacggg   1440
attaacggga agttcttctc aatatcaatt tttaccaaga aatgataata cttcgcagcc   1500
accttcaaaa agaaactctg tttatcttgg acctaatgat gggcctgatt ttgaattttt   1560
cagtatgcag cagtcacagc aaccgcagtt ccagcctagc agtagaagag aatcaaactc   1620
tatgagacct ccactgttaa tacctgcagc aactactaaa agccagtcca atggcaccaa   1680
taatagtggg aatatgaaca caaatgcaga ttatgaatca tttttaata ctggtacaaa    1740 caacagtaat tctaatcaga acccgtactt tttgagttca agaaataatt ctttgaagtt   1800
taatcctgaa gatttcgatt ttcaattcaa aaggcggaat tcttttgtta gaggtacttt   1860
ggaccatagc agccaaaatg cgtttatacc tgaatcaaga ttaaactcac tatccgttaa   1920
caacaaagct aatggtgatc ctgtcgcgga taatgttacc aataacatga aggaaaaag    1980 taatgaagtt gacaatgatg atggcaatga cagtagcaat aacaataaca acaacaacaa   2040
caacaacaac aatgaaaaca acaatgacaa caataatgat aataacgaca atagtattaa   2100
ttccgccacc agtactaata tcccaaacca agaggaccat agccttgctt ctaccgatac   2160
cacaagcaat agtaggaaag atctaaaaga aatagaacaa agacttcgaa acatttgaa    2220 tgatgaggat aattactcta gtgctatatc aagaccattg gataaaaacg acgtaattga   2280
aggcagtgag ggattgaaca acatatataga cgagtctggt atgcaaccta atattatcaa   2340
gaaaaggaaa aaggatgatt ctactgtgta cgtcaagaat gagatgcccc gtactgatcc   2400
cccgatgagt aaagacaatt ctacttctgc tgaaggagca gcaatggcaa acttttctgg   2460
taaagaacct cctatacctg acataagttc agtaagtgat gatgctacta acctgatagg   2520
tgcaacaaag gtcgaccaac taatgttgat tattcaagca agaaagaaag gtttcacgga   2580
gaaagtaaat accactcaag atggagactt actgtttaac caaacgatgg acattttacc   2640
acctaaaagc gaactagtag gtggtgtgga gaaaccaaaa ggcacacaaa atacacgagc   2700
agttaaaaaa catgaatgtc cctattgtca tcggcttttt tcgcaagcga ctcatctgga   2760
ggttcacgtt cgttctcata tagggtacaa accattcgtt tgtgattatt gtggcaaacg   2820
ttttactcag ggtgggaact aagaactca tgaacgacta cacacaggtg aaaaaccgta    2880
ttcatgtgat atttgtgata aaaaatttc taggaaaggg aacttagctg ctcacttggt   2940
tactcaccaa aaattgaaac catttgtttg caagcttgaa aactgcaaca agaccttcac   3000
```

```
tcaactagga aatatgaagg cccatcaaaa tagatttcat aaggaaacat taaatgcctt    3060
aacggcaaaa ttagctgaga tgaatccatc tgagaatatt ccacttgaag agcggcaact    3120
tttggagtac tttgcgtcca tttataaaaa ttcaaacagg ggaattaaag gtagaggaaa    3180
aggtgtagga accaaaaaat caacaatttc ctcaccagaa aaccatcctg cgagcacaat    3240
tttgaatcca aatacaaatg caaataatgc tattgctaat gattctgaaa ataacggcaa    3300
ccctgaaggt aacattgaca gcagtagtaa cagcaatccg ggctcacata gtatgatttc    3360
gccgacgcaa aaagacatgg gtacgttgca atcacaattt atccaaaata attttaacaa    3420
ttctgtgaac agttcgaatc cgtccaacca accaatcata aactacaatt acaccacact    3480
tcctcattct agattaggaa gtagtagttc cagcaatacc aacaataata acagcaactt    3540
ttcggtaggt gcagctccgg gtgtattaat ggcgccaacc accaataatg acttcagttt    3600
caacttggat caatctaatg ataatgaaag atctcaacaa gaacaagtga gatttaagaa    3660
cattaattac aaaagctagc aggcttaga ggcactacct ttttttttt ttcgagtttc     3720 tacaccgtag tatctgattt catagtggta ttcgtcaaac ttaacccaca agtgtcactt    3780
ttcctttctt tttttctttt tcttgaagaa ctgcatggtt ttctagctct ttttcacttt    3840
tttgaggttt tatttatctt gtattctttt tttctattat tttaaaggtt caatttctat    3900
cgacgg                                                              3906
```

OVER-EXPRESSION OF AZF1 IMPROVES THE RATE OF ANAEROBIC XYLOSE FERMENTATION IN ENGINEERED YEAST STRAINS

CROSS-REFERENCE TO RELATED APPLICATIONS

This application claims the benefit of U.S. provisional application 62/570,851, filed Oct. 11, 2017, hereby incorporated by reference.

STATEMENT AS TO RIGHTS TO INVENTIONS MADE UNDER FEDERALLY SPONSORED RESEARCH AND DEVELOPMENT

This invention was made with government support under DE-FC02-07ER64494 awarded by the U.S. Department of Energy. The government has certain rights in the invention.

FIELD OF THE INVENTION

The present invention relates to the production of biofuel. More particularly, the present invention relates to a yeast gene involved in anaerobic xylose fermentation and methods of using same for enhanced biofuel production.

BACKGROUND OF THE INVENTION

In view of the current state of the biofuel industry, particularly ethanol production based on xylose-containing feedstocks, it can be appreciated that identifying genes related to enhanced biofuel production is a substantial challenge in the field. Accordingly, a need exists in the field to identify additional genes that influence biofuel production in yeast, and, consequently, engineered recombinant strains of yeast capable of increased biofuel yields from commonly-available feedstocks, including xylose-containing feedstocks.

SUMMARY OF THE INVENTION

Based on the inventors' substantial efforts to improve the rate of xylose conversion to ethanol, the present invention provides, in a first aspect, an isolated nucleic acid having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in yeast of the isolated nucleic acid provides increased rate of anaerobic xylose fermentation in the yeast relative to a control yeast lacking over-expression of the isolated nucleic acid.

In certain embodiments, the isolated nucleic acid is contained in a recombinant vector. Certain recombinant vectors include a heterologous promoter operably linked to the isolated nucleic acid, preferably an inducible type heterologous promoter.

In another aspect, the invention is a recombinant vector including an isolated nucleic acid having (a) a nucleotide sequence of SEQ ID NO:1 or (b) a nucleotide sequence which hybridizes under stringent conditions to SEQ ID NO:1, or to a fully complementary nucleotide sequence thereof; and a heterologous sequence for extrachromosomal stable maintenance and/or to drive over-expression of the isolated nucleic acid.

In yet another aspect, the invention is directed to a recombinant yeast engineered to contain one or more of the isolated nucleic acids having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid.

In certain embodiments of the recombinant yeast, the isolated nucleic acid is a portion of an extrachromosomal vector stably maintained in the recombinant yeast. Alternatively, the isolated nucleic acid is integrated into a chromosome of the recombinant yeast.

In yet another aspect, the invention encompasses a yeast inoculum, formulated to contain: (a) a recombinant yeast as described and claimed herein; and (b) a culture medium.

The invention further provides a method for producing ethanol by anaerobic fermentation of xylose in yeast. Such a method includes steps of: (a) culturing under ethanol-producing conditions a recombinant yeast engineered to contain one or more of the isolated nucleic acids having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid; and isolating ethanol produced by the recombinant yeast.

For such methods of biofuel production, the recombinant yeast is preferably of the genus *Saccharomyces*, more preferably of the species *Saccharomyces cerevisiae*.

In another aspect, the invention facilitates production of a recombinant yeast useful in biofuel production. Such a method includes steps of introducing into an isolated yeast an isolated nucleic acid having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid.

In yet another aspect, the invention provides a method for producing ethanol by anaerobic fermentation of xylose in yeast, including steps of (a) culturing under ethanol-producing conditions a recombinant yeast comprising an isolated nucleic acid encoding AZF1 or a nucleotide sequence which hybridizes under stringent conditions to the isolated nucleic acid encoding AZF1, or to a fully complementary nucleotide sequence thereof, and (b) isolating ethanol produced by the recombinant yeast.

As can be appreciated, the present invention contemplates the use of recombinant yeast as described and claimed herein in the production of biofuel, including certain exemplary recombinant *S. cerevisiae* strains specifically identified in this disclosure.

This invention provides the advantage over prior biofuel-producing technologies in that embodiments of the invention utilize or are based on a robust recombinant DNA approach that provides yeast strains with appreciably increased rate of anaerobic xylose fermentation capabilities. Other objects, features and advantages of the present invention will become apparent after review of the specification, claims and drawings. The detailed description and examples enhance the understanding of the invention, but are not intended to limit the scope of the appended claims.

DETAILED DESCRIPTION OF THE INVENTION

I. In General

Figure 1:
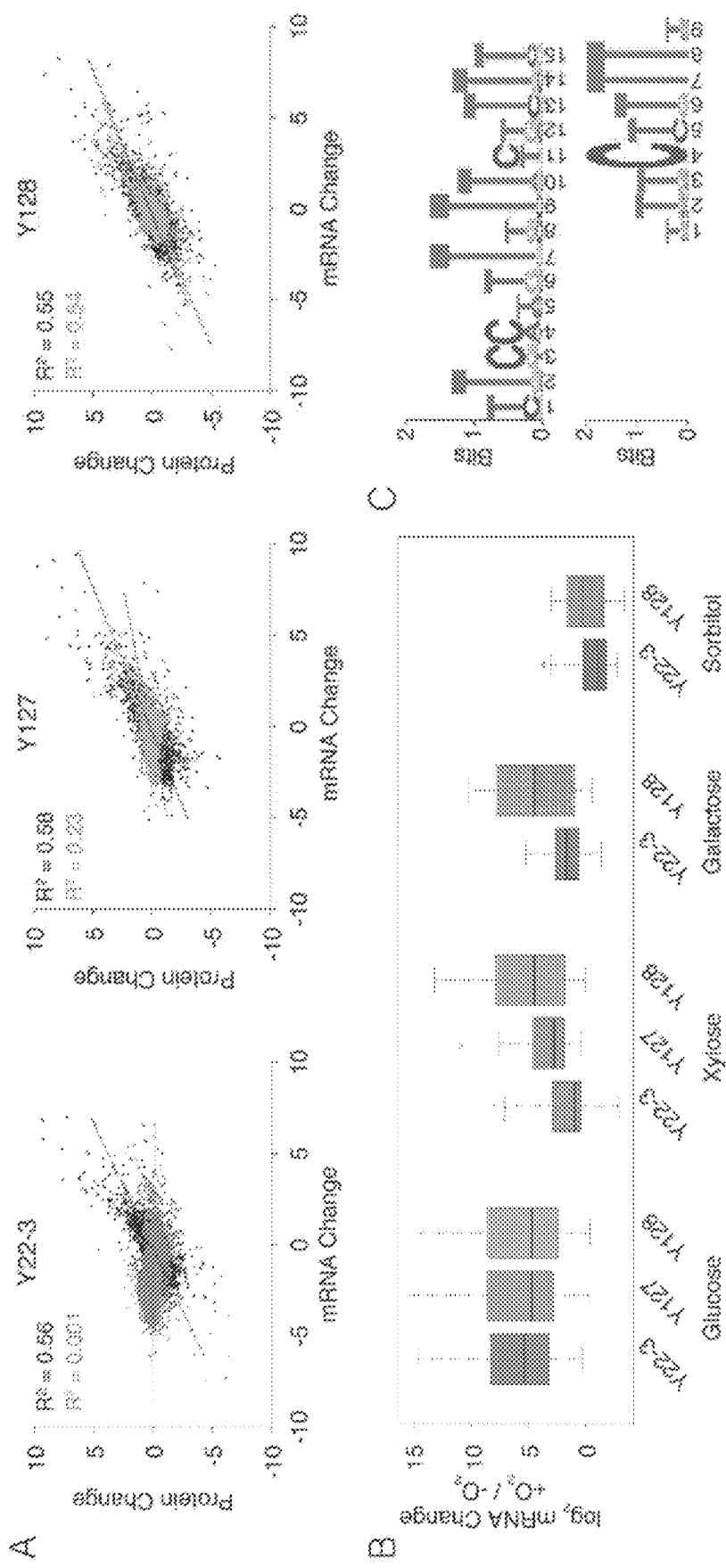
FIG. 1 illustrates three yeast strains, Y22-3, Y127, and Y128, grown on glucose and xylose in the presence or absence of oxygen. A) Correlation between mRNA and protein log 2 fold change glucose and xylose .+-.O2 across the strain panel. B) Log 2 fold change of 21 hypoxic genes for each strain examined in different growth media. There were differences in response to hypoxia. C) Identified motif from sequences upstream of the hypoxic genes (top) and known Azflp motif (bottom).

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". Promoters that allow the selective expression of a gene in most cell types are referred to as "inducible promoters".

A "host cell" is a cell which has been transformed or transfected, or is capable of transformation or transfection by an exogenous polynucleotide sequence. A host cell that has been transformed or transfected may be more specifically referred to as a "recombinant host cell". Preferred host cells for use in methods of the invention include yeast cells, particularly yeast cells of the genus *Saccharomyces*, more preferably of the species *Saccharomyces cerevisiae*.

The nucleic acid sequence for the AZF1 ORF gene is recited in SEQ ID NO:1:

ATGCCTCCTCCAACTGCACAGTTCATGGGCCCTACGCAGGCGGGACAAAA

TGAAAGCCAAAATCAATCATCAGGCGAAGCTGGGGAGCAAAACCAGGAGC

ATGGGCAAGGCCCTACTCCTATTCTTAATCAAAGTCAACCGGCTTCTTCT

CAACCGCAACATCAACAACAAAGGAATGAGTCGATTTCATATTATACAAA

TTTCAACCAGCCACGATATTCCACGGACGCCTCTATCAACTCATTCTTGA

ACATATCTGATAACGTACCAGTAACAAGTACAGGAGGACCTAGTTCTGGC

GGCGCCTATTCCAATCTTCCACGATTATCCACTTCAAGTACACATCAACC

GCCAGACCTGTCGCAAATCGGACGCGGCTTTTCCATTGTAAACAACCTCT

TCCCACAACAACAGCAGCTTCAAAATCAGCATCGGCAACAGCAGCAACAA

CAACAACAGCAGTCGCACCAGCAGCCTCCCTTCAAGACCCCTTCATTTTC

GACGGGATTAACGGGAAGTTCTTCTCAATATCAATTTTTACCAAGAAATG

ATAATACTTCGCAGCCACCTTCAAAAAGAAACTCTGTTTATCTTGGACCT

AATGATGGGCCTGATTTTGAATTTTTCAGTATGCAGCAGTCACAGCAACC

GCAGTTCCAGCCTAGCAGTAGAAGAGAATCAAACTCTATGAGACCTCCAC

TGTTAATACCTGCAGCAACTACTAAAAGCCAGTCCAATGGCACCAATAAT

AGTGGGAATATGAACACAAATGCAGATTATGAATCATTTTTTAATACTGG

TACAAACAACAGTAATTCTAATCAGAACCCGTACTTTTTGAGTTCAAGAA

ATAATTCTTTGAAGTTTAATCCTGAAGATTTCGATTTTCAATTCAAAAGG

CGGAATTCTTTTGTTAGAGGTACTTTGGACCATAGCAGCCAAAATGCGTT

TATACCTGAATCAAGATTAAACTCACTATCCGTTAACAACAAAGCTAATG

GTGATCCTGTCGCGGATAATGTTACCAATAACATGAAAGGAAAAAGTAAT

GAAGTTGACAATGATGATGGCAATGACAGTAGCAATAACAATAACAACAA

CAACAACAACAACAACAATGAAAACAACAATGACAACAATAATGATAATA

ACGACAATAGTATTAATTCCGCCACCAGTACTAATATCCCAAACCAAGAG

GACCATAGCCTTGCTTCTACCGATACCACAAGCAATAGTAGGAAAGATCT

AAAAGAAATAGAACAAAGACTTCGAAAACATTTGAATGATGAGGATAATT

ACTCTAGTGCTATATCAAGACCATTGGATAAAAACGACGTAATTGAAGGC

AGTGAGGGATTGAACAAACATATAGACGAGTCTGGTATGCAACCTAATAT

TATCAAGAAAGGAAAAGGATGATTCTACTGTGTACGTCAAGAATGAGA

TGCCCCGTACTGATCCCCCGATGAGTAAAGACAATTCTACTTCTGCTGAA

GGAGCAGCAATGGCAAACTTTTCTGGTAAAGAACCTCCTATACCTGACAT

AAGTTCAGTAAGTGATGATGCTACTAACCTGATAGGTGCAACAAAGGTCG

ACCAACTAATGTTGATTATTCAAGCAAGAAAGAAAGGTTTCACGGAGAAA

GTAAATACCACTCAAGATGGAGACTTACTGTTTAACCAAACGATGGACAT

-continued

TTTACCACCTAAAAGCGAACTAGTAGGTGGTGTGGAGAAACCAAAAGGCA

CACAAAATACACGAGCAGTTAAAAAACATGAATGTCCCTATTGTCATCGG

CTTTTTTCGCAAGCGACTCATCTGGAGGTTCACGTTCGTTCTCATATAGG

GTACAAACCATTCGTTTGTGATTATTGTGGCAAACGTTTTACTCAGGGTG

GGAACTTAAGAACTCATGAACGACTACACACAGGTGAAAAACCGTATTCA

TGTGATATTTGTGATAAAAATTTTCTAGGAAAGGGAACTTAGCTGCTCA

CTTGGTTACTCACCAAAAATTGAAACCATTTGTTTGCAAGCTTGAAAACT

GCAACAAGACCTTCACTCAACTAGGAAATATGAAGGCCCATCAAAATAGA

TTTCATAAGGAAACATTAAATGCCTTAACGGCAAAATTAGCTGAGATGAA

TCCATCTGAGAATATTCCACTTGAAGAGCGGCAACTTTTGGAGTACTTTG

CGTCCATTTATAAAAATTCAAACAGGGGAATTAAAGGTAGAGGAAAAGGT

GTAGGAACCAAAAAATCAACAATTTCCTCACCAGAAAACCATCCTGCGAG

CACAATTTTGAATCCAAATACAAATGCAAATAATGCTATTGCTAATGATT

CTGAAAATAACGGCAACCCTGAAGGTAACATTGACAGCAGTAGTAACAGC

AATCCGGGCTCACATAGTATGATTTCGCCGACGCAAAAAGACATGGGTAC

GTTGCAATCACAATTTATCCAAAATAATTTTAACAATTCTGTGAACAGTT

CGAATCCGTCCAACCAACCAATCATAAACTACAATTACACCACACTTCCT

CATTCTAGATTAGGAAGTAGTAGTTCCAGCAATACCAACAATAATAACAG

CAACTTTTCGGTAGGTGCAGCTCCGGGTGTATTAATGGCGCCAACCACCA

ATAATGACTTCAGTTTCAACTTGGATCAATCTAATGATAATGAAAGATCT

CAACAAGAACAAGTGAGATTTAAGAACATTAATTACAAAAGCTAG.

The nucleic acid sequence for the AZF1 gene and flanking sequence in the MoBY 2.01 plasmid is recited in SEQ ID NO:2:

ATAGTACTGCAGATTCGGAAGATGTGAAAGATATTGATTTTGAGAATTAC

GGTTGTGATGAAGAGGATATGAATAAAGAAGACAATTTGTTAGCCGCACA

ATTTTTAAATAATTTACGTTTAAATTCTCCCTCAGCAACAACACCAAGTA

ACATTACCGAGAGCGAAATTGATTCCGCCCAGGATGGAAGTGGATGGGAC

GACCTCAGCGATACCGATGGCTTTATTACAAATGGTACCACAGAATCCTT

CGATGAAACAACAAACCCTGTAACAACCGCAAGCACCCCAAAATTATTCG

GAAAACCTATTAAAATTAATAAAAGTTGGAATGATGAGTTGAATGATGAT

GGCTGGATTCAAGATGAAAGCGGCCCATCAAAGGTGCCTCAAAAACACAC

AAGGCCACAAAATTCAACGTTGGCAAAATCCATCGCTCCTAGCTCAAGGC

TTTCTATCAAGAAGAAGAAAACAACGATCCTAGCACCAAGAAACATTGCT

AGTAACTCTACTGTTACCACCAAATCGTCACTGTCCAATAAAACTGCAAG

AAGTAAGCCTATAAGTAGTATCCGCGGCTCGGTAACCAAGAAAGGAAATG

TTGACGGCTGGGATGATGATGGGGATTCAGACTCCTGGGATACGAATTGG

TGATCCCAAGACTTATATAGCCCTACGTATTGTAGAAGGATATATTCAGT

GTTAATCGTTATTTAGAAACATTACGCCCGTGCCCCGCGATTTCGCTTCT

TTGAGAAGTGGAGGAAAAGAAGGGTCCCTTTAATTCCAGTAGAAATGAAG

CATAAGCAAGAAGAGTCATCAGAAAAGGGAACCTTGTAGTACTATAGATG

GTCCCACAGAGAAATTAATTGGGACAAAAACAGCTACACAAGCGATATAC

TTCAAAAGATTCAGATATTGAAAAATTACCAGCCATGCCTCCTCCAACTG

CACAGTTCATGGGCCCTACGCAGGCGGGACAAAATGAAAGCCAAAATCAA

TCATCAGGCGAAGCTGGGGAGCAAAACCAGGAGCATGGGCAAGGCCCTAC

TCCTATTCTTAATCAAAGTCAACCGGCTTCTTCTCAACCGCAACATCAAC

AACAAAGGAATGAGTCGATTTCATATTATACAAATTTCAACCAGCCACGA

TATTCCACGGACGCCTCTATCAACTCATTCTTGAACATATCTGATAACGT

ACCAGTAACAAGTACAGGAGGACCTAGTTCTGGCGGCGCCTATTCCAATC

TTCCACGATTATCCACTTCAAGTACACATCAACCGCCAGACCTGTCGCAA

ATCGGACGCGGCTTTTCCATTGTAAACAACCTCTTCCCACAACAACAGCA

GCTTCAAAATCAGCATCGGCAACAGCAGCAACAACAACAACAGCAGTCGC

ACCAGCAGCCTCCCTTCAAGACCCCTTCATTTTCGACGGGATTAACGGGA

AGTTCTTCTCAATATCAATTTTTACCAAGAAATGATAATACTTCGCAGCC

ACCTTCAAAAAGAAACTCTGTTTATCTTGGACCTAATGATGGGCCTGATT

TTGAATTTTTCAGTATGCAGCAGTCACAGCAACCGCAGTTCCAGCCTAGC

AGTAGAAGAGAATCAAACTCTATGAGACCTCCACTGTTAATACCTGCAGC

AACTACTAAAAGCCAGTCCAATGGCACCAATAATAGTGGGAATATGAACA

CAAATGCAGATTATGAATCATTTTTTAATACTGGTACAAACAACAGTAAT

TCTAATCAGAACCCGTACTTTTTGAGTTCAAGAAATAATTCTTTGAAGTT

TAATCCTGAAGATTTCGATTTTCAATTCAAAAGGCGGAATTCTTTTGTTA

GAGGTACTTTGGACCATAGCAGCCAAATGCGTTTATACCTGAATCAAGA

TTAAACTCACTATCCGTTAACAACAAAGCTAATGGTGATCCTGTCGCGGA

TAATGTTACCAATAACATGAAAGGAAAAAGTAATGAAGTTGACAATGATG

ATGGCAATGACAGTAGCAATAACAATAACAACAACAACAACAACAACAAC

AATGAAAACAACAATGACAACAATAATGATAATAACGACAATAGTATTAA

TTCCGCCACCAGTACTAATATCCCAAACCAAGAGGACCATAGCCTTGCTT

CTACCGATACCACAAGCAATAGTAGGAAAGATCTAAAAGAAATAGAACAA

AGACTTCGAAAACATTTGAATGATGAGGATAATTACTCTAGTGCTATATC

AAGACCATTGGATAAAAACGACGTAATTGAAGGCAGTGAGGGATTGAACA

AACATATAGACGAGTCTGGTATGCAACCTAATATTATCAAGAAAAGGAAA

AAGGATGATTCTACTGTGTACGTCAAGAATGAGATGCCCCGTACTGATCC

CCCGATGAGTAAAGACAATTCTACTTCTGCTGAAGGAGCAGCAATGGCAA

ACTTTTCTGGTAAAGAACCTCCTATACCTGACATAAGTTCAGTAAGTGAT

GATGCTACTAACCTGATAGGTGCAACAAAGGTCGACCAACTAATGTTGAT

TATTCAAGCAAGAAAGAAAGGTTTCACGGAGAAAGTAAATACCACTCAAG

ATGGAGACTTACTGTTTAACCAAACGATGGACATTTTACCACCTAAAAGC

GAACTAGTAGGTGGTGTGGAGAAACCAAAAGGCACACAAAATACACGAGC

AGTTAAAAAACATGAATGTCCCTATTGTCATCGGCTTTTTTCGCAAGCGA

CTCATCTGGAGGTTCACGTTCGTTCTCATATAGGGTACAAACCATTCGTT

TGTGATTATTGTGGCAAACGTTTTACTCAGGGTGGGAACTTAAGAACTCA

-continued

```
TGAACGACTACACACAGGTGAAAAACCGTATTCATGTGATATTTGTGATA

AAAAATTTTCTAGGAAAGGGAACTTAGCTGCTCACTTGGTTACTCACCAA

AAATTGAAACCATTTGTTTGCAAGCTTGAAAACTGCAACAAGACCTTCAC

TCAACTAGGAAATATGAAGGCCCATCAAAATAGATTTCATAAGGAAACAT

TAAATGCCTTAACGGCAAAATTAGCTGAGATGAATCCATCTGAGAATATT

CCACTTGAAGAGCGGCAACTTTTGGAGTACTTTGCGTCCATTTATAAAA

TTCAAACAGGGGAATTAAAGGTAGAGGAAAAGGTGTAGGAACCAAAAAAT

CAACAATTTCCTCACCAGAAAACCATCCTGCGAGCACAATTTTGAATCCA

AATACAAATGCAAATAATGCTATTGCTAATGATTCTGAAAATAACGGCAA

CCCTGAAGGTAACATTGACAGCAGTAGTAACAGCAATCCGGGCTCACATA

GTATGATTTCGCCGACGCAAAAAGACATGGGTACGTTGCAATCACAATTT

ATCCAAAATAATTTTAACAATTCTGTGAACAGTTCGAATCCGTCCAACCA

ACCAATCATAAACTACAATTACACCACACTTCCTCATTCTAGATTAGGAA

GTAGTAGTTCCAGCAATACCAACAATAATAACAGCAACTTTTCGGTAGGT

GCAGCTCCGGGTGTATTAATGGCGCCAACCACCAATAATGACTTCAGTTT

CAACTTGGATCAATCTAATGATAATGAAAGATCTCAACAAGAACAAGTGA

GATTTAAGAACATTAATTACAAAAGCTAGCAGGCCTTAGAGGCACTACCT

TTTTTTTTTTTCGAGTTTCTACACCGTAGTATCTGATTTCATAGTGGTA

TTCGTCAAACTTAACCCACAAGTGTCACTTTTCCTTTCTTTTTTCTTTT

CTTGAAGAACTGCATGGTTTTCTAGCTCTTTTTCACTTTTTTGAGGTTTT

ATTTATCTTGTATTCTTTTTTCTATTATTTTAAAGGTTCAATTTCTATC

GACGG.
```

A polypeptide "substantially identical" to a comparative polypeptide varies from the comparative polypeptide, but has at least 80%, preferably at least 85%, more preferably at least 90%, and yet more preferably at least 95% sequence identity at the amino acid level over the complete amino acid sequence, and, in addition, it possesses the ability to increase anaerobic xylose fermentation capabilities of a host yeast cell in which it has been engineered and over-expressed.

The term "substantial sequence homology" refers to DNA or RNA sequences that have de minimus sequence variations from, and retain substantially the same biological functions as the corresponding sequences to which comparison is made. In the present invention, it is intended that sequences having substantial sequence homology to the nucleic acids of SEQ ID NO:1 or 2 are identified by: (1) their encoded gene product possessing the ability to increase anaerobic xylose fermentation capabilities of a host yeast cell in which they have been engineered and over-expressed; and (2) their ability to hybridize to the sequence of SEQ ID NO:1 or 2, respectively, under stringent conditions.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=$81.5+16.6(\log_{10}[Na+])+0.41(\%\ G+C)-(600/N)$, where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washed at 0.02M $NaH_2PO_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

As used herein the term "gene product" shall refer to the biochemical material, either RNA or protein, resulting from expression of a gene.

The term "heterologous" is used for any combination of DNA sequences that is not normally found intimately associated in nature (e.g., a green fluorescent protein (GFP) reporter gene operably linked to a SV40 promoter). A "heterologous gene" shall refer to a gene not naturally present in a host cell (e.g., a luciferase gene present in a retinoblastoma cell line).

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The term "biofuel" refers to a wide range of fuels which are in some way derived from biomass. The term covers solid biomass, liquid fuels and various biogases. For example, bioethanol is an alcohol made by fermenting the sugar components of plant materials and it is produced largely from sugar and starch crops. Cellulosic biomass, such as trees and grasses, are also used as feedstocks for ethanol production and the present invention finds its primary application in this specific field. Of course, ethanol can be used as a fuel for vehicles in its pure form, but it is usually used as a gasoline additive to increase octane and improve vehicle emissions.

"Yeasts" are eukaryotic micro-organisms classified in the kingdom Fungi. Most reproduce asexually by budding, although a few undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is shown by their placement in separate phyla, principally the Ascomycota and the Basidiomycota. The budding yeasts ("true yeasts") are classified in the order Saccharomycetales.

The nucleotides that occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., a, (3, etc.) may sometimes be used.

II. The Invention

The present invention is largely related to the inventors' research efforts to improve the rate of xylose conversion to ethanol. With this goal in mind, the inventors used transcriptomic, proteomic, and phosphoproteomic profiling and bioinformatic analysis to study a series of yeast strains engineered and evolved for different levels of anaerobic xylose fermentation. Specifically, strain Y22-3 was engineered with the minimal genes required for xylose utilization but cannot grow on only xylose. Strain Y127 was evolved in the laboratory from Y22-3, and while it can respire xylose aerobically it cannot ferment xylose anaerobically. Strain Y128 was evolved from Y127 and is capable of fermenting xylose to ethanol under anaerobic conditions. By comparing multi-omic profiles across these strains, the inventors implicated physiological responses that occur in Y128 but not the other engineered strains, to understand the bottlenecks in anaerobic xylose fermentation.

The inventors discovered that only strain Y128 can fully activate the hypoxic response when grown anaerobically on xylose. Bioinformatic analysis of this group of genes identified a shared DNA sequence motif in the promoters of the genes, which matched the known binding site of the transcription factor AZF1 (asparagine-rich zinc finger protein). AZF1 is a poorly characterized factor implicated in the response to poor carbon sources. The inventors found that over-expression of AZF1 in strain Y128 improves the rate of anaerobic xylose fermentation, while deletion of AZF1 slows anaerobic xylose fermentation.

These trends were recapitulated in a second yeast strain engineered for anaerobic xylose fermentation, indicating that the response is not specific to Y128. AZF1 over-expression alone in a strain unable to ferment xylose was not sufficient to produce anaerobic xylose fermentation.

Accordingly, the present invention provides an isolated nucleic acid having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in yeast of the isolated nucleic acid provides increased rate of anaerobic xylose fermentation in the yeast relative to a control yeast lacking over-expression of the isolated nucleic acid.

The present invention will employ strong heterologous promoters, preferably inducible versions thereof. Suitable promoters for use in the invention include, e.g., the ACT1, PGK1, TDH3, TEF1, or TEF2 promoters, or promoters of other highly expressed *S. cerevisiae* genes. In preferred embodiments, the promoter is an inducible heterologous promoter and enhanced anaerobic xylose fermentation in the recombinant yeast is conferred by induction of the inducible heterologous promoter. Inducible heterologous promoters suitable for use in the present invention include, e.g., the GAL4, CUP1, PHO5, or tetO7 promoter.

In another aspect, the invention is directed to a recombinant yeast engineered to contain one or more of the isolated nucleic acids having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid.

The recombinant yeast is preferably of the genus *Saccharomyces*, more preferably of the species *S. cerevisiae*. Such recombinant yeast will have at least one copy of the gene which enhances anaerobic xylose fermentation, and may have two or more, usually not exceeding about 200, depending upon whether the construct is integrated into the genome, amplified, or is present on an extrachromosomal element having multiple copy numbers. Integration or non-integration may be selected, depending upon the stability required for maintenance of the extrachromosomal element, the stability of the particular extrachromosomal element prepared, the number of copies desired, the level of transcription available depending upon copy number, and the like.

As can be appreciated, the present invention contemplates the use of recombinant yeast as described herein for use in the production of biofuel, including certain exemplary recombinant *S. cerevisiae* strains specifically identified herein, including, e.g., GLBRC Y22-3, GLBRC Y127, GLBRC Y128, GLBRC Y36, GLBRC Y132, GLBRC Y133, Y133 azf1, Y133 AZF1 MoBY, Y133 MoBY Control, CEN.PK113-5D Xylose Strain, CEN.PK113-5D Xylose Strain AZF1 MoBY, CEN.PK113-5D Xylose Strain MoBY Control and derivatives thereof.

The present invention further encompasses a method of providing a recombinant yeast useful in biofuel production. Such a method includes steps of introducing into an isolated yeast an isolated nucleic acid having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid.

Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into a cloning vector, the vector transformed into a cloning host, e.g. *Escherichia coli*, the cloning host grown up, lysed, the plasmid isolated and the fragment analyzed by restriction analysis, sequencing, combinations thereof, or the like.

Various vectors may be employed during the course of development of the construct and transformation of host cells. These vectors may include cloning vectors, expression vectors, and vectors providing for integration into the host or the use of bare DNA for transformation and integration. The cloning vector will be characterized, for the most part, by having a replication original functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g. a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions. Of particular interest for the subject invention are the vectors and constructs for expression, either for extrachromosomal stable maintenance or integration, which in their stable form in the host are free of prokaryotic DNA.

For extrachromosomal stable maintenance, it may be necessary to provide for selective pressure on those hosts maintaining the construct. Stable maintenance may be achieved by providing for resistance against a cytotoxic agent, e.g. an antibiotic, such as kanamycin or G418, or by imparting prototrophy to an auxotrophic host. For stable maintenance in a yeast host, the 2 micron origin of replication may be employed or a combination of a centromere, e.g. CEN3, and ars. For integration, generally homologous integration will be desirable, so that the construct will be flanked by at least about 50 bp, more usually at least about 100 bp on each side of the construct of a sequence homologous with a sequence present in the genome of the host.

The yeast host may be transformed in accordance with conventional ways. Conveniently, yeast protoplasts may be transformed in the presence of a fusogen, such as a non-ionic detergent, e.g. polyethyleneglycol.

Yeast strains that may serve as yeast hosts include, for example, certain yeast strains useful in biofuel production such as, e.g., GLBRC Y22-3, GLBRC Y127, GLBRC Y128, GLBRC Y36, GLBRC Y132, GLBRC Y133, Y133 azf1, Y133 AZF1 MoBY, Y133 MoBY Control, CEN.PK113-5D Xylose Strain, CEN.PK113-5D Xylose Strain AZF1 MoBY, CEN.PK113-5D Xylose Strain MoBY Control and derivatives thereof.

In another aspect, the present invention provides a method for producing ethanol from a recombinant yeast. Such a method includes steps of: (a) culturing under ethanol-producing conditions a recombinant yeast engineered to contain one or more of the isolated nucleic acids having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid; and isolating ethanol produced by the recombinant yeast.

Particularly useful recombinant yeast for biofuel production methods are based on *S. cerevisiae*.

In view of the various industrial uses and storage conditions the present recombinant yeasts will be subjected to, the invention further encompasses yeast inoculums which contain at least (a) a recombinant yeast recombinant yeast engineered to contain one or more of the isolated nucleic acids having: (a) the nucleotide sequence of SEQ ID NO:1; or (b) a nucleotide sequence which hybridizes under stringent conditions to SEQ ID NO:1, or to a fully complementary nucleotide sequence thereof, wherein over-expression in the yeast of the isolated nucleic acid provides increased rate of anaerobic xylose fermentation in the yeast relative to a control yeast lacking over-expression of the isolated nucleic acid; and (b) a culture medium.

The following experimental data are provided to illustrate the invention. It is to be understood that a person skilled in the art who is familiar with the methods may use other yeast strains, recombinant vectors, and methodology which can be equally used for the purpose of the present invention. These alterations are included in the scope of the invention.

III. Examples

In this section, the inventors describe various materials, methods and results related to and supportive of the present invention.

Example 1. Over-Expression of Azf1 Improve the Rate of Anaerobic Xylose Fermentation in Engineered Yeast Strains Background and Results Genomic Analysis of Evolved Yeast Strains.

The inventors generated a series of evolved yeast strains with variable xylose consumption traits: parental strain Y22-3 minimally engineered with xylose metabolism genes was evolved for aerobic grown on xylose; the emergent Y127 strain was further evolved anaerobically to produce the xylose fermenting strain Y128. Null mutations in the iron-sulfur protein ISU1 and the stress-activated HOG1 kinase enable xylose respiration in Y127, while addition loss-of-function alleles in IRA2, an inhibitor of Protein Kinase A (PKA), and xylitol reductase GRE3 facilitate anaerobic xylose fermentation by Y128.

To better understand how these mutations enabled anaerobic xylose fermentation the inventors profiled transcriptome and proteome differences across the three yeast strains growing on glucose or xylose in the presence or absence of oxygen. When grown on glucose, all three strains had similar transcriptomic and proteomic responses to anaerobic conditions; however, there were significant differences when grown on xylose.

Patterns Between Sugar Source and Hypoxic Response.

Figure 2:
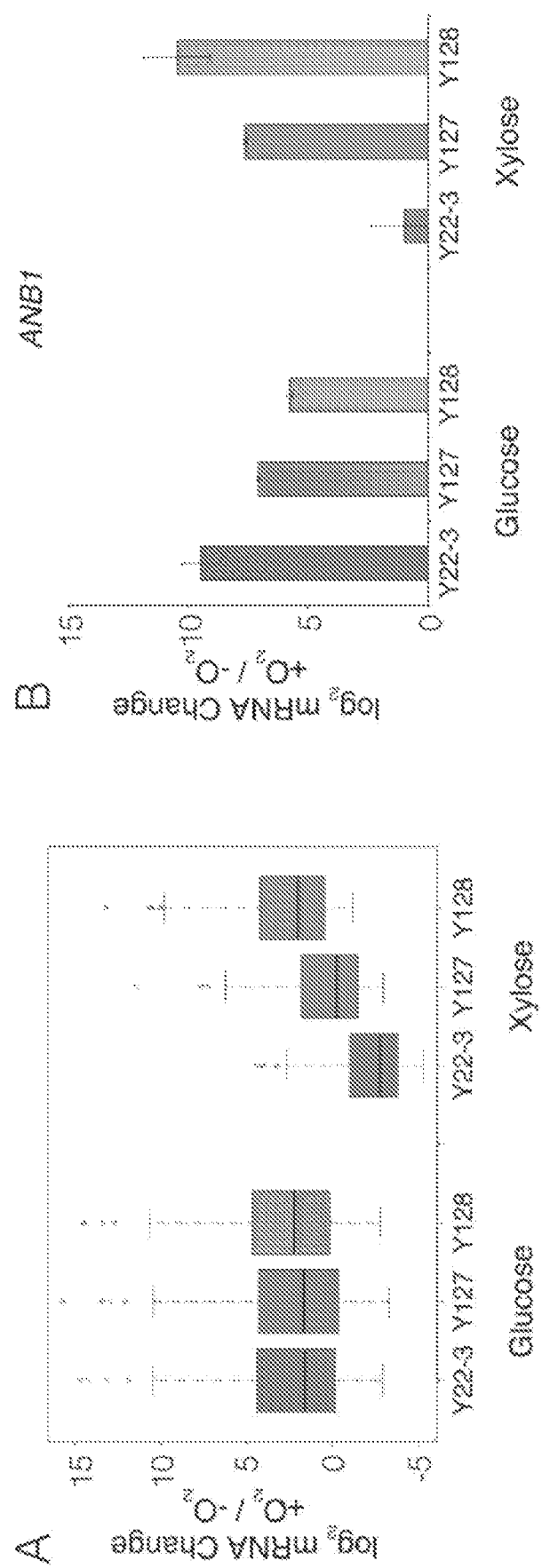
FIG. 2 illustrates 128 genes with a progressive pattern of anaerobic-xylose induction. A) Log 2 mRNA change for Y22-3, Y127, and Y128 in glucose±O2 and xylose±O2 for the 128 genes with a progressive increase in expression in xylose±O2. B) Log 2 mRNA change for ANB1 in the strains in glucose±O2 and xylose±O2. ANB1 is a hypoxic gene and was one of the genes used to identify the motif in FIG. 1C.

A striking difference emerged at the proteomic level: parental strain Y22-3 grown on xylose and shifted to anaerobic conditions showed substantial transcript changes but little change in corresponding protein abundance (FIG. 1A). The correlation between mRNA and protein differences was somewhat higher for strain Y127, and fully recovered in Y128 to a level comparable to when glucose was the carbon source (FIG. 1A). This suggested a potential translational defect in Y22-3 that is progressively restored in Y127 and Y128, respectively. Among the proteins strongly induced in Y128 but not the other strains growing anaerobically on xylose was ANB1p, required for anaerobic protein translation and synthesized as part of the hypoxic response (FIG. 2B). Much of the hypoxic response failed to initiate in Y22-3 and to some extent Y127 grown on xylose. These transcripts were induced in response to anaerobosis in all three strains growing on glucose, but they were largely uninduced in xylose-grown Y22-3. The response was partially restored in Y127, and the genes were fully induced in Y128 comparable to glucose-grown Y128 (FIG. 1B). The anaerobic response could not be simply explained by anaerobic growth, since Y127 showed partial induction of the genes despite an inability to grow anaerobically on xylose. The difference in strain responses was recapitulated on galactose, since Y22-3 mounted only a subtle response to anaerobosis, and to some extent the non-metabollizable sorbitol where even Y128 showed a decreased transcriptional response. The connection between sugar source and hypoxic response had not been previously reported in yeast but answers a longstanding question about the inability of strains to grow anaerobically on xylose.

Connection Between AZFIp and Anaerobic Growth on Non-Preferred Sugars.

Figure 3:
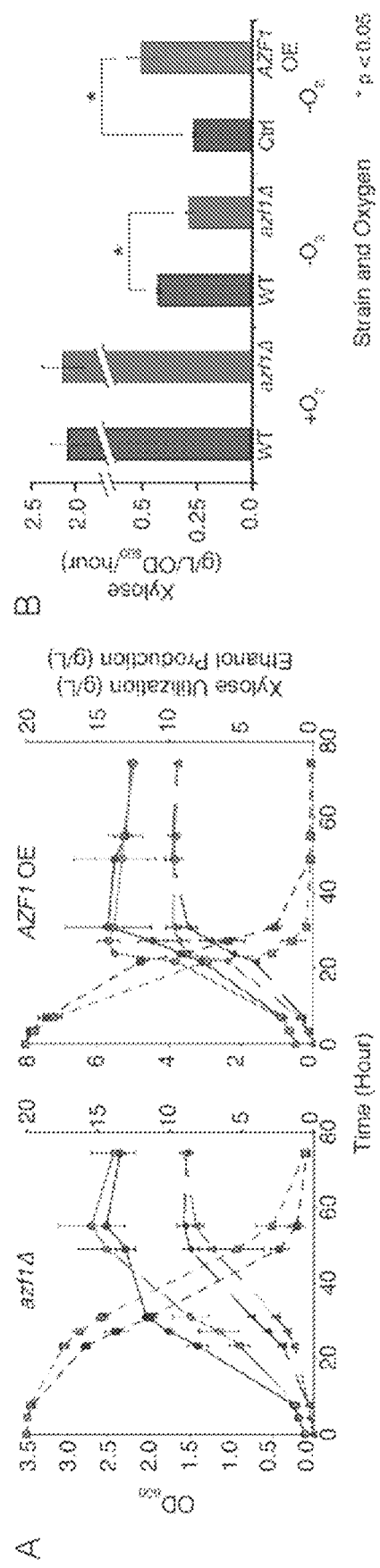
FIG. 3 illustrates the effect of over-expression and deletion of AZF1 in Y133 on anaerobic growth and sugar fermentation. A) OD600 (circles), xylose (squares), and ethanol (triangles) in azfl, AZF1 over-expression (OE), and WT control (grey) strains. Over-expression of AZF1 with the MoBY 2.0 plasmid improves anaerobic xylose fermentation while deletion of AZF1 decreases anaerobic xylose fermentation. B) Xylose utilization rates for deletion and OE of AZF1 compared to WT control rates. Over-expression of AZF1 with the MoBY 2.0 plasmid significantly increases the rate of anaerobic xylose utilization while deletion of AZF1 significantly decreases anaerobic xylose utilization (* $p<0.05$). The rates are similar in other growth conditions when AZF1 levels are perturbed.
Figure 4:
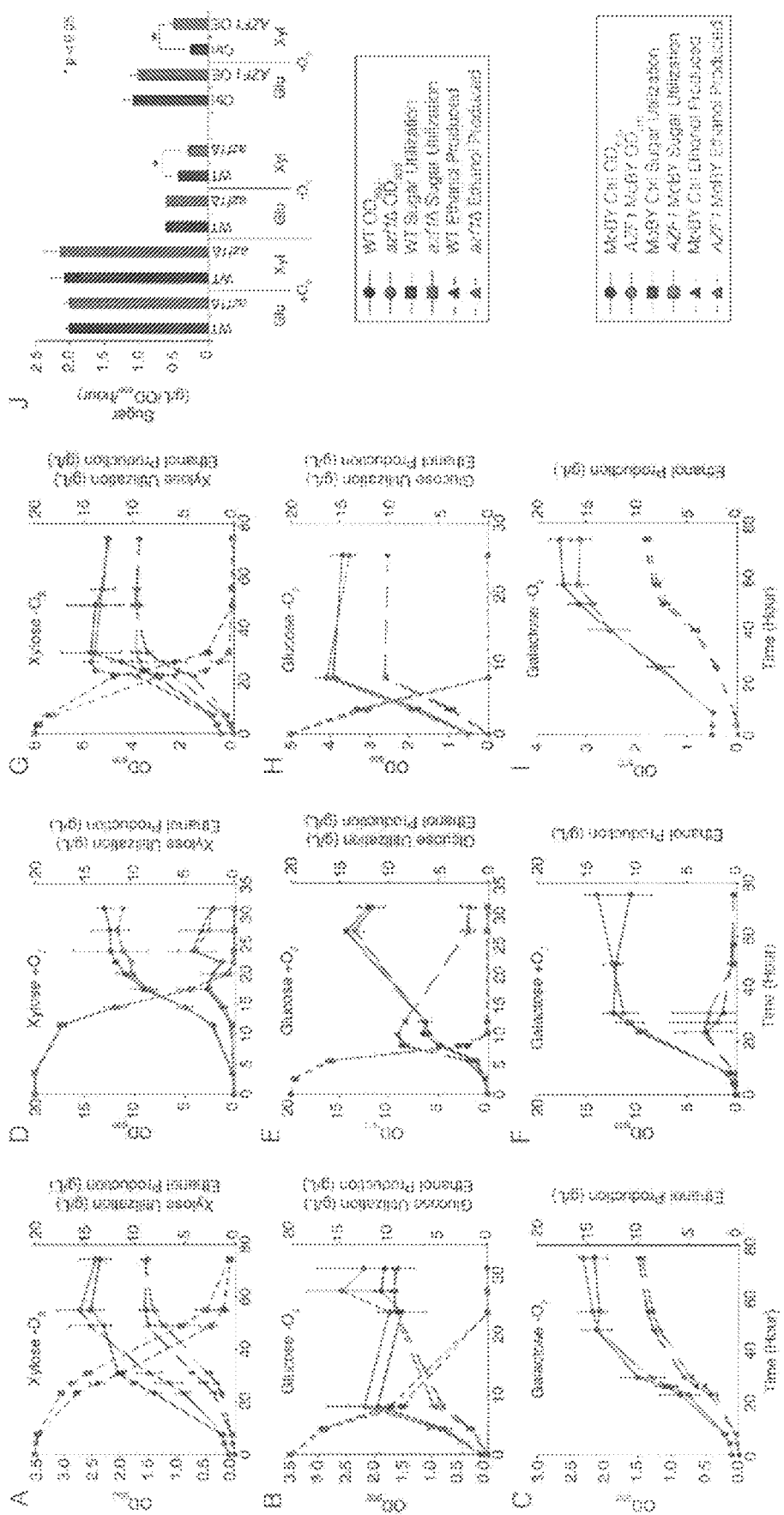
FIG. 4 illustrates the effect of over-expression and deletion of AZF1 in Y133 for different sugars and growth conditions. Panels A-I) OD600 (circles), sugar (squares), and ethanol (triangles) for Y133 azfl, Y133 AZF1-MoBY 2.0 over-expression, and Y133 WT or MoBY 2.0 control (black) for different sugars and growth conditions as indicated. Over-expression or deletion of AZF1 only has a significant impact on growth and fermentation in anaerobic growth in xylose. Panel J) Sugar utilization rates calculated for each strain during exponential growth. There is a significant (* $p<0.05$) increase in the rates of sugar utilization when AZF1 is over-expressed anaerobically using MoBY 2.0 plasmid in xylose and a significant (*<0.05) decrease in sugar utilization when AZF1 is deleted anaerobically in xylose. There is not a significant change in the rates of sugar utilization in other growth conditions when AZF1 expression is perturbed.
Figure 5:
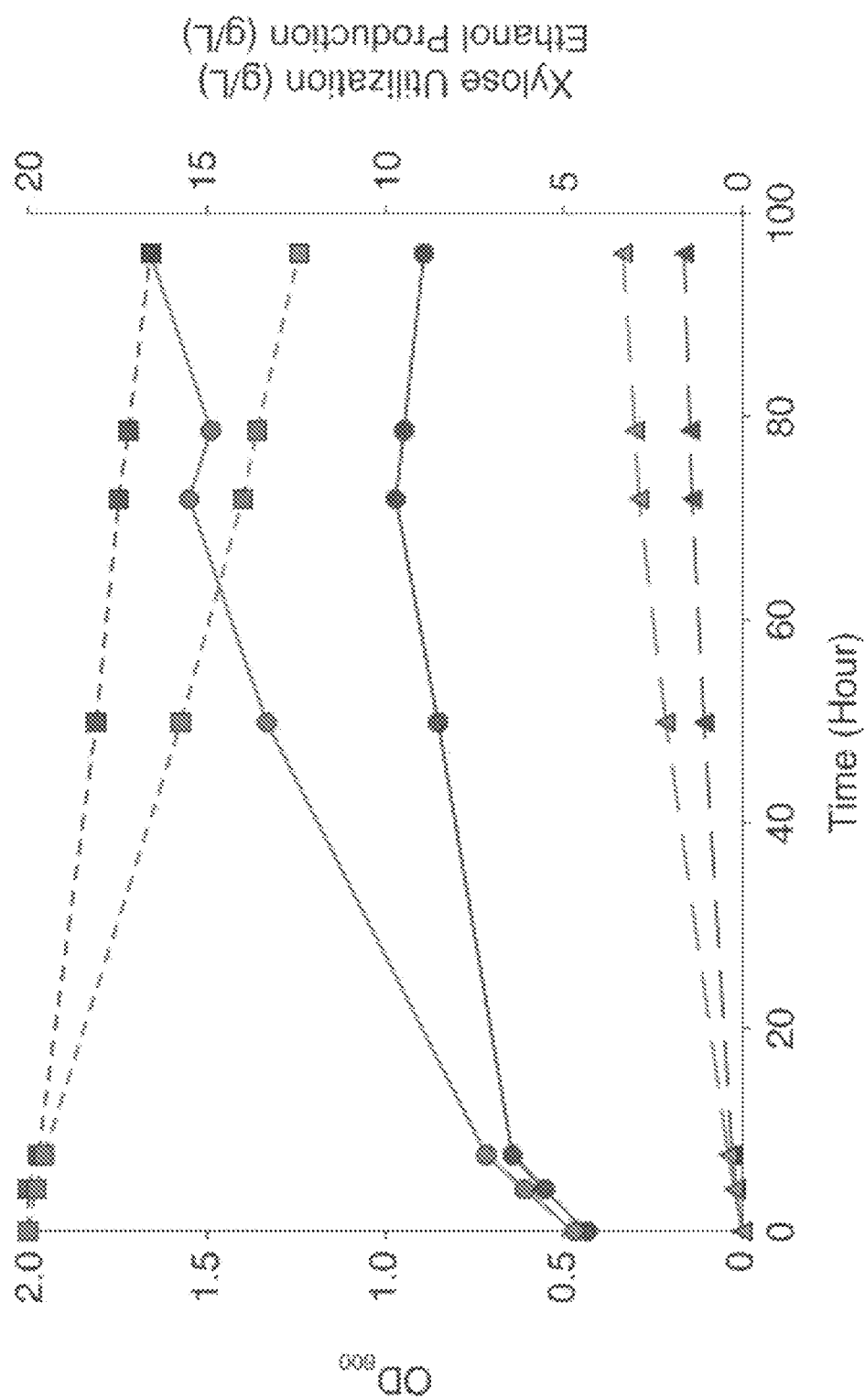
FIG. 5 illustrates AZF1 levels when perturbed in Y22-3 and a second strain harboring Y128 mutations. OD600 (circles), sugar (squares), and ethanol (triangles) for CEN.PK113-5D containing xylose utilization genes and with AZF1 MoBY 2.0 plasmid over-expression or empty vector control (black). Over-expression of AZF1 with MoBY 2.0 plasmid increases anaerobic xylose fermentation in this genetic background during anaerobic growth compared to the strain containing the control plasmid.
Figure 6:
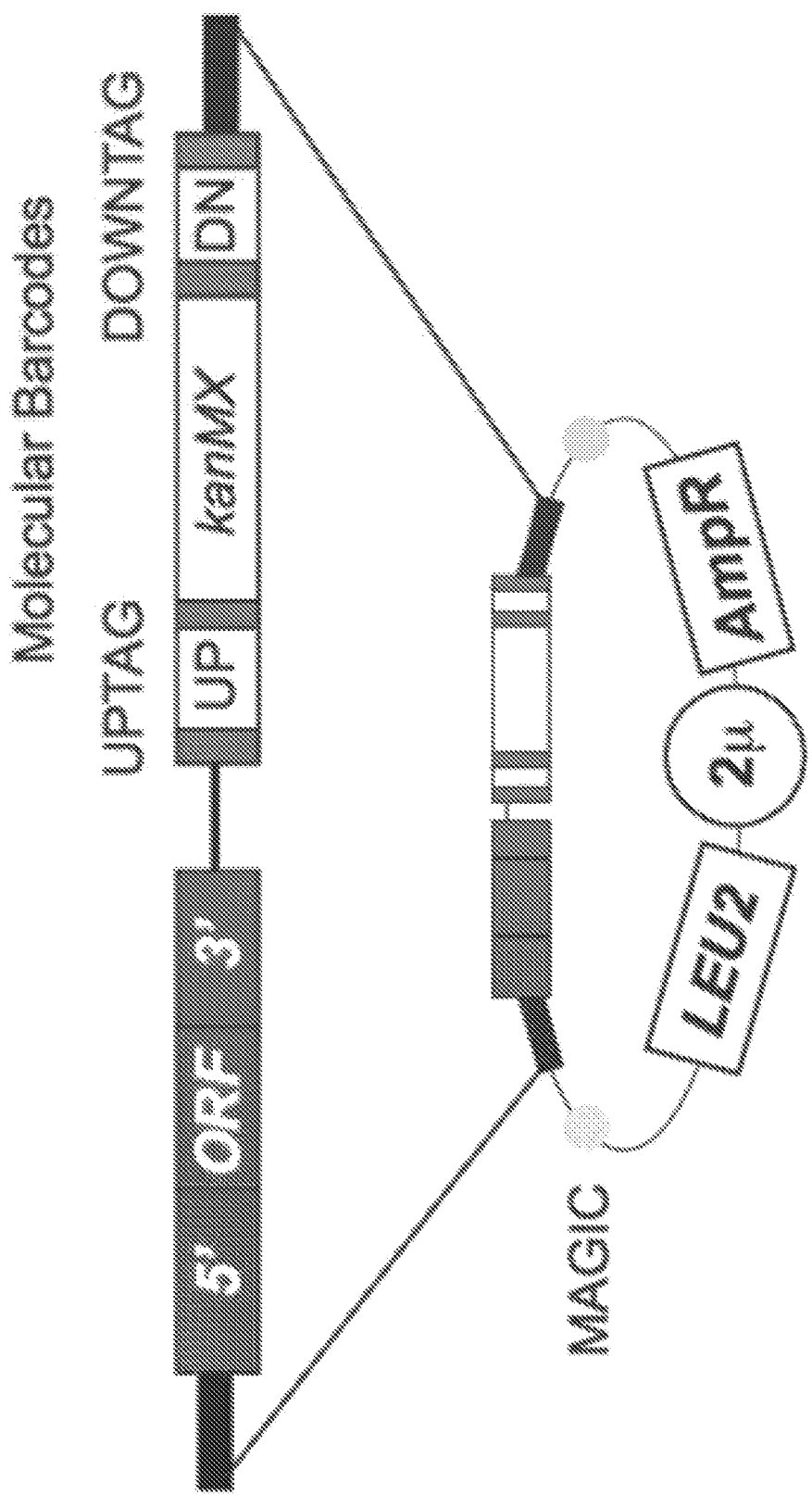
FIG. 6 illustrates a schematic of MoBY 2.0 plasmid from Magtanong et al. DNA ORF, flanking sequence and Molecular Barcodes from MoBY 1.0 library were directionally cloned into vector p5476 that contains a 2µ sequence that results in high-copy number using mating-assisted genetically integrated cloning (MAGIC) cloning.

To better understand the connection between sugar source and hypoxic response, the present inventors identified other genes with a progressive induction or repression in response to anaerobosis across the strain panel. They identified 128 genes with a similar progressive pattern of anaerobic-xylose induction (FIG. 2A)—these genes were enriched for ergosterol biosynthesis, cysteine metabolism, and translation. Motif analysis of the genes' promoters identified the binding site of AZFIp, a poorly characterized transcription factor responsive to non-preferred sugars (FIG. 1C). Over half (68) of the 128 progressively induced genes harbored the upstream AZFI motif ($p<1\times10-5$, hypergeometric test), including a majority of the classical hypoxic genes, suggesting a previously unknown role of AZF1p in the hypoxic response. Over-expression of AZF1 in Y133 increased rates of anaerobic growth, xylose consumption, and ethanol production but only when cells were grown on xylose and anaerobically (FIG. 3, FIG. 4). In contrast, deletion of AZF1 decreased growth and sugar fermentation (FIG. 3B, FIG. 4), largely specific to anaerobic xylose growth (FIG. 3B, FIG. 4). There was no effect when AZFI levels were perturbed in Y22-3, but results were similar in a second strain background harboring Y128 mutations (FIG. 5), which together reveal that Y128 mutations were required for the xylose effect. Perturbing AZF1 levels had a mild effect when cells were grown anaerobically on galactose (FIG. 4). These results reveal a previously unrecognized connection between AZFIp and anaerobic growth on non-preferred sugars.

Materials and Methods

Media and Growth Conditions.

YPD media contained 10 g/L yeast extract and 20 g/L peptone and sugars/carbon sources at defined concentrations: 20 g/L xylose, 20 g/L dextrose/glucose, and 20 g/L galactose unless otherwise noted. Antibiotics were added as needed at the following concentrations: 200 mg/L G418. For aerobic growth, cultures were grown at 30° C. with vigorous shaking in flasks. For anaerobic growth, media was incubated at 30° C. in a Coy anaerobic chamber (10% $CO_2$, 10% $H_2$, and 80% $N_2$) for ≥16 hours before inoculation, and cultures were grown at 30° C. in flasks using stir bars spinning at 300 rpm to prevent flocculation. Cultures were grown to saturation in YP-glucose medium, washed one time with the desired growth media, and inoculated at the required $OD_{600}$ value, as indicated. Cell growth was measured using $OD_{600}$ and extracellular sugar and ethanol concentrations were measured with HPLC-RID (Refractive Index Detector) analysis.

Strain and Cloning.

Saccharomyces cerevisiae strains used in this study and described in Table 1. The creation of Y22-3, Y127, and Y128 and their antibiotic marker-rescued counterparts (Y36, Y132, and Y133, respectively) was described previously. Gene knockouts were generated by homologous recombination of the KAN-MX or HYG-MX cassettes into the locus of interest and verified using diagnostic PCR. Over-expression of AZF1 was performed using the MoBY 2.0 plasmid compared to the empty vector control; cells were grown in media containing G418 for maintenance of the plasmid in Y133 or CEN.PK113-5D.

TABLE 1

Strains used.

| Strain Name | Description |
| --- | --- |
| GLBRC Y22-3 | CRB Strain expressing xylose utilization genes xylA, XYL3, TAL1 ($G418^R$) |
| GLBRC Y127 | Evolved Y22-3 for aerobic xylose utilization ($G418^R$) |
| GLBRC Y128 | Evolved Y127 for anaerobic xylose utilization ($G418^R$) |
| GLBRC Y36 | Y22-3 lacking KAN-MX cassette |
| GLBRC Y132 | Y127 lacking KAN-MX cassette |
| GLBRC Y133 | Y128 lacking KAN-MX cassette |
| Y133 azf1 | Y133 AZF1::kanMX ($G418^R$) |
| Y133 AZF1 MoBY | Y133 containing AZF1-MoBY 2.0 Plasmid ($G418^R$) |
| Y133 MoBY Control | Y133 containing Empty Vector MoBY 2.0 Plasmid ($G418^R$) |
| CEN.PK113-5D Xylose Strain | CEN.PK113-5D expressing xylose utilization genes xylA, XYL3, TAL1 |
| CEN.PK113-5D Xylose Strain AZF1 MoBY | CEN.PK113-5D Xylose Strain containing AZF1-MoBY 2.0 Plasmid ($G418^R$) |
| CEN.PK113-5D Xylose Strain MoBY Control | CEN.PK113-5D Xylose Strain containing Empty Vector MoBY 2.0 Plasmid ($G418^R$) |

Example 2. Rewired PKA Signaling Activates Sugar and Hypoxic Responses for Anaerobic Xylose Fermentation in Yeast Background and Results Microbes can be engineered for novel metabolism to produce biofuels and chemicals, but rerouting metabolic flux toward products remains a major hurdle. The inventors previously evolved a panel of Saccharomyces cerevisiae strains with progressive improvements in anaerobic fermentation of xylose, an abundant sugar in sustainable plant biomass used for biofuel production. Here the inventors used comparative multi-omics and network analysis across the strain panel to understand the mechanism of improved anaerobic xylose flux. The inventors discovered that the parent strain growing anaerobically on xylose but not glucose fails to activate the hypoxic response, whereas evolved strains restore the response, showing that sugar metabolism and oxygen sensing are connected. The inventors found that rewiring cellular signaling by up-regulating Protein Kinase A (PKA) in conjunction with Snf1 activation coordinates a cascade of regulatory events that mediate sugar and hypoxic responses during anaerobic xylose growth. Remarkably, deleting the PKA regulatory subunit decouples division and metabolism by halting growth but promoting rapid anaerobic xylose conversion. This provided an opportunity to distinguish proteome-wide phosphorylation events related to xylose-dependent growth versus fermentation. The inventors also found that simply fusing the regulatory subunit to a peptide tag combined the disparate benefits of wild-type and mutant strains, improving aerobic glucose growth as well as anaerobic xylose fermentation. Integrating transcriptomic, phosphoproteomic, and metabolomic data revealed a picture of the metabolic logic behind the improved flux of a non-native sugar.

An important strategy for sustainable energy is microbial production of biofuels from non-food plant material. However, many microbes including yeast cannot use xylose comprising ~30% of hemicellulosic sugars, especially under anaerobic conditions. Although cells can be engineered with the metabolic potential, they fail to recognize xylose as a consumable sugar for unknown reasons. The inventors used comparative systems biology across strains with progressive improvements in xylose utilization to understand the metabolic and regulatory logic of anaerobic xylose fermentation. Mutations in evolved strains trigger signaling pathways that are normally antagonistic, producing a cascade of regulatory events coordinating metabolism and growth. Integrative modeling implicates causal events linked to growth versus metabolism and shows the hypoxic response is dependent on carbon sensing in yeast.

Lignocellulosic plant biomass is a renewable substrate for biofuel production, but many microbes cannot natively use the pentoses that comprise a large fraction of the sugars. Budding yeast *Saccharomyces cerevisiae*, a key microbe in industrial biofuel production, is among the microbes that do not natively recognize xylose as a fermentable sugar, and even when engineered with conversion enzymes strains display low xylose utilization rates. The reason for this defect is not known but is likely regulatory.

Under conditions of optimal growth, including on the preferred sugar glucose, yeast promote high activity of Protein Kinase A (PKA) via increased cAMP that inactivates PKA regulatory subunit Bcy1. But in the presence of non-preferred carbon sources that result in low energy availability, cells activate the Snf1 kinase and derepress expression of genes involved in alternate carbon utilization. How to engineer cells to recognize a non-native sugar as fermentable has so far been elusive, especially under anaerobic conditions used by many industrial processes.

Genomic Analysis of Evolved Yeast Strains.

To enable anaerobic conversion of xylose to other products, the inventors evolved a series of yeast strains: stress-tolerant strain Y22-3 was minimally engineered with xylose isomerase and other genes required for xylose metabolism but was unable to metabolize xylose. This strain was passaged aerobically on xylose-containing medium to produce the Y127 strain that respires xylose aerobically but cannot use xylose anaerobically. Y127 was thus further evolved without oxygen, generating strain Y128 that can ferment xylose to ethanol anaerobically with yields similar to other engineered strains (Table 2). Null mutations in iron-sulfur cluster scaffold ISU1 and the stress-activated HOG1 kinase enable xylose respiration in Y127, while additional loss of IRA2, an inhibitor of RAS/PKA signaling, and xylitol reductase GRE3 facilitate anaerobic xylose fermentation by Y128. Although the required mutations are known, how they enable anaerobic xylose fermentation is unclear. Multi-omic approaches have been used to characterize alternate sugar metabolism in engineered strains, but distinguishing causal cellular differences from secondary effects is generally a significant challenge. Here, the inventors used comparative multi-omics across the strain panel to distinguish transcript, protein, and phospho-protein differences that correlate with improved xylose utilization capabilities, thereby implicating the mechanism of anaerobic xylose fermentation.

TABLE 2

Xylose utilization and ethanol production statistics comparing strains from this study to recently reported xylose fermentation strains in the literature

| St + A11:E21rain | Culture Conditions | Xylose Consumption Rate (g/g/hr) | Xylose Consumption Rate (g/OD/hr) | Ethanol Yield (g/g xylose) |
|---|---|---|---|---|
| Y128 | Anaerobic Batch, YPX, 3% Xylose | 0.194 ± 0.020 | 0.249 ± 0.017 | 0.421 ± 0.014 |
| Y184 bcy1 | Anaerobic Batch, YPX, 3% Xylose | 0.219 ± 0.040 | 0.263 ± 0.008 | 0.446 ± 0.006 |
| Y184 Bcy1-AiD | Anaerobic Batch, YPX, 3% Xylose | 0.260 ± 0.021* | 0.334 ± 0.019* | 0.445 ± 0.017 |
| H131-A3-AL^cs | Anaerobic Batch, 2x YNB, 4% Xylose | 1.866+ | — | 0.41 |
| TMB 3422 | Anaerobic Batch, 2x YNB, 5% Xylose | 0.580+ | — | 0.34 |
| TMB 3504 | Anaerobic Batch, 2x YNB, 5% Xylose | 0.760+ | — | 0.40 |
| SXA-R2P-E | Anaerobic Batch, YNB, 4% Xylose | — | 0.077 | 0.45 |
| SR8 | Anaerobic Batch, YNB, 4% Xylose | — | 0.129 | 0.38 |

Enteries marked with "—" indicate reported values were not measured with comparable units.
*$p < 0.05$ relative to Y128 (paired T-test)
+Comparing rates is obscured due to vastly different culturing conditions. Note, that although strains from Zhou and Cadete were reported to consume xylose at a faster rate, a significantly smaller portion of the consumed xylose was converted to ethanol Patterns Between Sugar Source and Hypoxic Response.

The inventors first compared the transcriptome and proteome responses of parental strain Y22-3 and evolved strains Y127 and Y128 growing on glucose or xylose, with or without oxygen. Glucose-grown strains showed large changes in mRNA and their encoded proteins when shifted to anaerobosis, in all three of the strains (FIG. 7A). Surprisingly, however, the strains showed major differences when grown on xylose: Y22-3 shifted to anaerobic conditions showed large changes in mRNA but little change in the encoded proteins (FIG. 7A). In Y127, changes in mRNA were partly correlated with changes in the encoded proteins, while the correlation between mRNA and protein change was fully recovered in xylose-grown Y128 shifted to anaerobic growth, on par with the correlation seen in glucose-grown cells (FIG. 7A). The defect in protein change seen in Y22-3 and Y127 suggests a translation defect. The inventors found that Y22-3 and to some extent Y127 showed defective induction of ANB1 (FIG. 12A), a gene whose activation as part of the hypoxic response is essential for anaerobic translation. In contrast, xylose-grown Y128 showed strong induction of ANB1 upon anaerobic shift. On further inspection, the inventors realized that over 70% of genes canonically involved in the hypoxic response (Table 3) were induced upon anaerobiosis in all strains growing on glucose but largely uninduced in xylose-grown Y22-3 and induced progressively stronger in Y127 and Y128, respectively (FIG. 7B). The response to hypoxia was not explained by growth differences, since all strains retained viability over the course of the experiment and since Y127 partially activated the response but was unable to grow anaerobically on xylose. Instead, this defect reveals a previously unrecognized connection between the hypoxic response and carbon source in yeast.

TABLE 3

Genes known to be involved in the hypoxic response used to examine the hypoxic response across the strain panel

| Systematic Name | Gene Name | Description |
| --- | --- | --- |
| YBR085W | AAC3 | Mitochondrial ADP/ATP translocator |
| YBR301W | DAN3 | Cell wall mannoprotein |
| YEL047C | FRD1 | Fumarate reductase required for anaerobic growth |
| YEL049W | PAU2 | Seripauperin multigene family |
| YER011W | TIR1 | Cell wall mannoprotein |
| YFL020C | PAU5 | Seripauperin multigene family |
| YHR210C | YHR210C | Putative aldose 1-epimerase protein |
| YIL011W | TIR3 | Cell wall mannoprotein |
| YIL013C | PDR11 | Sterol transporter |
| YJR047C | ANB1 | Anaerobic translation elongation factor eIF-5A |
| YJR051W | OSM1 | Fumarate reductase required for anaerobic growth |
| YJR150C | DAN1 | Cell wall mannoprotein |
| YJR151C | DAN4 | Cell wall mannoprotein |
| YKL197C | PEX1 | AAA-peroxin that recycles peroxisomal targeting receptors under anaerobic conditions |
| YLL025W | PAU17 | Cell wall mannoprotein |
| YLR037C | PAU23 | Cell wall mannoprotein |
| YML083C | YML083C | Protein of unknown function |
| YOL161C | PAU20 | Seripauperin multigene family |
| YOR009W | TIR4 | Cell wall mannoprotein |
| YOR010C | TIR2 | Putative cell wall mannoprotein |
| YOR011W | AUS1 | Sterol transporter |

Connection Between AZFIp and Anaerobic Growth on Non-Preferred Sugars.

Figure 7:
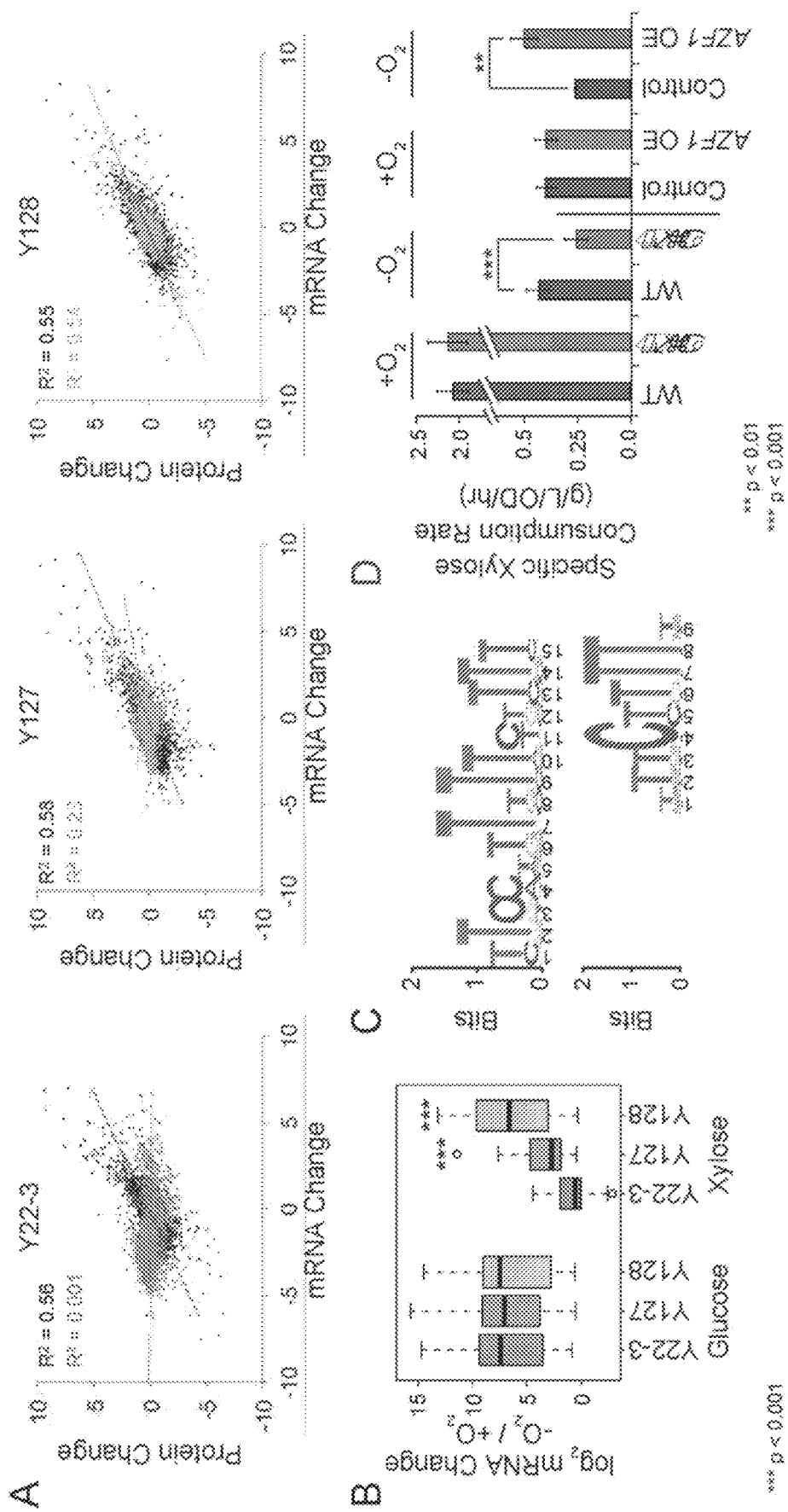
FIG. 7 illustrates the response to anaerobiosis in xylose-grown cells. A) Log 2(fold change) in mRNA and protein for cells grown.+-.O2, on glucose (black) or xylose, with linear fit (R2) listed. B) Expression of 21 classically defined hypoxic genes (Table 3). Asterisks indicate significant differences in mRNA change relative to Y22-3 (paired T-test). C) Identified promoter element (top) and known Azfl site (66) (bottom). D) Average (n=3) and standard deviation of xylose utilization rates in marker-rescued Y128 strains lacking or over-expressing (OE) AZF1 or harboring an empty vector ('Control'). Asterisks indicate significant differences as indicated (paired T-test).
Figure 12:
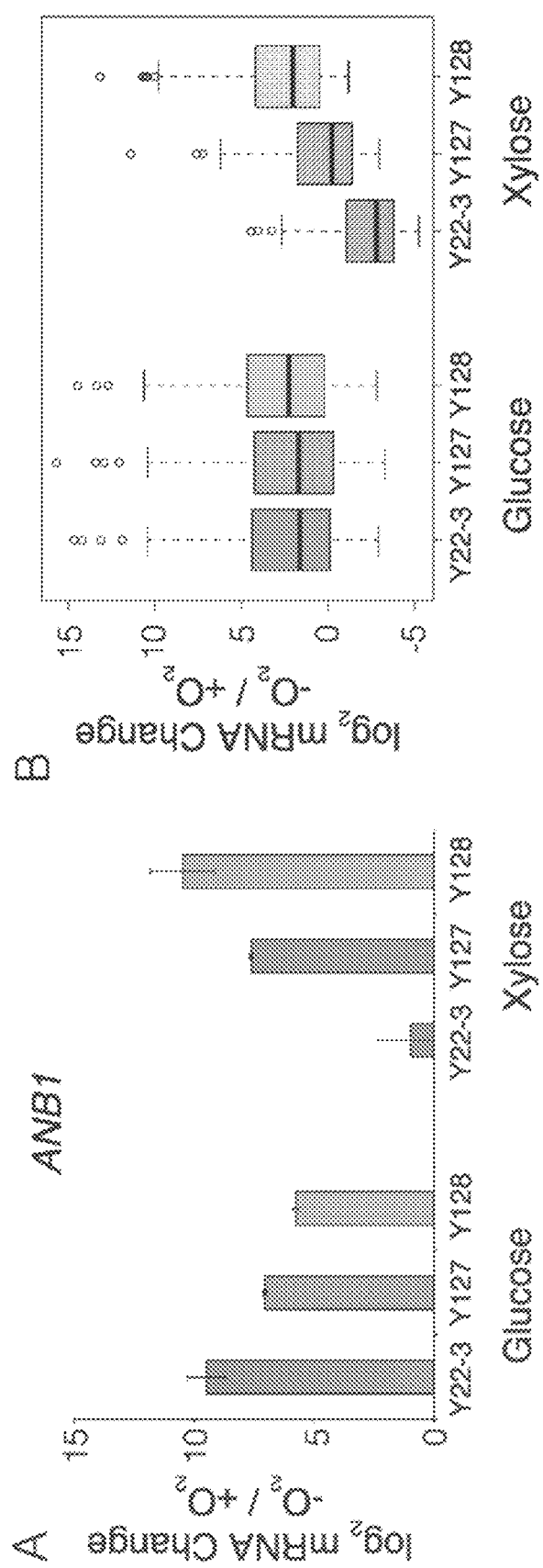
FIG. 12 illustrates transcriptome response to anaerobic xylose growth across the strain panel. A) Log 2(fold change) in abundance of ANB1 mRNA across all strains and growth conditions in response to anoxia. B) Log 2(fold change) in mRNA abundance of the 128 genes with a progressive increase anaerobic xylose induction, in Y22-3, Y127, and Y128 growing in glucose±O2 and xylose±O2.
Figure 13:
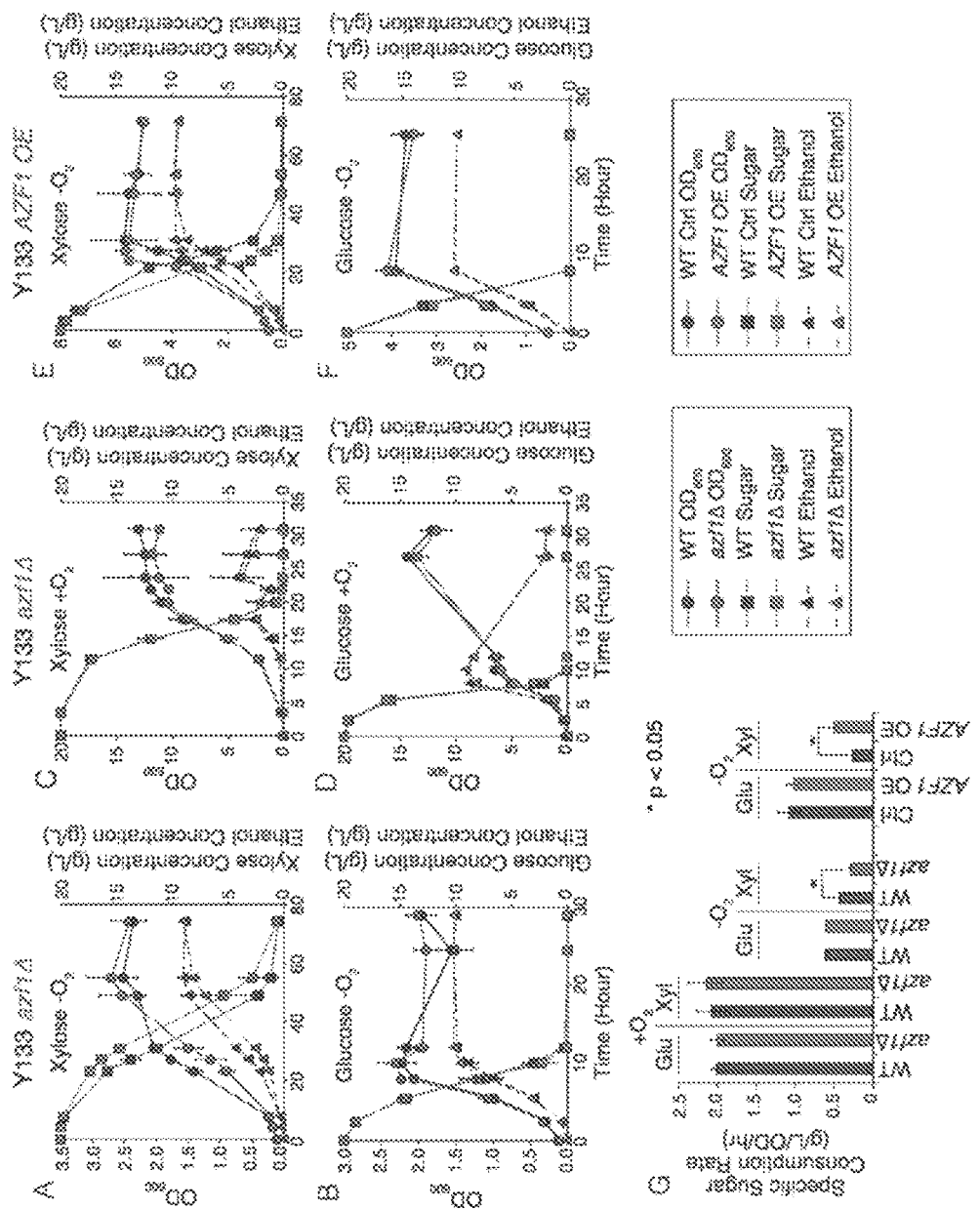
FIG. 13 illustrates deletion and over-expression of AZF1 influencing growth and fermentation under anaerobic xylose conditions. A-F) OD600 (circles), sugar concentration (squares), and ethanol concentration (triangles) for Y133 (marker-rescued Y128) azfl, Y133 AZF1 over-expression ("OE"), and Y133 wild type ("WT") or empty-vector control (black) for different sugars and growth conditions as indicated. G) Average (n=3) and standard deviation of sugar utilization rates from each strain during exponential growth. Asterisks indicate significant differences in sugar consumption rates as indicated (paired T-test).
Figure 14:
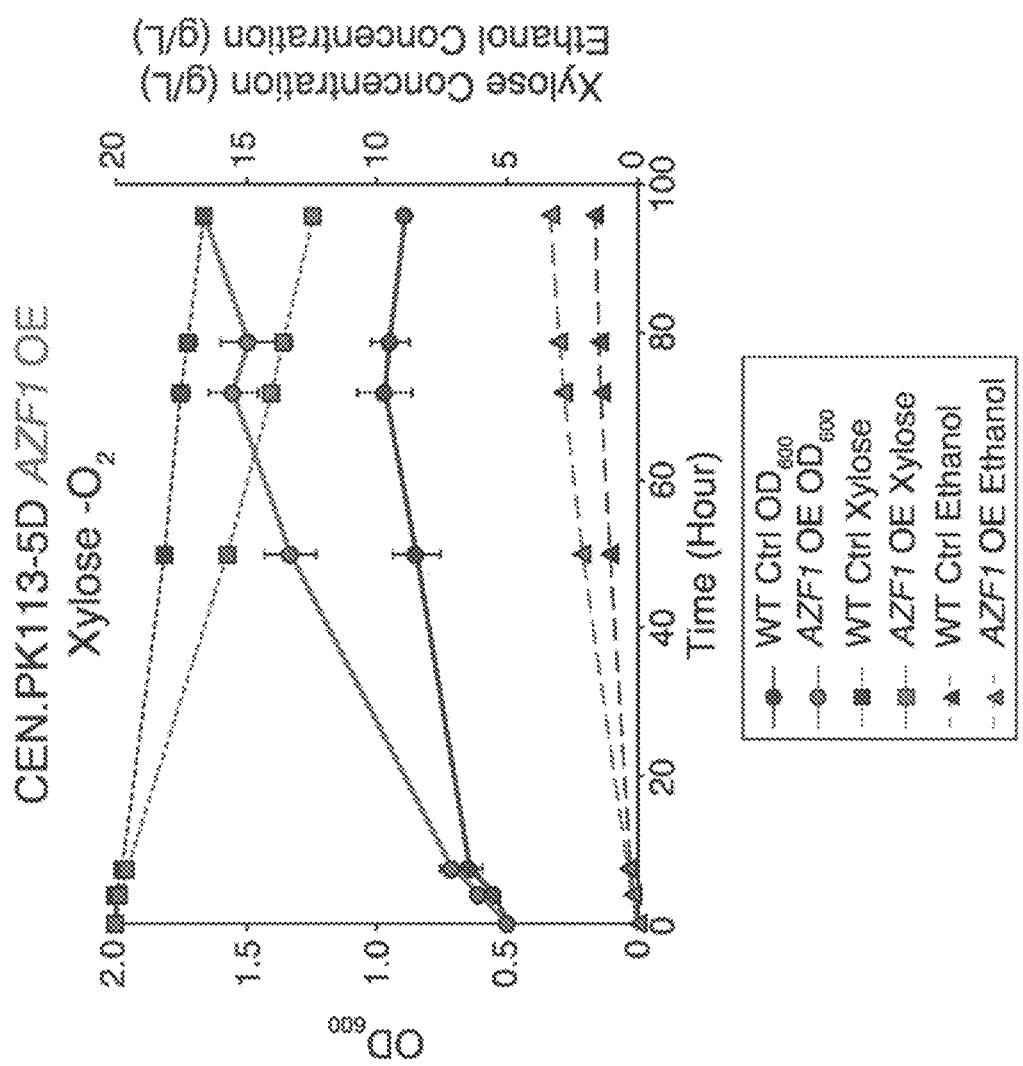
FIG. 14 illustrates AZF1 over-expression increasing xylose fermentation in a second strain background with Y128 mutations. OD600 (circles), xylose concentration (squares), and ethanol concentration (triangles) for CEN.PK113-5D with mutations required for xylose metabolism (HO::ScTAL1-Cpxy1A-SsXYL3-loxP-isu1 hog1 gre3 ira2 (7), Table 4) harboring the AZF1 over-expression plasmid or empty vector control (black).
Figure 15:
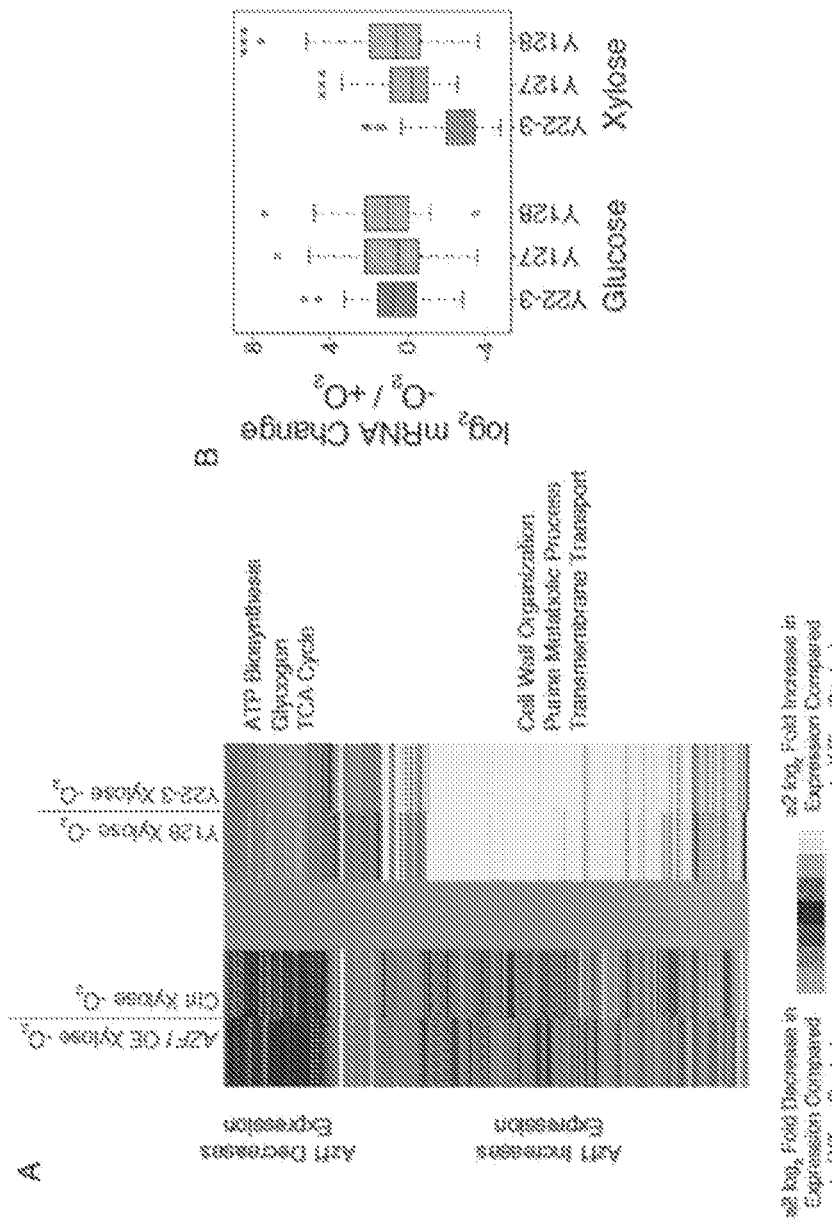
FIG. 15 illustrates transcriptomic analysis of AZF1 deletion and over-expression during anaerobic xylose fermentation. A) Clustering analysis of log 2(fold change) in mRNA for the 411 genes that show significant (FDR<0.05) effects in response to over-expression of AZF1 compared to controls and at least a 1.5 fold change in Y128 compared to Y22-3 grown anaerobically on xylose. Enriched functional groups (Bonferroni corrected p-value <0.05) for genes in each cluster are listed on the right. B) Log 2(fold change) in mRNA abundance for genes regulated by Mga2 in Y22-3, Y127, and Y128 cultured in glucose ±O2 or xylose ±O2. Asterisks indicate expression differences in each strain compared to Y22-3 (p<0.001, paired T-test).

To further investigate this effect, the inventors identified 128 genes that were induced progressively stronger across the strain panel when shifted to anaerobic xylose conditions, with a pattern similar to the hypoxic response (see FIG. 12B). These were enriched for genes involved in the hypoxic response, ergosterol biosynthesis, cysteine metabolism, and translation ($p<1\times10-4$, hypergeometric test). Promoter analysis identified tandem binding sites of Azf1, a transcription factor (TF) responsive to non-preferred sugars (FIG. 7C). Over half (68) of the 128 progressively induced genes harbored upstream Azf1 motifs ($p=5.7\times10-45$, hypergeometric test), including nearly all of the classical hypoxic genes. Indeed, over-expression of AZF1 increased rates of growth, xylose consumption, and ethanol production in Y128—but only when cells were grown on xylose and anaerobically (FIGS. 1D, 7). In contrast, deletion of AZF1 decreased growth and sugar fermentation, largely specific to anaerobic xylose growth (FIGS. 1D, 7). The Azf1 effect required at least some of the Y128 mutations, as it was observed in a different strain background recapitulating Y128 alleles (FIG. 14) but not in Y22-3.

Transcriptome Effects of AZF1 Deletion or Over-Expression.

Figure 8:
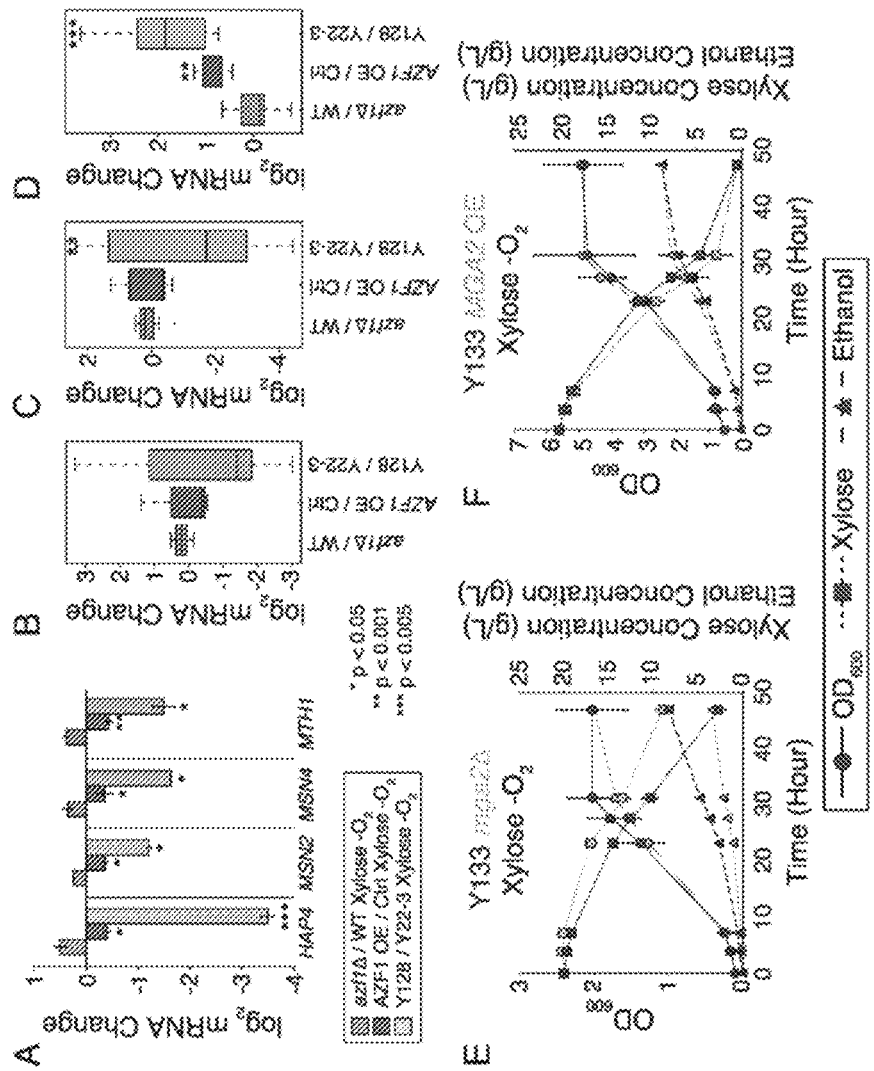
FIG. 8 illustrates Azfl and Mga2 regulated anaerobic xylose responses. A) Average log 2(fold change) in mRNA abundance of denoted genes as listed in the key. B-D) Distributions of log 2(fold change) in mRNA abundances for Hap4 (B), Msn2/Msn4 (C), and Mga2 (D) targets that are affected by AZF1 overexpression and show a corresponding change in Y128 versus controls. Asterisks indicate significant difference compared to azfl versus WT cells (paired T-test). E-F) OD600 (circles), xylose concentration (squares), and ethanol concentration (triangles) for strain Y133 (marker-rescued Y128) lacking (mga2, on the left) or over over-expressing ("OE", on the right) MGA2, and Y133 wild type ("WT") or empty-vector control (black) during anaerobic growth on xylose.
Figure 10:
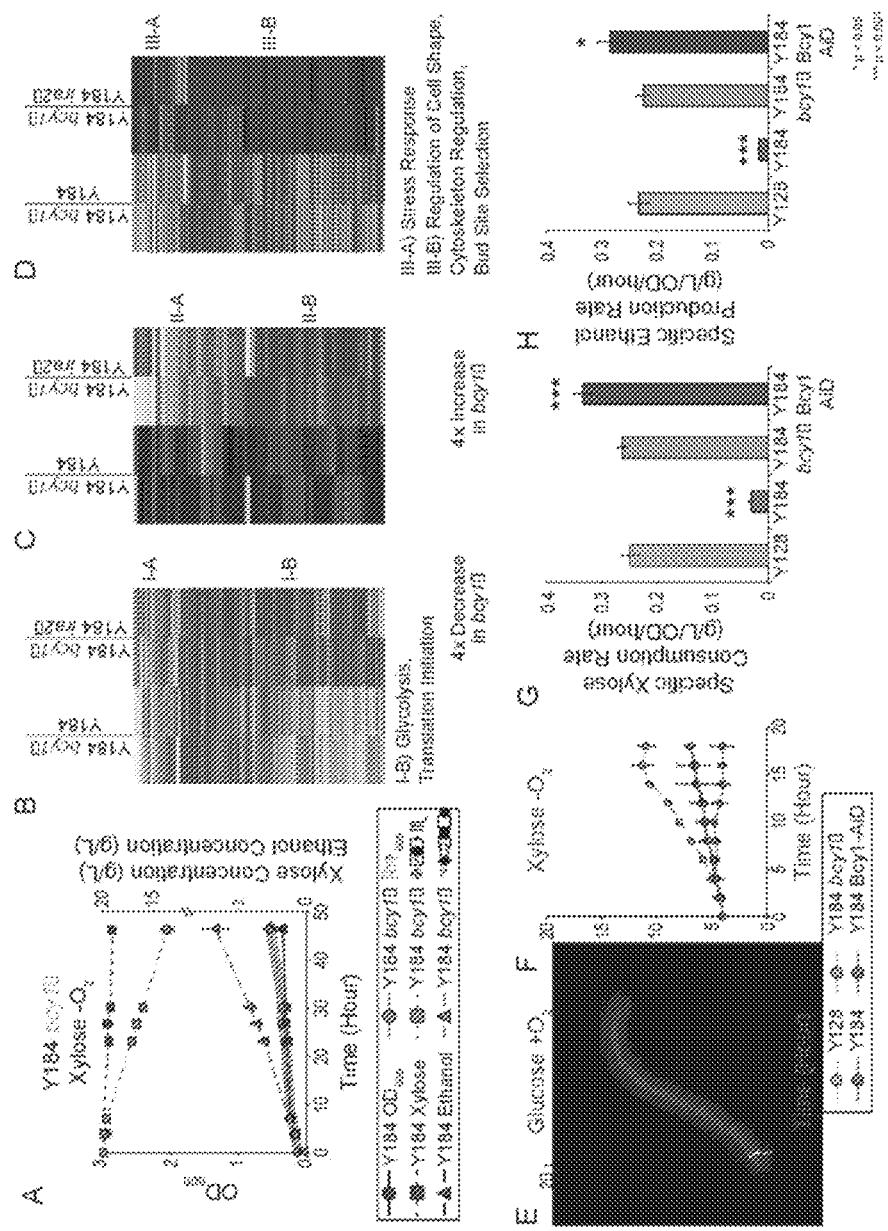
FIG. 10 illustrates mutation of BCY1 decoupling growth from anaerobic xylose metabolism. A) OD600 (circles), xylose concentration (squares), and ethanol concentration (triangles) for Y184 (Y22-3 gre3 isu1) (black) and Y184 bcy1 during anaerobic growth on xylose. B-D) Phospho-peptide changes in Y184 bcy1 relative to references, for phospho-peptides (rows) specific to Y184 bcy1 (B) or similar to Y184 (C) or Y184 ira2 (D). Functional enrichments for each denoted cluster are listed below each heat map. (E-F) Growth of strains in glucose+O2 (E) and xylose−O2 (F) as indicated in the key. (G-H) Average (n=3) specific xylose consumption (G) or ethanol production (H) rates. Asterisks indicate significant differences relative to Y128 (paired T-test).

The inventors identified transcriptome effects of AZF1 deletion or over-expression. AZF1 over-expression in particular had broad effects on the anaerobic-xylose transcriptome, affecting 411 genes (FDR<0.05) whose expression change also paralleled the difference in Y128 compared to Y22-3 grown anaerobically on xylose (FIG. 10A). The set of genes was enriched for those with a match to the Azf1 promoter motif ($p=3\times10-2$, hypergeometric test), supporting the regulatory role of Azf1. Among the affected genes were several TFs and their targets. For example, AZF1 over-expression led to reduced expression of HAP4 that regulates respiration genes as well as stress-responsive MSN2/MSN4, and targets of Hap4 ($p=1\times10-3$, hypergeometric test) and Msn2/Msn4 ($p=1\times10-20$) were enriched among repressed genes (FIG. 8A-8C); deletion of HAP4 and MSN4 were previously shown to improve xylose uptake. AZF1 also reduced expression of the gene encoding Mth1, which interacts with Rgt1 to repress hexose/xylose transporters (FIG. 8A); correspondingly, AZF1 over-expression induced several sugar transporters that can import xylose. In contrast, AZF1 production induced several targets of the TF Mga2 ($p=2\times10-3$) that responds to hypoxia to regulate genes involved in sterol and fatty acid metabolism (FIG. 8D)—this was intriguing given that defects in the hypoxic response led the inventors to Azf1. To test its importance in anaerobic xylose consumption, the inventors perturbed MGA2 expression directly. Indeed, MGA2 deletion decreased the rate of anaerobic xylose fermentation while MGA2 over-expression improved it (FIG. 8E-8F). These results show that the sugar-responsive Azf1 and the oxygen-responsive Mga2 play important roles in mediating anaerobic xylose fermentation in Y128.

Upstream Regulatory Network that Mediates the Downstream Response, Including Activation of Azf1 and Mga2 Targets.

The inventors profiled the phosphoproteomes of Y22-3, Y127, and Y128 cultured on xylose with or without oxygen and then applied a novel network approach to infer regulation of strain-specific phosphorylation differences. Because many kinases recognize specific sequences around the phosphorylation site, the inventors identified 'modules' of phospho-peptides that are likely co-regulated and then implicated kinases and phosphatases that may control their phosphorylation change.

First, the inventors grouped peptides based on their changes in phosphorylation when each strain was shifted from aerobic to anaerobic xylose conditions, identifying peptides with progressive phosphorylation increases or decreases across the strain panel ("Class A" increases or decreases) and peptides with responses uniquely higher or lower in Y128 ("Class B" increases or decreases).

Next, the inventors partitioned each group into 'modules' of peptides that harbor similar sequences around the phosphorylated site ('phospho-motifs'). Module peptides therefore share the same phosphorylation pattern and similar phospho-motifs, and thus are enriched for peptides that are likely co-regulated.

Reasoning that module peptides are regulated by the same upstream regulator(s), the inventors then searched a background network of protein interactions for proteins that physically interact with more module peptides than expected by chance (FDR<0.05). The inventors focused on kinases whose phosphorylation preference matches the module phospho-motif, thereby implicating those kinases as direct regulators of module peptides.

Figure 9:
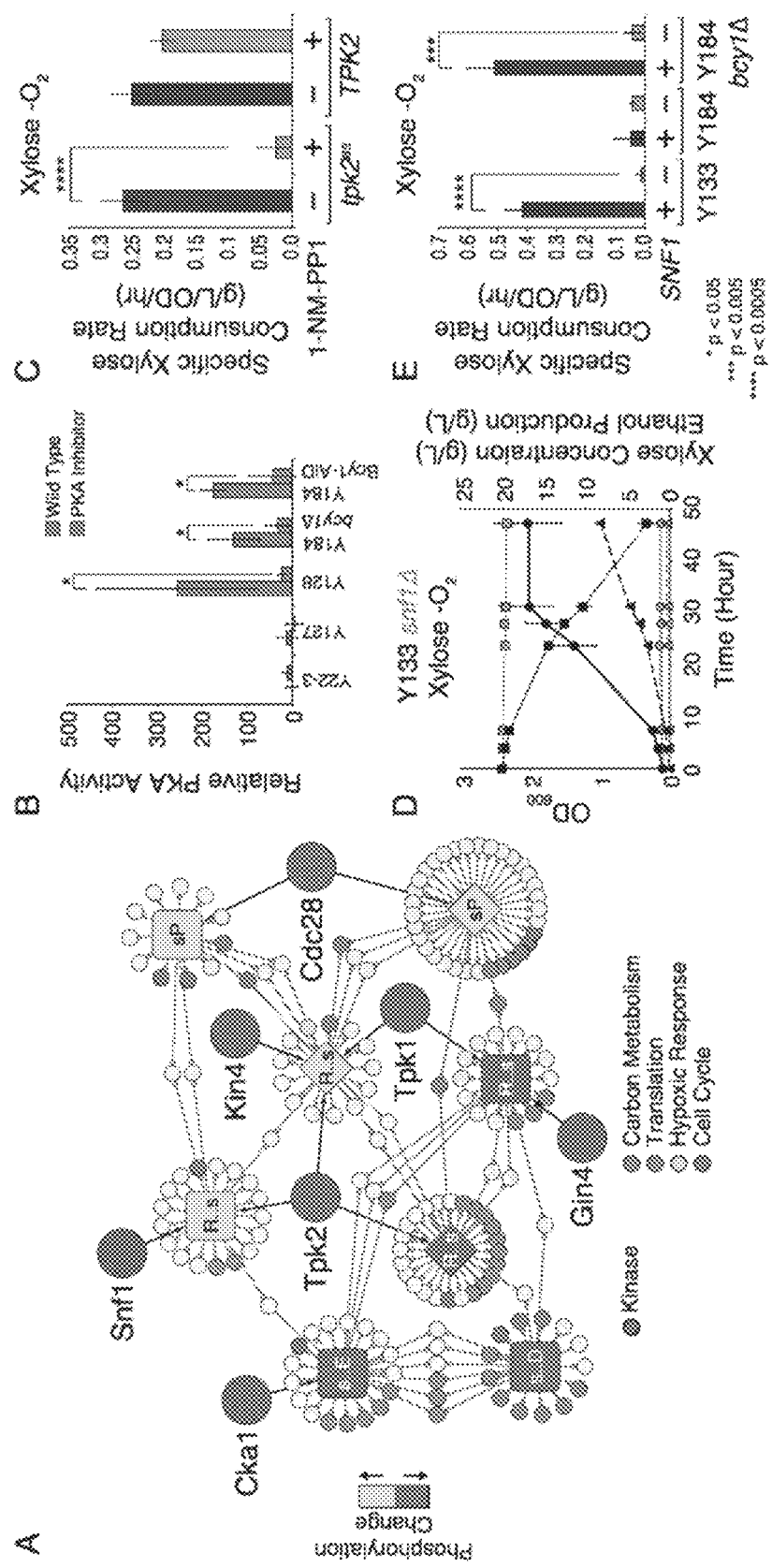
FIG. 9 illustrates an inferred network regulating phosphorylation changes during anaerobic xylose growth. A) Modules of peptides are shaped and colored according to class (Class A, diamond; Class B, square) and increase or decrease of phosphorylation change across the strain panel. Each module is labeled with the phospho-motif sequence, with small case letter representing the phosphorylated site and ". . ." indicating non-specific residues. Implicated kinase regulators are shown as purple circles; proteins whose peptides belong to each module are shown as smaller circles, coded by protein function as listed in the key. Note that proteins with multiple phospho-sites can belong to multiple modules. B) Average (n=3) and standard deviation of the relative in vitro phosphorylation of a PKA substrate for lysates from cells that can (Y128, Y184 bcy1, Y184 Bcy1-AiD) or cannot (Y22-3, Y127) use xylose anaerobically. Grey bars represent phosphorylation in the presence of PKA inhibitor H-89. C) Average (n=3) and standard deviation of sugar utilization rates for Y133 tpk1 tpk3 tpk2 as or Y133 tpk1 tpk3 TPK2 during anaerobic growth, in the presence or absence (black) of 1-NM-PP1. D) OD600 (circles), xylose concentration (squares), and ethanol concentration (triangles) for WT (black) or snf1 Y133 (marker-rescued Y128) grown in xylose −O2. E) Average (n=3) and standard deviation of xylose utilization rates. Asterisks indicate significant differences according to the key (paired T-tests).

The resulting network implicated several regulators in the anaerobic xylose response (FIG. 9A). Peptides that showed highest phosphorylation levels in Y22-3 upon anaerobic xylose shift included ribosomal proteins and translation factors, whose modules were associated with PKA subunit Tpk2 and Cka1 of the CK2 kinase, which phosphorylates translation factors in other organisms to modulate translation. Other modules showed increased phosphorylation in Y128 shifted to anaerobic xylose conditions, including those connected to cyclin-dependent kinase Cdc28 that regulates carbon-metabolism enzymes and proteins required for division.

Modules Connected to PKA Subunits Tpk1 and Tpk2.

Figure 16:
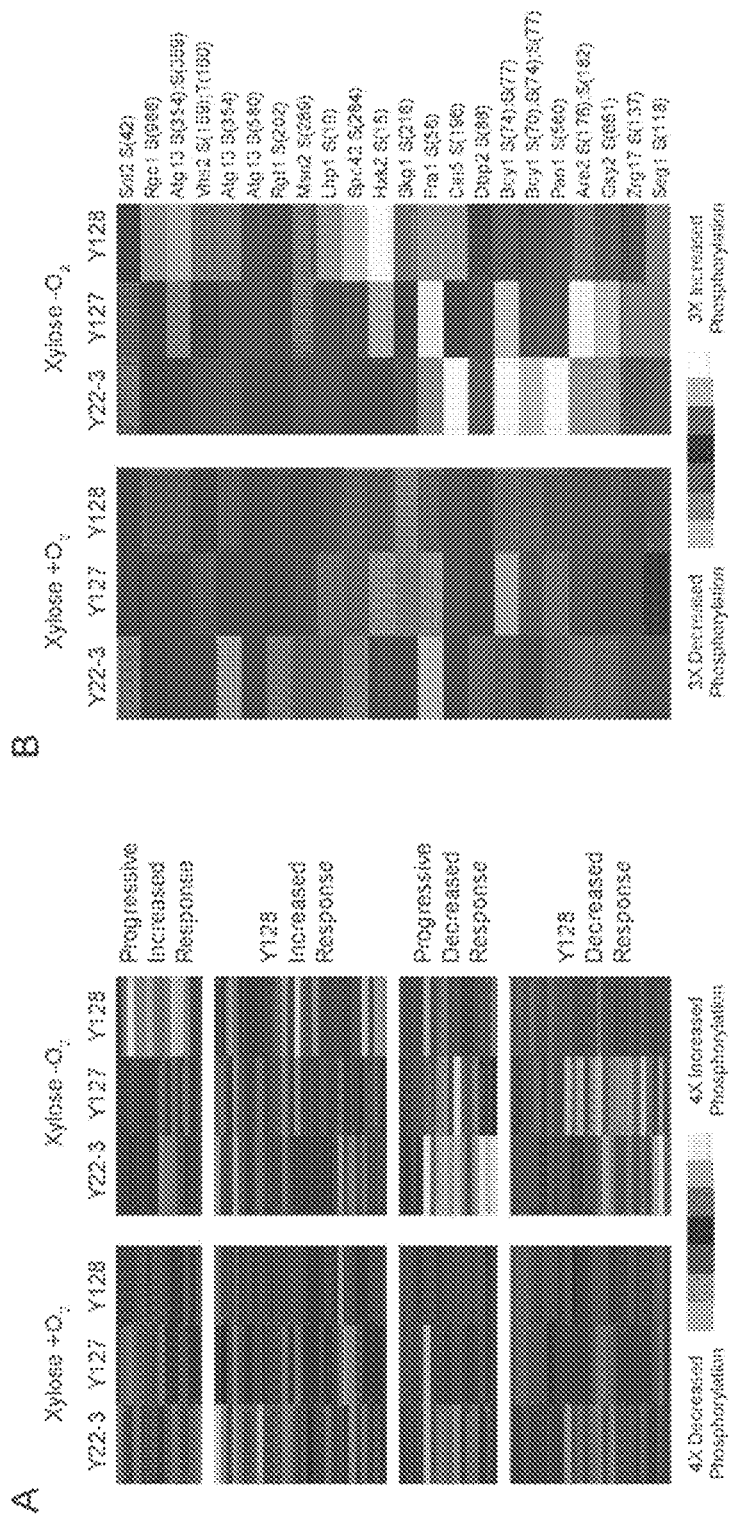
FIG. 16 illustrates relative phosphorylation differences for known and inferred PKA targets across the strains growing anaerobically in xylose. Heat map represents relative abundance of phospho-peptides across the panel. Each row represents a phospho-peptide as measured in strains (columns) grown in xylose with (left) and without oxygen (right). Data represent average phospho-peptide abundance relative to the mean abundance across all six data points, such that yellow indicates phospho-peptide abundance above the mean and blue indicates phospho-peptide abundance below the mean, according to the key. A) Shown are all phospho-peptides in FIG. 9A that harbor an RxxS phospho-motif and fall into different categories, including Class A (progressive increase/decrease) and Class B (Y128-specific response). B) Shown are 22 sites from panel A that are known PKA target sites identified in the KID database. Protein name and phospho-site(s) are indicated for each row. Notably, some known PKA sites show increases in phosphorylation while others show decreases in phosphorylation in Y128 grown in xylose −O2.
Figure 17:
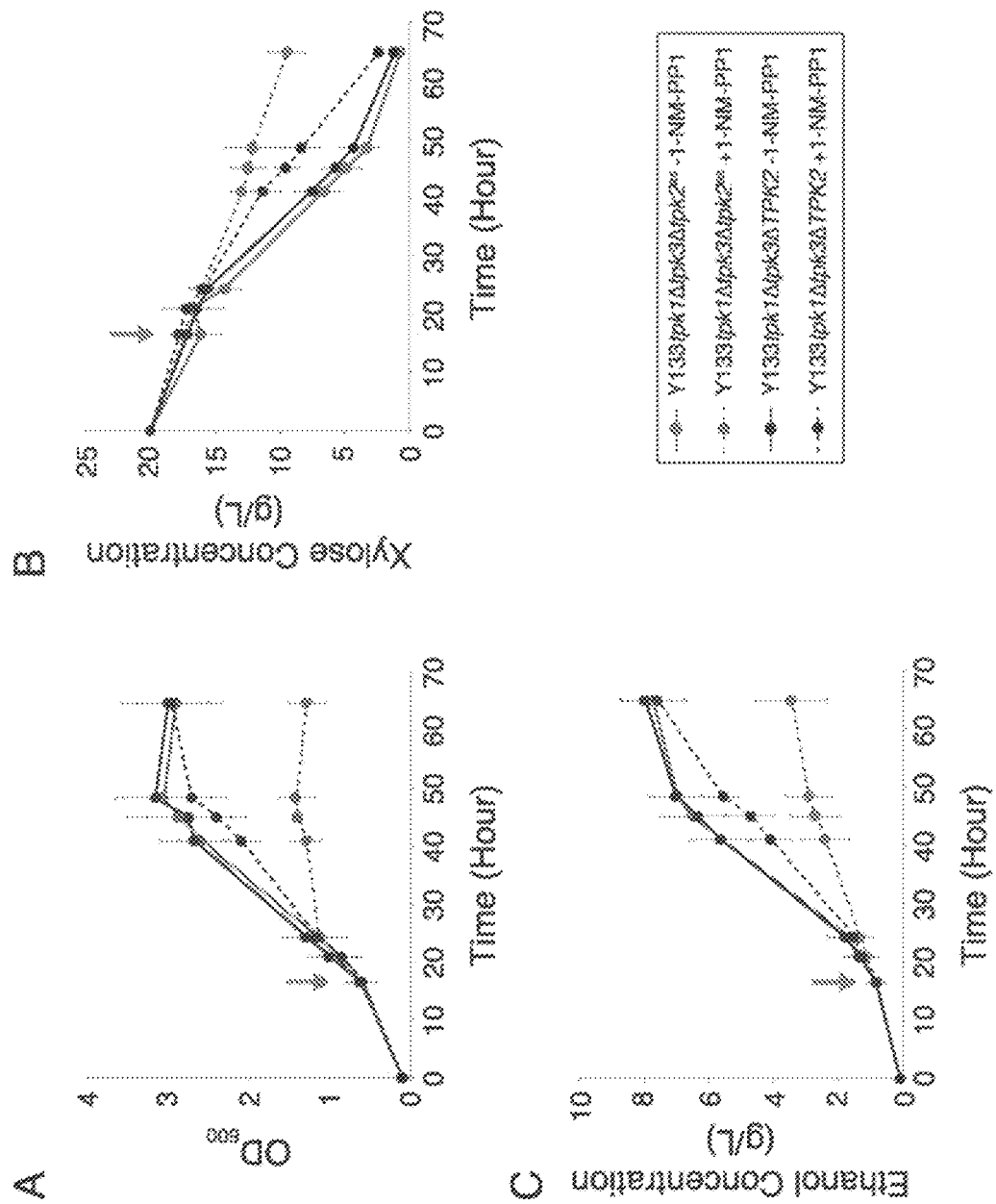
FIG. 17 illustrates addition of 1-NM-PP1 inhibiting anaerobic growth and xylose fermentation of tpkas strain. OD600 (A), xylose concentration (B), and ethanol concentration (C) for Y133tpk1 tpk3 tpk2as or Y133tpk1 tpk3 TPK2 (black) in the presence of 10.mu.M 1-NM-PP1 (dashed line) or DMSO control (solid line). Timing of 1-NM-PP1 or DMSO addition is indicated by an arrow.

The inventors were intrigued by multiple modules connected to PKA subunits Tpk1 and Tpk2, since mutations in IRA2 are predicted to up-regulate RAS/PKA signaling. Two PKA-associated modules showed reduced phosphorylation in Y128, spanning translation factors described above—indeed, the proteins whose peptides belong to these two modules are enriched for known targets of PKA (p=3×10-3), implicating the other peptides as potential PKA targets. But two other modules of peptides showed increased phosphorylation in xylose-grown Y128 shifted to anaerobic conditions (FIG. 9A). These modules included known PKA targets and phospho-sites (FIG. 16) such as hexokinase 2 that promotes glycolytic flux and stress-responsive TF Msn2 that is inhibited by PKA phosphorylation. Intriguingly, this module also included hypoxia-responsive Mga2 at a site that matches the known PKA specificity. MGA2 genetically interacts with IRA2 in high-throughput datasets, supporting a link between PKA and MGA2 function. Furthermore, Mga2 targets are significantly up-regulated in Y128 that lacks functional IRA2 compared to nonfermenting strains (FIG. 10B).

Implication of Increased PKA Activity in Y128.

Figure 11:
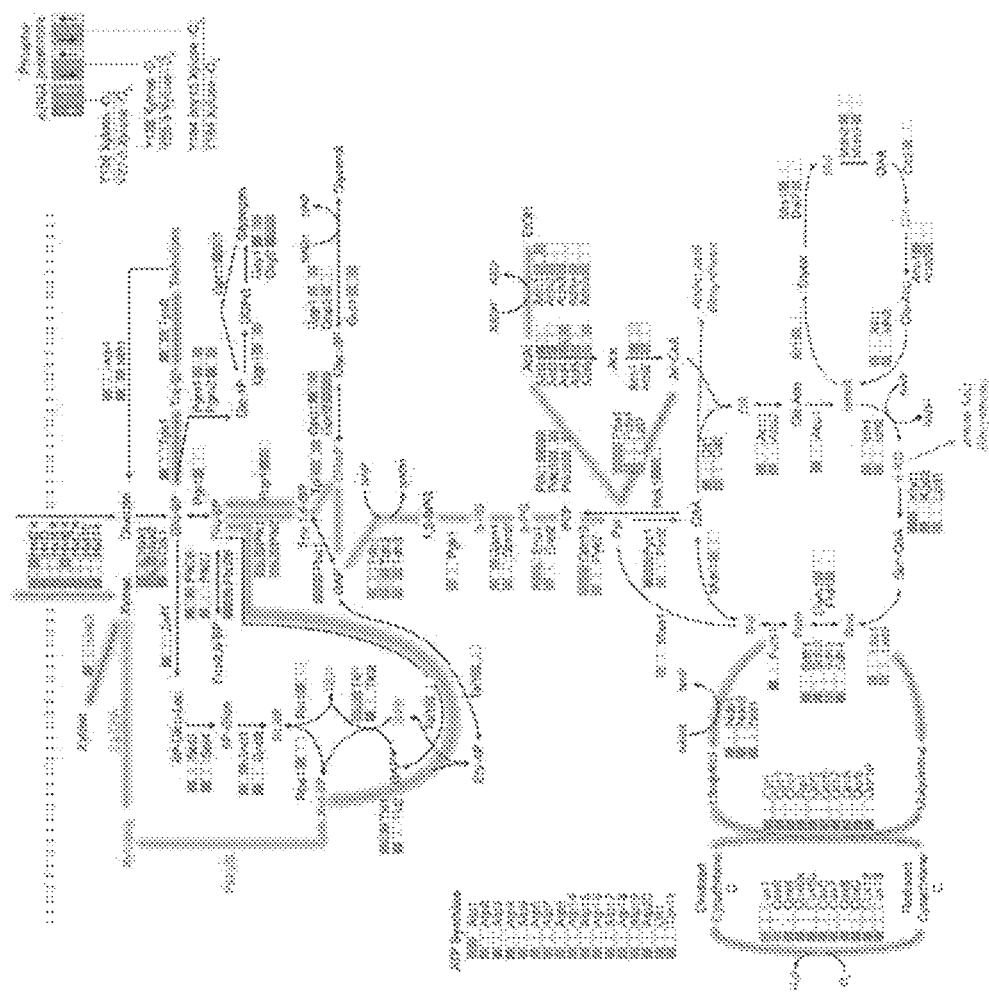
FIG. 11 illustrates an integrative model incorporating transcript, phospho-protein, and metabolite changes across the strain panel. Map of central carbon metabolism. Each step is annotated with boxes indicating mRNA difference (left) or phosphorylation difference (middle) in Y128 versus Y22-3, or phosphorylation difference (right) in Y184 bcy1 versus Y184 grown anaerobically on xylose, according to the key. Gray indicates no significant change, white represents missing data, and other boxes indicate multiple phospho-sites with different changes. Metabolites measured previously are colored to indicate an increase or decrease in abundance in Y128 versus Y22-3 grown anaerobically on xylose. Reactions predicted to be active or suppressed in xylose fermenting strains based on mRNA, protein, and/or metabolite abundances are highlighted. Hexose transporters marked with a star have been implicated in xylose transport.
Figure 18:
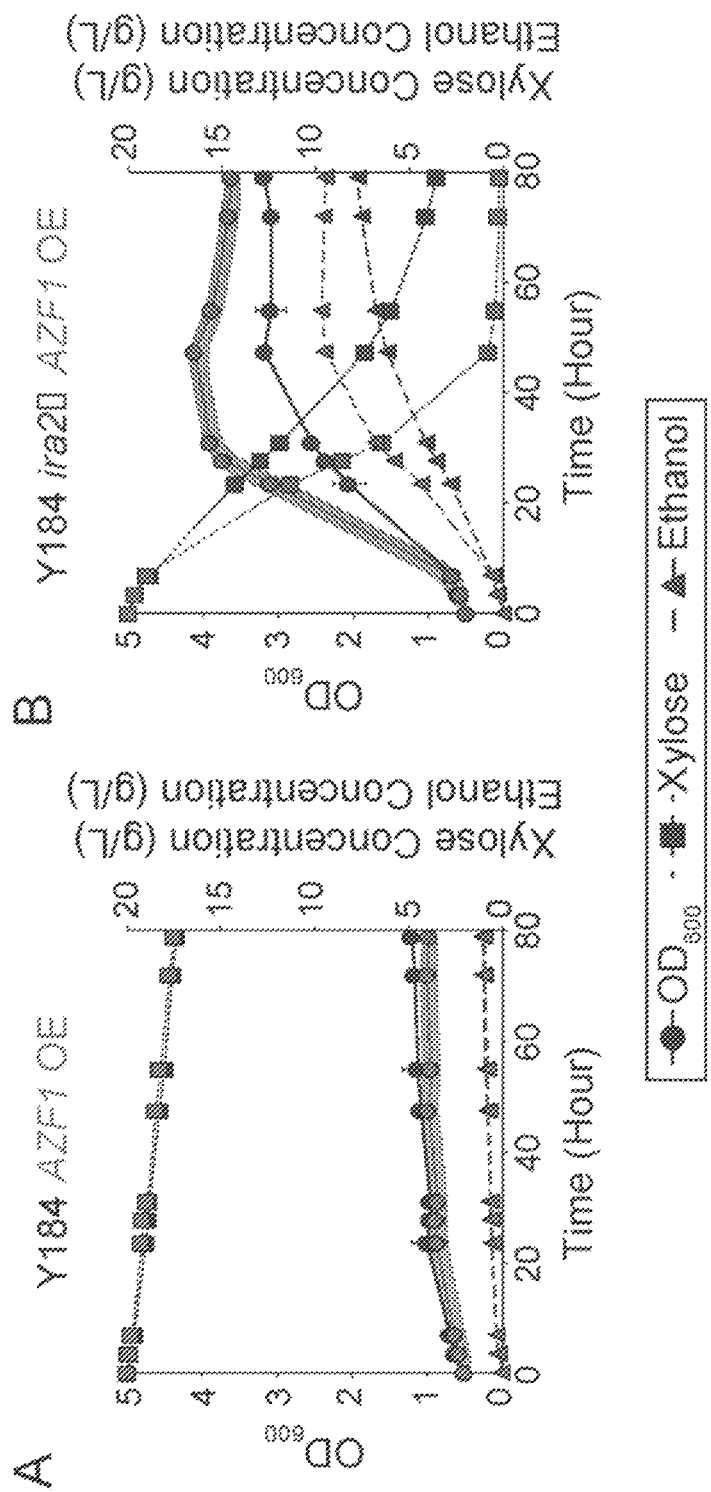
FIG. 18 illustrates anaerobic xylose utilization and Azfl influence dependent on deletion of IRA2. A) OD600 (circles), xylose concentration (squares), and ethanol concentration (triangles) for Y184 (Y22-3 gre3 isu1) AZF1 over-expression ("OE") or Y184 empty-vector control (black). OD600 measurements for Y184 AZF1 OE highlighted in yellow. B) OD600 (circles), xylose concentration (squares), and ethanol concentration (triangles) for Y184 ira2 AZF1 over-expression ("OE") or Y184 ira2 empty-vector control (black). OD600 measurements for Y184 ira2 AZF1 OE highlighted in yellow.

The inventors tested the implication of increased PKA activity in Y128 in several ways. First, lysate from Y128 grown anaerobically on xylose showed increased phosphorylation of a PKA substrate in vitro compared to the other two strains, which was blocked by PKA inhibitor H-89 (FIG. 9B). Second, Y128 harboring a single analog-sensitive allele of PKA subunits (tpk2as) required PKA function for both growth on and fermentation of xylose: inhibition of tpk2as activity via addition of the inhibitor 1-NM-PP1 rapidly inhibited growth and fermentation during anaerobic xylose utilization (FIG. 3C, 11). Third, the beneficial effects of AZF1 over-expression required deletion of IRA2 (FIG. 18). Together, these results show that RAS/PKA activity is required for anaerobic xylose fermentation in Y128, even though some proteins known to be regulated by PKA show decreased phosphorylation in these conditions (FIG. 11B and below).

PKA Activity and SNF1 are required for Anaerobic Xylose Utilization in Y128.

Figure 19:
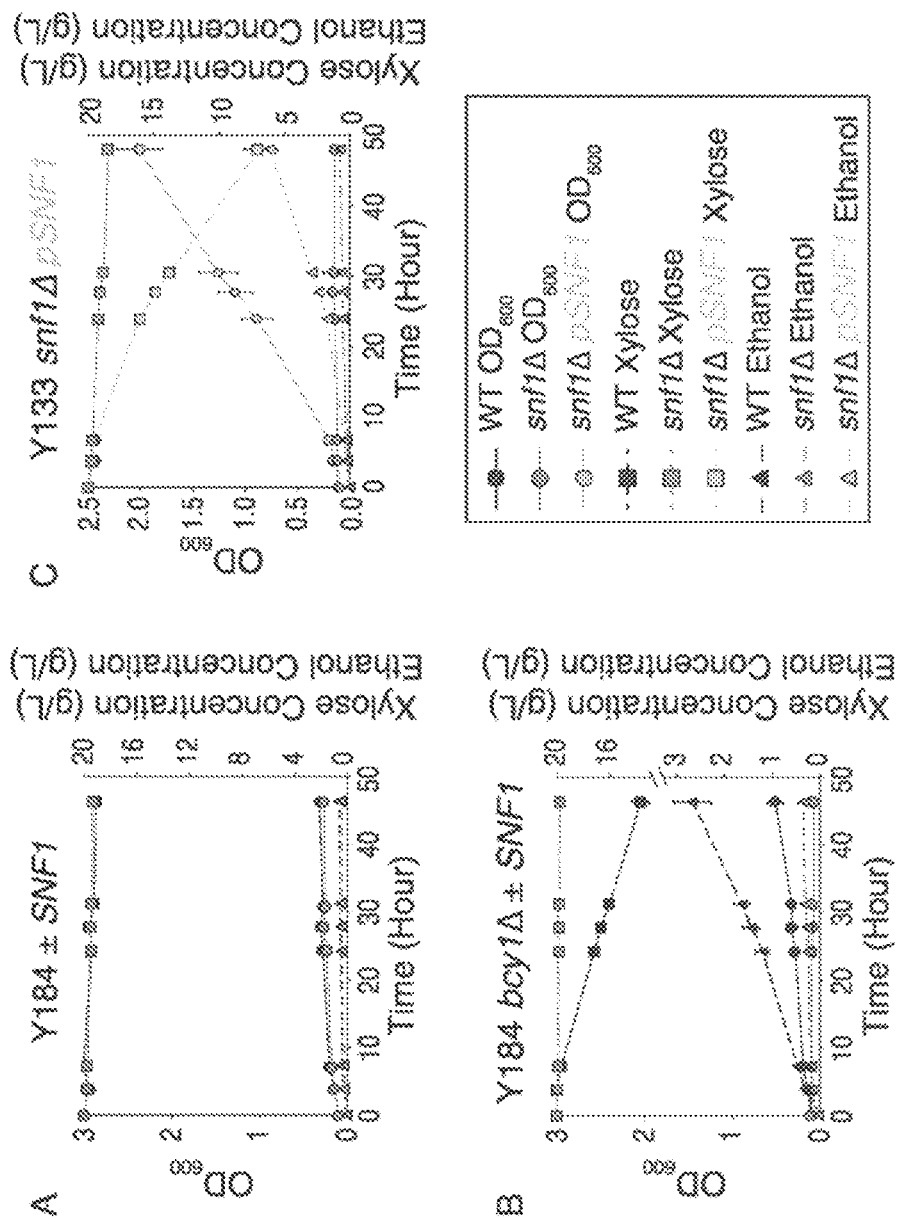
FIG. 19 illustrates SNF1 required for anaerobic xylose fermentation. A-B) OD600 (circles), xylose concentration (squares), and ethanol concentration (triangles) for Y184 (Y22-3 gre3 isu1).+−.SNF1 and Y184 bcy1.+−.SNF1 grown in xylose −O2. SNF1+ strains are plotted in black and snf1 strains are plotted in orange. C) OD600 (circles), xylose concentration (squares), and ethanol concentration (triangles) in Y133 snf1 complemented with pSNF1 Moby 2.0 plasmid (black) and pEMPTY control vector (67) for cells grown anaerobically in xylose. The results show that Snf1 is essential for anaerobic xylose fermentation.

One of the Tpk2-connected modules of phosphorylated peptides was also associated with the Snf1 kinase, which is activated by low cellular energy to induce alternative-carbon utilization genes. This was interesting, because PKA and Snf1 are not normally active under the same conditions—the two regulators can produce antagonistic effects and even inhibit each other's activity. To test this network prediction, the inventors knocked out SNF1 from Y128 and measured xylose fermentation capabilities. Indeed, SNF1 is essential (but insufficient in the absence of other Y128 mutations) for anaerobic xylose utilization in Y128 (FIG. 9D-9E, 19). Thus, PKA activity and SNF1 are required for the effect, validating the network predictions.

BCY1 Deletion Enabled Rapid Xylose Fermentation but in the Absence of Growth.

Figure 20:
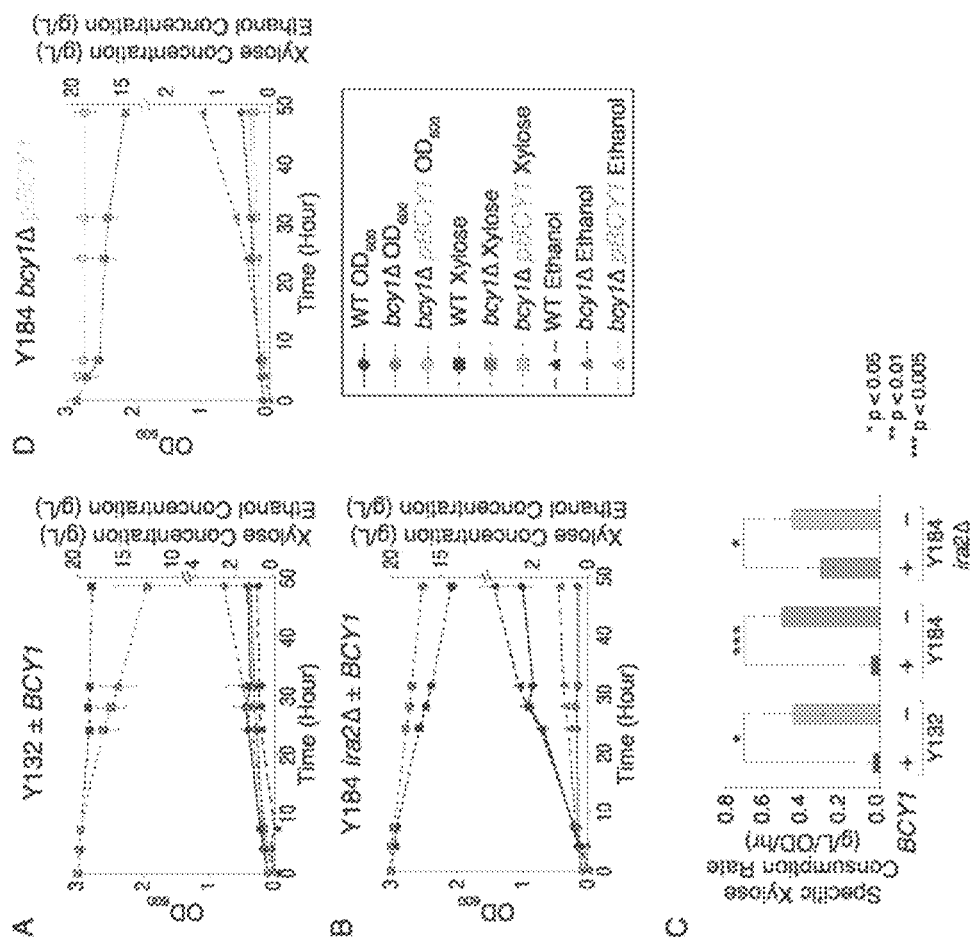
FIG. 20 illustrates deletion of BCY1 influencing anaerobic xylose fermentation. A-B) OD600 (circles), xylose concentration (squares), and ethanol concentration (triangles) for Y132 (marker-rescued Y127).+−.BCY1 (A) and Y184 ira2 BCY1 (B) during growth in xylose −O 2. BCY1+ strains are in black and bcy1 strains are in grey. C) Average (n=3) and standard deviation of sugar utilization rates are shown for each strain.+−.BCY1. Asterisks indicate significant differences (paired T-test) as indicated. D) OD600 (circles), xylose concentration (squares), and ethanol concentration (triangles) in Y184 bcy1 complemented with pBCY1 Moby 2.0 plasmid (67) and pEMPTY control vector (67) for cells grown anaerobically in xylose.

Deletion of IRA2 upregulates PKA as well as other downstream effects of RAS. To distinguish if inducing PKA alone is enough to mediate the response, the inventors deleted the PKA negative regulatory subunit BCY1 in strain Y184 (Y22-3 gre3 isu1) that can use xylose aerobically but not anaerobically. Y184 lacking BCY1 could not grow anaerobically on xylose, as seen for other non-preferred carbon sources—but surprisingly the cells rapidly fermented xylose despite growth arrest, at rates and ethanol yields surpassing other published xylose-converting strains (FIG. 10A, 20, Table 2). Xylose fermentation by the Y184 bcy1 was associated with increased PKA activity, since lysate from Y184 bcy1 cells grown anaerobically on xylose showed increased phosphorylation of a PKA target that was blocked by the H-89 PKA inhibitor (FIG. 9B). Thus, up-regulating PKA activity through BCY1 deletion enabled rapid xylose fermentation but in the absence of growth.

Distinguish Phosphorylation Events Related to Growth Versus Metabolism.

Figure 21:
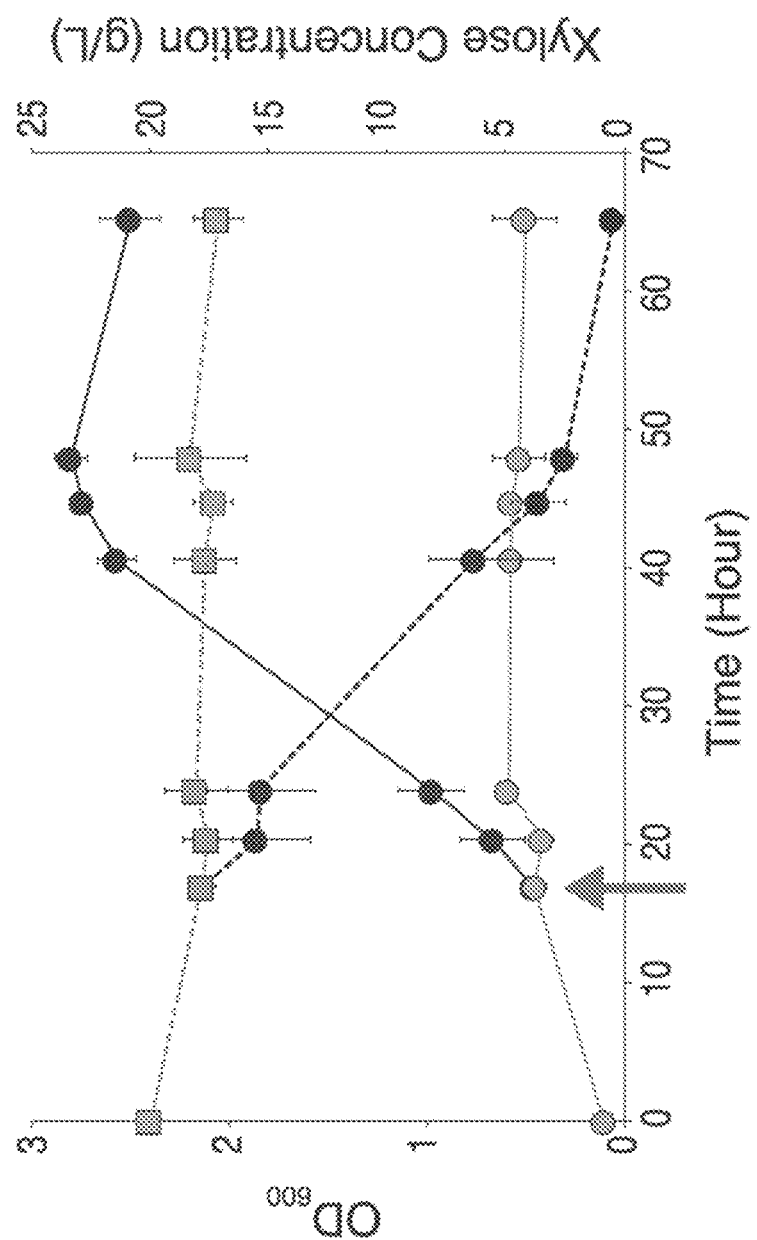
FIG. 21 illustrates the inhibition of growth does not promote anaerobic xylose utilization. OD600 (circles) and xylose concentration (squares) for Y128 in the absence (black) and presence of 400 mM hydroxyurea, added at the time point indicated by the arrow, during anaerobic growth on xylose. Addition of hydroxyurea inhibits growth of Y128, but does not promote anaerobic xylose utilization.

The unique phenotype of the Y184 bcy1 strain provided an opportunity to distinguish phosphorylation events related to growth versus metabolism. Phosphorylation patterns shared between Y184 and Y184 bcy1, neither of which can grow anaerobically on xylose, are therefore associated with growth arrest; in contrast, phosphorylation patterns common to Y184 bcy1 and Y184 ira2, which share the ability to ferment xylose anaerobically but differ in growth capabilities, are implicated in xylose metabolism (FIG. 10B-10D). The 210 peptides whose phosphorylation levels were unique to Y184 bcy1 or shared between non-growing strains occurred on proteins involved in translation, ribosome biogenesis, nucleotide biosynthesis (including ribonucleotide reductase Rnr2), and DNA replication—all functions required for division. These phosphorylation patterns are likely an indirect consequence of arrest; notably, arresting Y128 growth with the RNR inhibitor hydroxyurea blocked both growth and anaerobic xylose utilization (FIG. 21). In contrast, many of the 335 phosphorylation patterns unique to Y184 bcy1 or shared between the two xylose-fermenting strains were linked to metabolism, including on hexose transporters Hxt2 and Hxt6 that influence xylose uptake, enzymes involved in glycolysis (Pfk2, Fbp26, Tdh1/2, Cdc19, Pda1, Pdc1), trehalose biosynthesis that regulates glycolytic overflow (Tsl1, Tps2, Tps3, Nth2), and glycerol and alcohol dehydrogenases that recycle NADH during high glycolytic flux (Gpd1, Gut1, Adh1).

Several phosphorylation patterns implicated in Y128 (FIG. 9A) were not recapitulated in the Y184 bcy1 strain, suggesting that they are not strictly required for anaerobic xylose fermentation. For example, unlike Y128, phosphorylation of known Cdc28 targets was reduced in Y184 bcy1 compared to Y184 ira2, strongly suggesting that Cdc28-dependent phosphorylation in Y128 is linked to division and not xylose metabolism. Despite increased PKA signaling in the bcy1 strain (FIG. 9B), several of the known and predicted PKA phosphorylation sites in Y128 showed reduced phosphorylation upon BCY1 deletion. For example, relative to Y128, Y184 bcy1 showed decreased phosphorylation of serine 15 (S15) on the main hexokinase, Hxk2, whose phosphorylation normally increases activity. Finally, the Y184 bcy1 strain displayed several unique phosphorylation patterns not observed in the other strains. Remarkably, this included decreased phosphorylation on Hog1 activating site T174, a phenotype seen when Hog1 activity is reduced. This suggests that effects of BCY1 deletion mimic Hog1 inactivation that enhances xylose consumption, and raises the possibility that PKA activity can suppress Hog1 activation.

Figure 22:
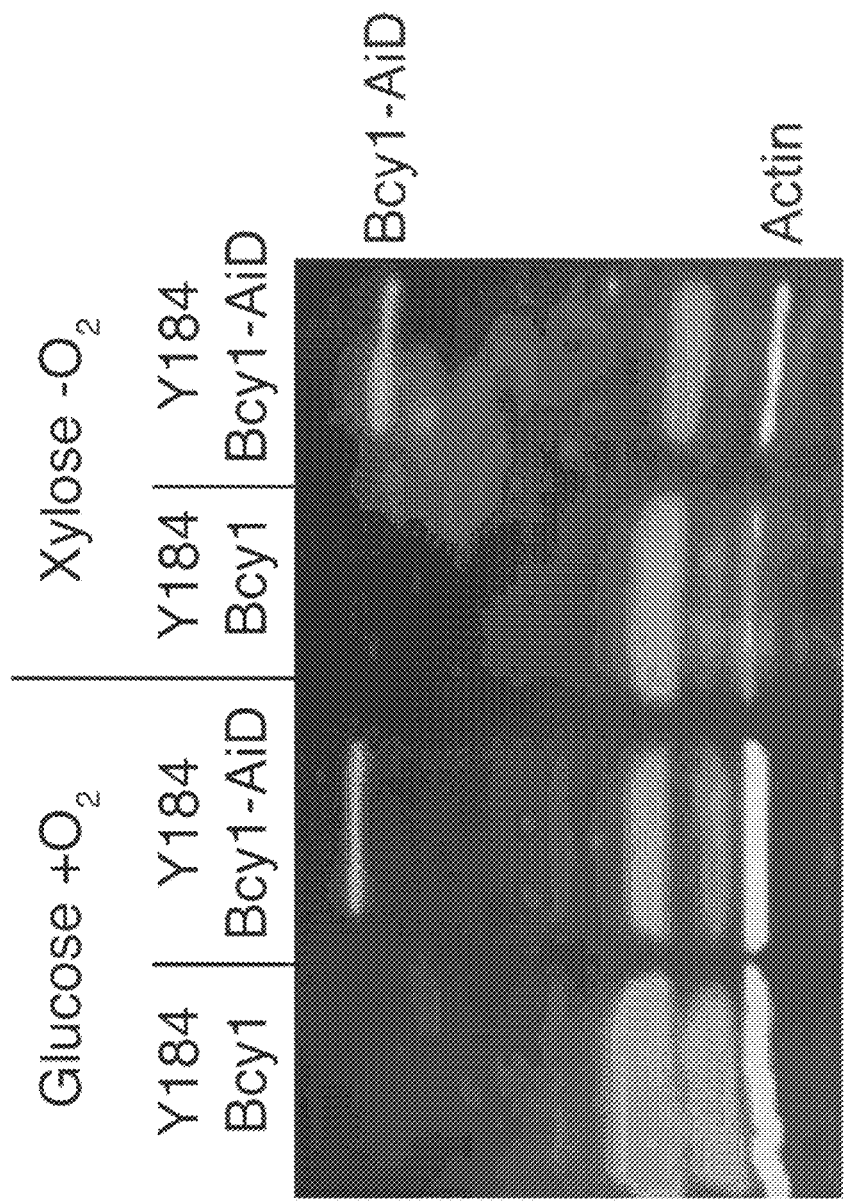
FIG. 22 illustrates Bcy1-AiD stable in both glucose +O2 and xylose −O2. Western blot analysis of Bcy1-AiD using anti-FLAG antibody from cultures grown in glucose +O2 or xylose −O2 in Y184 with WT Bcy1 and Y184 with Bcy1-AiD. Anti-actin antibody was used as a loading control.

Although BCY1 deletion enhances anaerobic xylose metabolism, it slows aerobic growth on glucose, which is a problem for industrial propagation of microbial cells. As a proof-of-principle for industrial use, the inventors therefore generated a tagged version of Bcy1 in attempt to enable auxin-dependent degradation and made an important discovery: simply fusing a peptide to the carboxyl-terminus of Bcy1 (without enabling degradation) was enough to combine the benefits of BCY1+ and bcy1 strains in aerobic and anaerobic conditions, respectively (FIG. 10E-H). When grown aerobically on glucose to mimic industrial propagation, cells expressing a Bcy1-AID fusion (but without auxin-regulated controllers) grew to higher cell titers than Y128, consistent with functional Bcy1 activity (FIG. 10E). But when shifted at high density to anaerobic xylose conditions, the strain dramatically reduced growth and rapidly fermented xylose to ethanol, mimicking the bcy1 strain (FIG. 10F-10H, Table 2). The Bcy1 protein fusion remained readily detectible by Western blot, indicating that the recapitulation of the bcy1 phenotype was not through Bcy1 degradation (FIG. 22). The inventors propose that perturbing Bcy1 function through protein fusion serves to redirect PKA signaling toward different sets of targets.

Phosphoproteomics in Y184 bcy1 Implicates Responses Involved in Growth Versus Metabolism.

The inventors compared phosphoproteomic data among three strains cultured anaerobically on xylose: Y184 (Y22-3 gre3 isu1) that can neither grow on nor metabolize xylose, Y184 ira2 (Y22-3 gre3 isu1 ira2) that both grows on and metabolizes xylose, and Y184 bcy1 (Y22-3 gre3 isu1 bcy1) that does not grow on but metabolizes xylose. In total, 541 phospho-peptides showed a ≥1.5 fold difference in abundance between Y184 bcy1 and Y184 or Y184 ira2, in both biological replicates. These peptides were classified into three groups: Class I peptides are those with a difference in phosphorylation level in Y184 bcy1 cultured anaerobically on xylose relative to both Y184 and Y184 ira2 cultured under those conditions. Class II peptides are those with differences between the Y184 bcy1 strain compared to Y184 ira2 only—Class II peptides therefore represent those where the bcy1 strain was more similar to Y184, neither of which grows anaerobically on xylose. Class III peptides are those whose phosphorylation was reproducibly different only in the bcy1 strain compared to Y184, revealing that the bcy1 strain behaved more like the Y184 ira2 strain, which can also metabolize xylose (FIG. 10B-10D). The inventors examined each cluster using enrichment and network analysis, under the hypotheses that Class II phospho-peptides may relate to the growth defect of Y127 and Y184 bcy1 whereas Class III phospho-peptides may be those associated with xylose metabolism, since both Y128 and Y184 bcy1 can metabolize the sugar under these conditions.

There were 188 phosphorylation events in Class I, unique to or amplified in the in bcy1 strain compared to both Y184 and Y184 ira2. These included 34 phospho-peptides (in 28 proteins) that showed increased phosphorylation in bcy1 and 154 phospho-peptides (mapping to 111 proteins) with a bcy1-specific decrease (FIG. 10B). Both groups included proteins related to the stress response and glycolysis. Interestingly, the bcy1 strain cultured anaerobically on xylose showed increased phosphorylation of serine 248 (S248) of Pbs2, the MAPKKK that activates the Hog1 kinase; in contrast, the strain showed reduced phosphorylation of T174 on Hog1, whose phosphorylation normally activates the kinase. This is especially intriguing because Hog1 inactivation in Y127 and other strains enhances xylose consumption. The data suggest that BCY1 deletion serves to down-regulate Hog1 signaling without mutation of the gene. The inventors previously proposed that Hog1 activity during glucose starvation may reduce growth-promoting processes, and thus deleting HOG1 (or down-regulating its activity) may enable xylose fermentation without the corresponding limitation of growth related processes.

Multiple hexokinases were affected uniquely in the bcy1 strain: Glk1 and Hxk1 both showed increased phosphorylation in the strain, whereas the main hexokinase, Hxk2, showed decreased phosphorylation on many sites (several shared with Y184 ira2). These included reduced phosphorylation on S158 that is normally autophosphorylated as a feedback mechanism to inactivate the enzyme, and S15 whose phosphorylation normally increases activity, see below. Hxk2 is an interesting enzyme, because it acts both in glycolysis and as a regulator of nuclear transcription via the Mig1 repressor. Decreased phosphorylation at these sites may have broader effects here: deletion of HXK2 results in constitutive expression of Snf1 targets to enable growth on non-glucose fermentable carbon sources. The data raise the possibility that hexokinase activity is decreased to affect how the cell senses and/or responds to glucose availability.

The inventors next analyzed phosphoproteomic changes in Class II, where the bcy1 strain (which metabolizes xylose but cannot grow on it) is more similar to Y184 that can neither grow on nor metabolize xylose (FIG. 10C). The inventors' hypothesis is that phosphorylation of peptides in this category may be related to the shared inability of these strains to grow anaerobically on xylose. There were 22 phospho-sites (in 18 proteins) with an increase in phosphorylation in Y184 bcy1 compared to Y184 ira2. Although there was no significant enrichment, there were several interesting proteins including transketolase (Tkl1) involved in pentose phosphate/xylose metabolism and intriguingly Rnr2, the main deoxyribonucleotide-diphosphate reductase critical for nucleotide biosynthesis and thus growth. Conversely, 28 phospho-sites (in 24 proteins) showed decreased in phosphorylation in the bcy1 strain compared to Y184 ira2. These included several proteins involved in ribosome biogenesis (Alb1 and Zuo1), mRNA transport (Nup60), as well as Mga2. It is possible that one or more of these phosphorylation differences inhibit growth in the bcy1 strain but enable continued xylose fermentation.

In contrast, Class III phosphorylation events were similar between Y184 bcy1 and Y184 ira2 strains, but distinct from Y184 that cannot metabolize xylose (FIG. 10D). The 51 phospho-sites (in 38 proteins) that displayed an increase in phosphorylation in the bcy1 strain compared to Y184 were enriched for stress response proteins, including the Yak1 kinase that is antagonistic to PKA signaling and activated during times of stress. Since PKA activity is known to suppress the stress response, this signature likely reflects PKA-dependent suppression of stress defense. Also included in the group of peptides with higher phosphorylation in xylose-fermenting strains is Cdc25, the guanine-nucleotide exchange factor for RAS and a known PKA target. Increased phosphorylation on Cdc25 site S135 is thought to increase its activity, which would promote RAS-dependent signaling and PKA activity. The increased phosphorylation of Cdc25 S135 is consistent with the notion that RAS/PKA activity is up-regulated by IRA2 or BCY1 deletion to promote increased xylose flux. The 262 phospho-sites (in 165 proteins) that showed a decrease in phosphorylation compared to Y184 were enriched for proteins involved in the regulation of cell shape, cytoskeleton, and bud site selection.

Interestingly, network analysis revealed that Pkh1 (involved endocytosis control), Yck2 (involved in morphogenesis, trafficking, and glucose response), Akl1 (endocytosis and cytoskeleton organization), and Ark1 (regulation of actin cytoskeleton) kinases all showed more interactions with the proteins whose phosphorylation decreased in this class, compared to what is expected by chance. Indeed, many of the 165 proteins to which the affected peptides mapped are involved in cytoskeleton regulation. Several other sites with decreased phosphorylation in the bcy1 and Y184 ira2 strains have known functions related to cell cycle progression, including histone Hta1 on S129 and Cdc3 on site S503. Decreased phosphorylation of Pah1 and Cho1 involved in lipid biogenesis is also predicted to reduce activity of the enzymes. It is intriguing that so many of these regulators are linked to growth, morphology, and cell-cycle progression; however, their phosphorylation patterns are shared between the growing Y184 ira2 and the arrested Y184 bcy1. One possibility is that these phosphorylation events are a unique response in the Y184 reference strain in response to its inability to grow, for reasons that are distinct than in Y184 bcy1.

Discussion of Results.

The results provide new insight into the upstream regulatory network that enables anaerobic xylose fermentation and the downstream cellular responses that mediate it. *S. cerevisiae* engineered with the required metabolic enzymes remains unable to utilize xylose without further modification, indicating a bottleneck in regulation rather than metabolic potential. This bottleneck blocks metabolism but also prevents the hypoxic response, revealing for the first time a connection between sugar and oxygen sensing in yeast. Evolved strain Y128 activates PKA signaling while requiring Snf1 for anaerobic xylose usage, leading to a cascade of downstream effects that involve the sugar-responsive Azf1, oxygen-responsive Mga2, and downstream effectors that control respiration (Hap4), stress response (Msn2/Msn4), and sugar transport (Mth1) among others. The response to xylose in anaerobically-grown Y128 thus combines responses normally seen on poor carbon sources (i.e. Snf1 activation, induced expression of hexose transporters including some that transport xylose, altered hexokinase regulation, and Azf1 activation) with responses typically restricted to the presence of abundant glucose (i.e. phosphorylation events associated with increased glycolytic flux, reduced expression of respiration and stress-responsive genes, and active PKA signaling). Snf1 and PKA are not normally coactivated in yeast. The primary exception is during invasive growth, a foraging response in which starved cells invade a solid substrate. Invasive growth is driven by combined PKA and Snf1 activation, which is triggered by nitrogen and glucose limitation. This ecological response may explain the link between sugar and oxygen responses, since cells undergoing substrate invasion may prepare for impending hypoxia. At the same time, the results strongly suggest that PKA is not simply up-regulated but rather 'rewired' to target some peptides while disfavoring others. Bcy1 is thought to direct PKA to specific sets of targets, much like AKAP proteins in mammalian cells. Recent studies in mammalian cells reveal that the PKA regulatory subunit does not disassociate from catalytic PKA subunits upon cAMP binding, raising the possibility that structural differences in Bcy1-AID could direct PKA to different sets of proteins. That some well-characterized PKA phospho-sites are up-regulated while others are suppressed in anaerobically-grown Y128 supports this hypothesis.

Integrating transcriptomic, phosphoproteomic, and metabolomic data across the strain panel also presents the downstream logic of anaerobic xylose fermentation (FIG. 11). Transcriptomic and metabolomic data are easiest to interpret, and the combined effects in Y128 lead to induction of sugar transporters as well as genes and metabolites in the non-oxidative branch of the pentose phosphate pathway, increased abundance of xylolytic and glycolytic intermediates, reduced abundance of overflow metabolites, and sharp reduction in respiration components. Phosphorylation changes remain difficult to interpret in isolation, but the inventors propose that the integrative model shown in FIG. 5 can be used to predict the functions of corresponding phosphorylation changes and may have utility in future engineering strategies.

Materials and Methods

Strains and Growth Conditions.

Cells were grown in YP medium (10 g/L yeast extract, 20 g/L peptone) with glucose or xylose added at 20 g/L final concentration, unless otherwise noted. Antibiotics were added where indicated at the following concentrations: 200 mg/L G418, 300 mg/L Hygromycin B, 100 mg/L ClonNat. For aerobic growth, cultures were grown at 30° C. with vigorous shaking in flasks. For anaerobic growth, media was incubated at 30° C. in a Coy anaerobic chamber (10% $CO_2$, 10% $H_2$, and 80% $N_2$) for ≥16 hours before inoculation, and cultures were grown at 30° C. in flasks using stir bars spinning at 300 rpm to reduce flocculation. Cultures were inoculated with a saturated culture of cells grown in YP-glucose medium, washed one time with the desired growth media, at the specified OD600 value as indicated. Cell growth was measured using OD600, and extracellular sugar and ethanol concentrations were measured with HPLC-RID (Refractive Index Detector) analysis.

Strains and Cloning.

*Saccharomyces cerevisiae* strains used in this study are described in Table 4. The creation of Y22-3, Y127, and Y128 and their antibiotic marker-rescued counterparts with the KanMX gene was removed (Y36, Y132, and Y133, respectively) was described previously. All strains express the minimal required genes for xylose metabolism, including xylose isomerase (xylA from *Clostridium phytofermentans*), xylulose kinase (XYL3 from *Scheffersomyces stipites*), and transaldolase (TAL3 from *S. cerevisiae*). Gene knockouts were generated by homologous recombination of the KanMX or Hph cassettes into the locus of interest and verified using multiple diagnostic PCRs. AZF1 and MGA2 were over-expressed using the MoBY 2.0 plasmid and empty vector as a control, growing cells in medium containing G418 to maintain the plasmid. BCY1 was deleted from indicated strains through homologous recombination of the KanMX cassette and verified by multiple diagnostic PCRs. Strain Y184 harboring integrated BCY1-AiD (Auxin-induced-Degron) was generated as follows: all plasmids were provided by National BioResource Program (NBRP) of the Ministry of Education, Culture, Sports and Technology (MEXT), Japan. Plasmid pST1933 (NBRP ID BYP8880) containing 3× Mini-AiD sequences, 5× FLAG Tag and KanMX was modified to include the 329 bp of BYC1 3' UTR between the 5× FLAG tag and the KanMX marker gene. This construct (3× Mini-AiD, 5× FLAG tag, BCY1 3' UTR, and KanMX) was amplified and inserted downstream and in-frame of BYC1 in Y184 (Y22-3 gre3 isu1) to form strain Y184 Bcy1-AiD. The integrated construct was verified by sequencing. Neither the pTIR plasmid enabling auxin-dependent degradation nor auxin was required for the desired effect (not shown), thus these were omitted from the analysis. Phenotypes introduced by BCY1 deletion were complemented by introducing BCY1 on a CEN plasmid: to generate the plasmid, BCY1 and 1000 bp upstream and 1000 bp downstream were amplified from Y128 and inserted into a NatMX-marked CEN plasmid via homologous recombination and sequence verified. This plasmid or the empty vector (pEMPTY) were transformed into appropriate strains. Phenotypes resulting from SNF1 deletion were complemented using the SNF1 MoBY 2.0 plasmid and compared to the empty vector control.

TABLE 4

Strains Used in this Study

| Strain Name | Description |
|---|---|
| Y22-3 | CRB Strain with xylose utilization genes (G418$^R$) |
| Y127 | Evolved Y22-3 for aerobic xylose utilization (G418$^R$) |
| Y128 | Evolved Y127 for anaerobic xylose utilization (G418$^R$) |
| Y36 | Y22-3 marker-rescued (MR) - lacking KanMX cassette |
| Y132 | Y127 marker-rescued (MR) - lacking KanMX cassette |
| Y133 | Y128 marker-rescued (MR) - lacking KanMX cassette |
| Y133 azf1 | Y133 azf1 ::KanMX (G418$^R$) |
| Y133 AZF1 MoBY | Y133 containing AZF1-MoBY 2.0 Plasmid (G418$^R$) |
| Y133 MoBY Control | Y133 containing Empty Vector MoBY 2.0 Plasmid (G418$^R$) |
| CEN.PK113-5D Xylose Strain | CEN.PK113-5D with HO ::ScTAL1-CpxylA-SsXYL3-loxP, isu1 ::loxP, hog1 ::KanMX, gre3 ::loxP, ira2 ::loxP |
| CEN.PK113-5D Xylose Strain AZF1 MoBY | CEN.PK113-5D Xylose Strain containing AZF1-MoBY 2.0 Plasmid (G418$^R$) |
| CEN.PK113-5D Xylose Strain MoBY Control | CEN.PK113-5D Xylose Strain containing Empty Vector MoBY 2.0 Plasmid (G418$^R$) |
| Y184 | Y22-3 gre3 ::MR isu1 ::loxP-Hyg (Hyg$^R$) |
| Y243 | Y22-3 gre3 ::MR isu1 ::loxP-Hyg ira2 ::MR (Hyg$^R$) |
| Y132 bcy1 | Y132 bcy1 ::KanMX (G418$^R$) |
| Y184 bcy1 | Y22-3 gre3 ::MR isu1 ::loxP-Hyg bcy1 ::KanMX (Hyg$^R$, G418$^R$) |
| Y243 bcy1 | Y22-3 gre3 ::MR isu1 ::loxP-Hyg ira2 ::MR bcy1 ::KanMX (Hyg$^R$, G418$^R$) |
| Y133 snf1 | Y133 SNF1::Hyg (Hyg$^R$) |
| Y184 snf1 | Y22-3 gre3 ::MR isu1 ::loxP-Hyg snf1 ::NatMX (Hyg$^R$, Nat$^R$) |
| Y184 bcy1 snf1 | Y22-3 gre3 ::MR isu1 ::loxP-Hyg bcy1 ::KanMX snf1 ::NatMX (Hyg$^R$, G418$^R$, Nat$^R$) |
| Y243 snf1 | Y22-3 gre3 ::MR isu1 ::loxP-Hyg ira2 ::MR snf1 ::NatMX (Hyg$^R$, Nat$^R$) |
| Y243 bcy1 snf1 | Y22-3 gre3 ::MR isu1 ::loxP-Hyg ira2 ::MR bcy1 ::KanMX snf1 ::NatMX (Hyg$^R$, G418$^R$, Nat$^R$) |
| Y133 snf1 SNF1 MoBY | Y133 snf1 ::Hyg containing SNF1-MoBY 2.0 Plasmid (Hyg$^R$, G418$^R$) |
| Y133 snf1 MoBY Control | Y133 snf1 ::Hyg containing Empty Vector MoBY 2.0 Plasmid (Hyg$^R$, G418$^R$) |
| Y133 mga2 | Y133 mga2 ::KanMX (G418$^R$) |
| Y133 MGA2 MoBY | Y133 containing MGA2-MoBY 2.0 Plasmid (G418$^R$) |
| Y184 bcy1 pBCY1 | Y22-3 gre3 ::MR isu1 ::loxP-Hyg bcy1 ::KanMX containing pBCY1 CEN Plasmid (Hyg$^R$, G418$^R$, Nat$^R$) |
| Y184 bcy1 Empty Control | Y22-3 gre3 ::MR isu1 ::loxP-Hyg bcy1 ::KanMX containing empty vector CEN Plasmid (Hyg$^R$, G418$^R$, Nat$^R$) |

TABLE 4-continued

Strains Used in this Study

| Strain Name | Description |
|---|---|
| Y132 BCY1-3' AiD | Y132 BCY1-3' AiD tag (3x Mini-Auxin Induced Degron Sequence-5x FLAG-BCY1-3' UTR-KanMX) (G418$^R$) |
| Y184 BCY1-3' AiD | Y22-3 gre3 isu1 BCY1-3' AiD tag (3x Mini-Auxin Induced Degron Sequence-5x FLAG-BCY1-3' UTR-KanMX) (G418$^R$) |
| Y243 BCY1-3' AiD | Y36 gre3 isu1 ira2 BCY1-3' AiD tag (3x Mini-Auxin Induced Degron Sequence-5x FLAG-BCY1-3' UTR-KanMX) (G418$^R$) |

Y133 tpk1 tpk3 tpk2$^{as}$ was generated using CRISPR/Cas9-mediated genome editing. TPK1 and TPK3 were deleted in Y133 independently and verified by PCR. sgRNA sequence (GTGATGGATTATATCAGAAGG) that targeted the location within TPK2 to be replaced was cloned into the pXIPHOS vector using NotI (GenBank accession MG897154), which contains the constitutive RNR2 promoter driving the Cas9 gene and NatMX resistance gene, using gapped plasmid repair using HiFi DNA Assembly Master Mix from NEB. tpk2$^{as}$ repair templates were generated by PCR of the whole ORF of tpk2$^{as}$ from a strain containing mutants of the TPK genes that are sensitive to the ATP-analogue inhibitor 1-NM-PP1 (TPK1 M164G, TPK2 M147G, TPK3 M165G). Purified repair templates were co-transformed at a 20-fold molar excess with the pXIPHOS-TPK2 sgRNA plasmid into Y133 tpk1 tpk3 strain. Colonies resistant to nourseothricin were restreaked onto YPD two times to remove the plasmid (and were verified to now be sensitive to nourseothricin) and tpk2$^{as}$ presence was verified by sequencing. Y133 tpk1 tpk3 tpk2$^{as}$ was grown in xylose anaerobically for 17 hours at which point 10 μM 1-NM-PP1 or DMSO control was added to the cultures.

Transcriptomic Sample Collection, Library Construction, and Sequencing.

Y22-3, Y127, and Y128 grown in YPD or YPX, with or without oxygen, were collected in biological duplicate on different days. Data from replicates were highly correlated (average $R^2$ of log 2(fold changes)=0.93) and additional statistical power was incurred by analyzing across all strain data. Duplicates were used due to limitations with phosphoproteomic techniques. Cultures were inoculated from a saturated aerobic sample grown in rich glucose medium (YPD), washed with the corresponding growth media, and grown for ~3 generations aerobically or anaerobically until the cultures reached mid-log phase (OD$_{600}$ of ~0.5). Strains Y22-3 and Y127 were inoculated in rich xylose medium (YPX) at an OD$_{600}$ of ~0.5 and incubated anaerobically for the same amount of time as the other cultures. Y22-3 and Y127 retained over 95% viability as measured by CFU/mL after 17 hours of anaerobic incubation on xylose. Growth was halted by adding 30 mL of culture to ice cold 3.75 mL 5% phenol (pH<5)/95% ethanol solution, cultures were spun for 3 min at 3000 rpm, the decanted pellet was flash frozen in liquid nitrogen and stored at −80° C. until needed. Total RNA was isolated by hot phenol lysis and DNA was digested using Turbo-DNase (Life Technologies, Carlsbad, Calif.) for 30 min at 37° C., followed by RNA precipitation at −20° C. in 2.5 M LiCl for 30 min. rRNA depletion was performed using EpiCentre Ribo-Zero Magnetic Gold Kit (Yeast) RevA kit (Illumina Inc., San Diego, Calif.) and purified using Agencourt RNACleanXP (Beckman Coulter, Indianapolis, Ind.) following manufacturers' protocols. RNA-seq library generation was performed using the Illumina TruSeq stranded total RNA kit (Illumina) using the sample preparation guide (revision C) with minor modifications, AMPure XP bead for PCR purification (Beckman Coulter, Indianapolis, Ind.), and SuperScript II reverse transcriptase (Invitrogen, Carlsbad, Calif.) as described in the Illumina kit. Libraries were standardized to 2 μM. Cluster generation was performed using standard Cluster kits (version 3) and the Illumina Cluster station. Single-end 100-bp reads were generated using standard SBS chemistry (version 3) on an Illumina HiSeq 2000 sequencer. All raw data were deposited in the NIH GEO database under project number GSE92908.

Y133, Y133 azf1, Y133 with the AZF1 MoBY 2.0 plasmid, and Y133 carrying the MoBY 2.0 empty-vector control were grown in xylose −O2 (+/−G418 as needed), duplicate samples were collected on different days and RNA was isolated and DNA digested as described above. The inventors focused on genes affected in multiple strains for increased statistical power. rRNA depletion was performed using EpiCentre Ribo-Zero Magnetic Gold Kit (Yeast) RevA kit (Illumina) following manufacturer's protocols and cleaned using Qiagen RNease MinElute Cleanup kit (Qiagen, Hilden, Germany). RNA-seq library generation was performed using the EpiCentre Strand Specific ScriptSeq Kit (Illumina) as above except that Axygen AxyPrep Mag PCR Cleanup Kits for PCR purification (Axygen, Corning, N.Y.) were used and LM-PCR was performed using 12 cycles using EpiCentre ScriptSeq Index PCR Primers (Illumina) and Epicenter Failsafe PCR Enzyme Mix (Illumina). Single-end 100-bp reads were generated using standard SBS chemistry (version 4) on an Illumina HiSeq 2500 sequencer and the two FASTQ files for each sample were combined using the "cat" command.

RNA-Seq Processing and Analysis.

Cultures were grown aerobically or anaerobically for three generations and collected at OD$_{600}$~0.5 by adding cells to ice cold 5% phenol/95% ethanol solution. Cell lysis and RNA purification was performed as previously described. RNA-seq libraries were made using either the Illumina TruSeq Stranded Total RNA Kit (Illumina) or the EpiCentre Ribo-Zero Magnetic Gold Kit (Yeast) RevA followed by the EpiCentre Strand Specific ScriptSeq Kit (Illumina), following manufacture's protocols. RNA-seq libraries were run on either the Illumina HiSeq 2000 sequencer or the Illumina HiSeq 2500 sequencer.

Reads for all RNA-seq experiments were processed with Trimmomatic version 0.3 and mapped to the Y22-3 genome using Bowtie 2 version 2.2.2 with default settings. HTSeq version 0.6.0 was used to calculate read counts for each gene using the Y22-3 annotation. Differential expression analysis was performed using edgeR version 3.6.8 using pairwise comparisons, taking Benjamini and Hochberg false discovery rate (FDR)<0.05 as significant. Raw sequences were normalized using the reads per kilobase per million mapped reads (RPKM) method. Clustering analysis was performed using MClust version 4.4 and visualized using Java TreeView, see jtreeview.sourceforge.net. Functional enrichment analysis was performed using the FunSpec database or a hypergeometric test using GO annotation terms. All examined targets of TFs were obtained from YeasTract using only those with DNA binding evidence.

Azf1 Motif Identification.

The inventors analyzed the log 2(fold change) in expression for each strain grown anaerobically in xylose compared to anaerobically in glucose. Genes with a progressive xylose-responsive induction across the strain panel were identified if the replicate-averaged $\log_2$(fold-change) in Y127 was ≥1.5 fold higher than in Y22-3, and if the replicate-averaged $\log_2$(fold-change) in Y128 was also ≥1.5 fold higher than in Y127. 21 classical hypoxic genes, those known to be involved in the hypoxic response, were selected from the literature to measure the hypoxic response (Table 3) and for enrichment analysis to score the hypoxic response. The inventors selected 15 of these genes with no induction in Y22-3 grown anaerobically on xylose and performed motif analysis, by extracting 1000 bp upstream of these genes and submitting to MEME using the 'any number of sequences' model. The top motif matched the Azf1 binding site in TomTom. WebLogo was used to construct the final PWM logos for publication. Matches to this matrix were identified in 500 bp upstream regions in the Y22-3 genome using MAST with default settings. A total of 433 significant (E-value <10) sites were identified in all intergenic regions in the genome.

Analysis of Expression in Azf1 and AZF1-Over-Expressing Strains.

Differentially expressed genes were identified using edgeR as described above, comparing Y133 azf1 to Y133 (identifying 441 differentially expressed genes at FDR<0.05) and comparing Y133 AZF1-MoBY 2.0 compared to Y133 carrying the empty vector control (1,525 genes at FDR<0.05). The inventors identified 411 genes whose expression was significantly altered (FDR<0.05) by AZF1 over-expression and whose replicate-averaged expression was at least 1.5× different in Y128 versus Y22-3 cultured anaerobically on xylose and whose expression showed the same directionality as in response to AZF1 over-expression. That is, genes that showed an increase in expression when AZF1 was over-expressed (relative to the control) also showed an increase in expression in Y128 (relative to Y22-3), and vice versa. Functional enrichment analysis was performed using the FunSpec database or hypergeometric test of GO annotation terms or compiled sets of TF targets.

Label Free Quantitative Proteomics Preparation and Analysis.

For comparison of the Y22-3, Y127, and 128 proteomes, duplicate samples were collected from the same samples used for RNA-seq above. Duplicates were used due to limitations with phosphoproteomic techniques. 35 mL of cultures were spun for 3 min at 3000 rpm, the supernatant was removed and the pellet was flash frozen in liquid nitrogen and stored at −80° C.

Label free proteomics were performed similarly to previous work. For protein extraction and digestion, yeast cell pellets were lysed by glass bead milling (Retsch GmbH, Germany). Lysate protein concentration was measured via bicinchoninic acid protein assay (Thermo Pierce, Rockford, Ill.), and yeast proteins were reduced through incubation in 5 mM dithiothreitol (DTT) for 45 minutes at 58° C. Free cysteines were alkylated in 15 mM iodoacetamide in the dark for 30 minutes. The alkylation was stopped with 5 mM DTT. A 1 mg protein aliquot was digested overnight at room temperature in 1.5 M urea with trypsin (Promega, Madison, Wis.) added at a 1:50 (w/w) enzyme to protein ratio. Digestions were quenched by the addition of trifluoroacetic acid (TFA, Thermo Pierce) and were desalted over tC18 Sep-Pak cartridges (Waters, Milford, Mass.).

For online nanoflow liquid chromatography tandem mass spectrometry (nLC-MS/MS), reversed phase columns were packed-in house using 75 μm ID, 360 μm OD bare fused silica capillary. A nanoelectrospray tip was laser pulled (Sutter Instrument Company, Novato, Calif.) and packed with 1.7 μm diameter, 130 Å pore size Ethylene Bridged Hybrid C18 particles (Waters) to a length of 30-35 cm. Buffer A consisted of 0.2% formic acid and 5% DMSO in water, and Buffer B consisted of 0.2% formic acid in acetonitrile. Two μg of peptides were loaded onto the column in 95% buffer A for 12 min at 300 min-1. Gradient elution was performed at 300 nL min-1 and gradients increased linearly from 5 to 35% buffer B over 190 minutes, followed by an increase to 70% B at 215 minutes and a wash at 70% B for 5 minutes. The column was then re-equilibrated at 5% B for 20 minutes. Eluting peptide were ionized with electrospray ionization at +2 kV, and the inlet capillary temperature was held at 300° C. on an ion trap-Orbitrap hybrid mass spectrometer (Orbitrap Elite, Thermo Fisher Scientific, San Jose, Calif.). Survey scans of peptide precursors were collected over the 300-1500 Thompson range in the Orbitrap with an automatic gain control target value of 1,000,000 (50 ms maximum injection time), followed by data-dependent ion trap MS/MS scans using collisional activation dissociation (CAD) of the 20 most intense peaks (AGC target value of 5,000 and maximum injection times of 100 ms). Precursors with charge states equal to one or unassigned were rejected.

Raw data was processed using MaxQuant version 1.4.1.2, and tandem mass spectra were searched with the Andromeda search algorithm. Oxidation of methionine was specified as a variable modification, while carbamidomethylation of cysteine was a set as a fixed modification. A precursor search tolerance of 20 ppm and a product mass tolerance of 0.35 Da were used for searches, and three missed cleavages were allowed for full trypsin specificity. Peptide spectral matches (PSMs) were made against a target-decoy custom database of the yeast strain was used, which was concatenated with a reversed sequence version of the forward database from McIlwain et al. Peptides were filtered to a 1% false discovery rate (FDR) and a 1% protein FDR was applied according to the target-decoy method. Proteins were identified using at least one peptide (razor+unique), where razor peptide is defined as a non-unique peptide assigned to the protein group with the most other peptides (Occam's razor principle). Proteins were quantified and normalized using MaxLFQ with a label-free quantification (LFQ) minimum ratio count of 2. LFQ intensities were calculated using the match between runs feature, and MS/MS spectra were not required for LFQ comparisons. For quantitative comparisons, protein intensity values were log 2 transformed prior to further analysis. All possible proteins were analyzed as long as the proteins were identified in both strains being compared, to maximize data obtained from this analysis. In total, 3,550 unique proteins were identified in across all strains and conditions. All raw mass spectrometry files and associated information about identifications are available on Chorus under Project ID 999 and Experiment ID 3007.

Correlation Between Transcriptomic and Proteomic Differences Across Media Conditions.

The response to anaerobiosis was calculated for each strain growing either on glucose or xylose, as the log 2 of mRNA or protein abundance in glucose $-O_2$/glucose $+O_2$ or xylose $-O_2$/xylose $+O_2$. The replicate-averaged $\log_2$(fold-change) in mRNA was compared to the log 2(fold-change) in protein for each strain (FIG. 7A).

Phosphoproteomic Analysis.

Phosphoproteomic experiments were multiplexed using tandem mass tags (TMT) isobaric labels to quantitatively compare the phosphoproteomes of Y22-3, Y127, and Y128 yeast strains. 6-plex experiments were performed to compare the three strains grown on xylose under aerobic and anaerobic conditions. Yeast phosphoproteomes were obtained from cell pellets from the same cultures used for the label free experiments described above using the same protein extraction, proteolytic digestion, and desalting conditions. A second phosphoproteomic experiment used TMT tags to compare the phosphoproteomic profiles of Y184, Y184 ira2, and Y184 bcy1 during anaerobic growth on xylose in duplicate, using the same collection and methods outlined above.

Following the generation of tryptic peptides, 500 μg of peptides from each condition were labeled with TMT 6-plex isobaric labels (Thermo Pierce) by re-suspending peptides in 200 μL of freshly made 200 mM triethylammonium biocarbonate (TEAB) and combining with 50 μL of the TMT labeling reagent resuspended in 100% acetonitrile. The samples were labeled for 4 hours, then ~5 μg of material from each TMT channel was combined into a test mix and analyzed by LC-MS/MS to evaluate labeling efficiency and obtain optimal ratios for sample recombination. Samples were quenched with 1.6 μL of 50% hydroxylamine, then combined in equal amounts by mass, and desalted.

Combined TMT-labeled peptides were then enriched for phospho-peptides using immobilized metal affinity chromatography (IMAC) with magnetic beads (Qiagen, Valencia, Calif.). After equilibration with water, the magnetic beads were incubated with 40 mM EDTA (pH 8.0) for 30 minutes while shaking. This process was repeated for a total of two incubations. Next, the beads were washed four times with water and incubated with 30 mM FeCl3 for 30 minutes while shaking, and this was also repeated for a total of two incubations. Beads were then washed four times with 80% acetonitrile/0.15% TFA. The TMT-labeled peptides were re-suspended in 80% acetonitrile/0.15% TFA and incubated with the magnetic beads for 45 minutes with shaking. Unbound peptides were collected for protein analysis. Bound peptides were washed three times with 80% acetonitrile/0.15% TFA and eluted with 50% acetonitrile, 0.7% NH4OH. Eluted peptides were immediately acidified with 4% formic acid, frozen, and lyophilized. Enriched phospho-peptides were re-suspended in 20 μL 0.2% FA for LC-MS/MS analysis.

Online nanoflow liquid chromatography tandem mass spectrometry (nLC-MS/MS) was performed similarly as to the methods described above, including the same LC system and buffers, capillary reversed phase columns, gradient, and MS system and electrospray conditions. TMT phosphoproteomic experiments were also performed as single-shot (i.e., no fractionation) four-hour experiments. Survey scans of peptide precursors were collected over the 300-1500 Thompson range in the Orbitrap with a resolving power of 60,000 at 400 m/z and an automatic gain control target value of 1,000,000 (75 ms maximum injection time), followed by data-dependent MS/MS scans in the Orbitrap (resolving power 15,000 at 400 m/z) using higher-energy collisional dissociation (HCD, normalized collision energy of 35) of the 15 most intense peaks (AGC target value of 50,000 and maximum injection times of 200 ms). The first mass of MS/MS scans was fixed at 120 m/z, precursors were isolated with 1.8 Th isolation width, and precursors with charge states equal to one or unassigned were rejected. Dynamic exclusion windows were created around monoisotopic precursor peaks using 10 ppm windows, and the exclusion duration lasted for 40 seconds. Two technical replicate injections of each sample were performed.

Data processing for the TMT phosphoproteomic experiments used COMPASS. The Open Mass Spectrometry Search Algorithm (OMSSA) searches were performed against the same target-decoy yeast database used in the label free experiments described above. Searches were conducted using a 125 ppm precursor mass tolerance and a 0.02 Da product mass tolerance. A maximum of 3 missed tryptic cleavages were allowed. Fixed modifications were carbamidomethylation of cysteine residues, TMT 6-plex label on peptide N-termini, and TMT 6-plex on lysine. Variable modifications included oxidation of methionine; TMT 6-plex on tyrosine residues; phosphorylation of serine, threonine, and tyrosine residues; and neutral loss of phosphorylation on serine and threonine residues. A false discovery rate of 1% was used at the peptide and protein level. Within COMPASS, TMT quantification was performed and quantified peptides were grouped into proteins as described. Phospho-peptide localization was performed using phosphoRS integrated with COMPASS, using 75% as a localization probability cutoff to determine localized phospho-sites. Phospho-peptides with non-localized phospho-sites were discarded from further analysis. TMT reporter ion intensities were normalized for changes in protein level and log 2 transformed prior to further analysis. The Phospho-GRID database was used to identify phospho-sites of known function. All raw mass spectrometry files and associated information about identifications are available on Chorus under Project ID 999 and Experiment IDs 3016 and 3166.

Phosphoproteomic Network Analysis.

The inventors developed a novel network approach to infer kinases and phosphatases that mediate phosphoproteomic changes across the strain panel. The method predicts co-regulated groups of phospho-peptides, called modules, and then searches a background network of protein-protein interactions to identify 'shared interactor' proteins that physically interact with more module constituent proteins then expected by chance. The method consists of four steps: to identify potentially co-regulated peptides, the method 1) classifies phospho-peptides according to phosphorylation profiles across strains and then 2) within each class, partitions peptides into 'modules' of peptides that share the same motif around the phosphorylated site (phospho-motif). 3) To identify potential regulators of each module, the method identifies 'shared interactor' proteins that physically interact with more module constituents than expected by chance, and then 4) identifies the subset of shared interactors that are kinases and phosphatases, focusing on regulators whose known specificity matches the target module phospho-motif. These steps are described in more detail below.

1) Classifying Phospho-peptides. Phospho-peptides were partitioned into four classes based on the log 2(fold-change) in phosphorylation in each strain grown in xylose $-O2$ versus xylose $+O2$. Class A contained phospho-peptides that show progressive increases or decreases in phosphorylation response (at least 1.5 fold difference in replicate-averaged log 2 expression changes, as described above) across Y22-3, Y127, and Y128. This identified 182 phospho-peptides from 154 proteins that showed a progressive increase in response across Y22-3, Y127, and Y128 and 225 phospho-peptides from 150 proteins that showed a progressive decrease in response across the strains; these were separated into "Class A-increasing" and "Class A-decreasing" groups. Class B contained phospho-peptides with a unique hypoxic response in xylose in Y128 (at least 1.5 fold absolute difference in Y128 compared to both Y127 and Y22-3, and no significant difference between Y127 and Y22-3). This identified 108 phospho-peptides from 96 proteins that showed a larger response in Y128 and 157 phospho-peptides from 138 proteins that showed a smaller log 2 fold-change in Y128; these were separated into "Class B-increasing" and "Class B-decreasing" groups.

2) Identifying phosphorylation motifs. Peptides from each of the four classes defined above were partitioned into modules using the program motif-X (76, 77) using the following parameters: extend from SGD yeast proteome; central character as s* or t*; motif width of 13; motif occurrences of 10; motif significance 1×10-6. Three total motifs were identified for Class A and five total motifs were identified for Class B. Groups of phospho-peptides containing the same motif are referred to as modules.

3) Identifying Shared Interactor proteins. Under the assumption that co-regulated peptides interact with the same responsible regulator, the inventors searched a background dataset of protein-protein interactions to identify 'shared interactors' (SIs) that interact with more module constituents then expected by chance, using a custom Python script. The background network was taken from a previously compiled collection of high and low-throughput protein-protein interactions or kinase-substrate interactions in $S.$ $cerevisiae$ and contains 4,638 proteins and 25,682 directed and non-directed interactions. For each module, the script identifies all proteins from the background network that interact with more module constituent proteins then expected by chance (hypergeometric test), using Benjamini-Hochberg correction and an FDR<0.05 as significant. This analysis revealed 59 SIs connected to Class A modules and 90 SIs connected to Class B modules.

4) Identifying candidate module regulators. The inventors focused on the subset of SIs that are kinases with known specificity and phosphatases whose interactions with the module were primarily directed toward module constituents or were undirected. For the kinases with known specificity, the inventors scored if the module phosphorylation motif matched the kinase motif as follows: Briefly, a position-weight matrix (PWM) was constructed for each module and compared to the PWM representing known kinase phosphorylation preferences from Mok et al. These PWMs were generated from a peptide phosphorylation spot array assay where the normalized, background-corrected value is provided as a weight for each amino acid at each position, which was converted to a frequency value by calculating the total of all signal intensities for all amino acids at each position and then dividing by the total sum of the intensities. A pseudocount was used to prevent overfitting and to remove zeros that may occur in the Mok et al PWMs. These generated kinase PWMs were compared to the motif-X motifs via Kullback-Leibler Divergence (KLD). Statistical significance of matches was determined using a distribution of KLD scores generated from randomizing the within-column values and then shuffling the columns themselves 1000 times. This generated 63,000 random KLD scores per module motif. FDR was calculated as the number of random KLD scores with smaller values than the observed value. Kinases whose known specificity matched the module phosphorylation motif were retained for further consideration along with identified phosphatases. Using this approach, 6 kinases and 2 phosphatases were identified for Class A modules and 5 kinases were identified for Class B modules. Networks were visualized using Cytoscape (version 3.4.0).

Phosphoproteomic Analysis Across Strains with and without BCY1.

The inventors identified phospho-peptides with a reproducible log 2 expression difference of at least 1.5× in both biological replicates in Y184 bcy1 compared to Y184 (which mimics Y127) or in Y184 bcy1 compared to Y184 ira2 (which mimics Y128). Phospho-peptides were clustered using MClust version 4.4 and visualized using Java TreeView, see jtreeview.sourceforge.net. Functional enrichment analysis was performed with a hypergeometric test using data sets compiled of up-to-date GO annotation terms, using as the background dataset the starting set of peptides used in this analysis. Phosphorylation motifs were identified as described above using motif-X.

Metabolomics Analysis.

Metabolite data from Sato et al. was analyzed to compare changes in Y128 xylose −O2 versus Y22-3 xylose −O2. A paired T-test was used to compare changes and those with a p-value ≤0.05 were considered significant.

Inhibition of Growth Using Hydroxyurea.

Growth inhibition was performed using 400 mM hydroxyurea, added after 17 hours of anaerobic growth in xylose. Before and after growth inhibition, $OD_{600}$ as well as sugar and ethanol concentrations were measured as above.

PKA Activity Assay.

Measurement of PKA activity was performed on lysed cells using the PKA Kinase Activity Assay Kit from ABCAM. Cultures were grown anaerobically in xylose for three doublings (to OD~0.5), at which 10 mL of cells were collected by centrifugation for 3 minutes at 3000 rpm, in preparation for lysis. Supernatant was removed under anaerobic conditions and the cells were resuspended in 1 mL of SB buffer (1 M sorbitol, 20 mM Tris HCl, pH 7.4) with 300 units of zymolyase (Amsbio) and 10 µL of protease inhibitor cocktail IV (Millipore). Cells were incubated for 10 minutes at 30° C. anaerobically. Cells were collected by certification for 5 minutes at 350 xg and washed 1× with SB buffer under anaerobic conditions. Cells were resuspended in 750 HLB buffer (10 mM Tris HCl, pH 7.4, 10 mM NaCl, 3 mM MgCl2, 0.3% (vol/vol) NP-40, 10% (vol/vol) glycerol) with 10 µL protease inhibitor cocktail IV and incubated on ice for 10 minutes, anaerobically. Cultures were subjected to ten rounds in a Dounce homogenizer anaerobically to promote lysis. Lysis was verified using microscopy and total protein abundance was determined using a Bradford assay. 200 µL of cell lysate was removed and 50 µM H-89 was added as a PKA inhibitor and incubated for 10 minutes at 30° C. anaerobically. The PKA Kinase Activity Assay Kit was performed following manufacture's protocol, with the kinase reaction occurring under anaerobic conditions and the remaining steps (primary and secondary antibody incubation and washes) being performed aerobically. The reaction was detected using a TECAN Infinite 200 Pro with a wavelength of 450 nm. Positive (active PKA provided by ABCAM) and negative (no cells, blank) controls were used for each experimental reaction as verification of kit functionality. Relative PKA activity was calculated by subtracting the measured absorbance for each sample from the absorbance from the blank to remove background, followed by normalization to total protein abundance for each sample. Paired T-tests were used to determine significant differences among samples.

Sugar Consumption and Ethanol Production Rate Calculations.

Sugar consumption and ethanol production rates were calculated with a rate estimation tool as described previously using cell density (OD600) and extracellular sugar concentrations measured by HPLC-RID. Log 2 data from each of three independent biological replicates were fit with linear models, and xylose consumption or ethanol production rate was calculated as g/L/OD/hour. Rates calculated for each replicate were plotted and compared with a paired T-test.

Bcy1-AiD Fermentation.

Experiments were designed to mimic high-cell titer industrial fermentations. Cells were grown in YP-6% glucose or YP-3% xylose to match sugar concentrations in hydrolysate. Strain Y184 Bcy1-AiD was grown aerobically in 6% glucose medium starting at an OD600 0.1 or grown anaerobically in 3% xylose medium starting at OD600 4.0. The tagged strain was compared to Y128, Y184 and Y184 bcy1. OD600 and glucose, xylose, and ethanol were measured and rates were determined as described above. Bcy1-AiD stability was measured for each experiment using Western blot analysis as described previously. Because the AiD tag contained a 3×-FLAG sequence, α-FLAG antibody (1:2500, Sigma) was used to detect Bcy1-AiD while α-Actin antibody (1:2500, Pierce) was used to detect actin as a loading control. The blot in FIG. 22 is representative of biological triplicates.

This specification incorporates the nucleic acid sequence listing that is concurrently submitted in computer readable form.

As can be appreciated, the results described in the above examples support the utility of the nucleic acids, yeast strains and methods described and claimed herein for enhancing biofuel production in yeast. Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific materials, methods, formulations, reaction/assay conditions, etc., herein illustrated and described, but embraces such modified forms thereof as come within the scope of the following claims.

REFERENCES

1. Kricka W, Fitzpatrick J, Bond U (2015) Challenges for the production of bioethanol from biomass using recombinant yeasts. *Adv Appl Microbiol* 92:89-125.
2. Moysés D N, Reis V C B, de Almeida J R M, de Moraes L M P, Tones F A G (2016) Xylose Fermentation by *Saccharomyces cerevisiae*: Challenges and Prospects. *Int J Mol Sci* 17(3):207.
3. Smets B, et al. (2010) Life in the midst of scarcity: adaptations to nutrient availability in *Saccharomyces cerevisiae*. *Curr Genet* 56(1):1-32.
4. Conrad M, et al. (2014) Nutrient sensing and signaling in the yeast *Saccharomyces cerevisiae*. *FEMS Microbiol Rev* 38(2):254-299.
5. Kayikci Ö, Nielsen J (2015) Glucose repression in *Saccharomyces cerevisiae*. *FEMS Yeast Res* 15(6):fov068.
6. Parreiras L S, et al. (2014) Engineering and Two-Stage Evolution of a Lignocellulosic Hydrolysate-Tolerant *Saccharomyces cerevisiae* Strain for Anaerobic Fermentation of Xylose from AFEX Pretreated Corn Stover. *PLoS ONE* 9(9):e107499.
7. Sato T K, et al. (2016) Directed Evolution Reveals Unexpected Epistatic Interactions That Alter Metabolic Regulation and Enable Anaerobic Xylose Use by *Saccharomyces cerevisiae*. *PLoS Genetics* 12(10):e1006372.
8. Matsushika A, Goshima T, Hoshino T (2014) Transcription analysis of recombinant industrial and laboratory *Saccharomyces cerevisiae* strains reveals the molecular basis for fermentation of glucose and xylose. *Microb Cell Fact* 13:16.
9. Li Y-C, et al. (2017) Transcriptome changes in adaptive evolution of xylose-fermenting industrial *Saccharomyces cerevisiae* strains with δ-integration of different xylA genes. *Appl Microbiol Biotechnol* 101(20):7741-7753.
10. Schwelberger H G, Kang H A, Hershey J W (1993) Translation initiation factor eIF-5A expressed from either of two yeast genes or from human cDNA. Functional identity under aerobic and anaerobic conditions. *J Biol Chem* 268(19):14018-14025.
11. Stein I, Kricke J, Becher D, Lisowsky T (1998) Azf1p is a nuclear-localized zinc-finger protein that is preferentially expressed under non-fermentative growth conditions in *Saccharomyces cerevisiae*. *Curr Genet* 34(4):287-296.
12. Newcomb L L, Hall D D, Heideman W (2002) AZF1 is a glucose-dependent positive regulator of CLN3 transcription in *Saccharomyces cerevisiae*. *Mol Cell Biol* 22(5):1607-1614.
13. Slattery M G, Liko D, Heideman W (2006) The function and properties of the Azf1 transcriptional regulator change with growth conditions in *Saccharomyces cerevisiae*. *Eukaryot Cell* 5(2):313-320.
14. Bolotin-Fukuhara M (2017) Thirty years of the HAP2/3/4/5 complex. *Biochimica et Biophysica Acta (BBA)—Gene Regulatory Mechanisms* 1860(5):543-559.
15. Martinez-Pastor M T, et al. (1996) The *Saccharomyces cerevisiae* zinc finger proteins Msn2p and Msn4p are required for transcriptional induction through the stress response element (STRE). *EMBO J* 15(9):2227-2235.
16. Michael D G, et al. (2016) Model-based transcriptome engineering promotes a fermentative transcriptional state in yeast. *Proc Natl Acad Sci USA* 113(47):E7428-E7437.
17. Roy A, Jouandot D, Cho K H, Kim J-H (2014) Understanding the mechanism of glucose-induced relief of Rgt1-mediated repression in yeast. *FEBS Open Bio* 4(1): 105-111.
18. Jiang Y, et al. (2001) MGA2 is involved in the low-oxygen response element-dependent hypoxic induction of genes in *Saccharomyces cerevisiae*. *Mol Cell Biol* 21(18): 6161-6169.
19. MacGilvray M E, et al. (2018) Network inference reveals novel connections in pathways regulating growth and defense in the yeast salt response. *PLoS Comput Biol* 13(5):e1006088.
20. Homma M K, et al. (2005) CK2 phosphorylation of eukaryotic translation initiation factor 5 potentiates cell cycle progression. *Proc Natl Acad Sci USA* 102(43): 15688-15693.
21. Kallmeyer A K, Keeling K M, Bedwell D M (2006) Eukaryotic release factor 1 phosphorylation by CK2 protein kinase is dynamic but has little effect on the efficiency of translation termination in *Saccharomyces cerevisiae*. *Eukaryot Cell* 5(8):1378-1387.

22. Gandin V, et al. (2016) mTORC1 and CK2 coordinate ternary and eIF4F complex assembly. *Nat Comms* 7:11127.
23. Ewald J C, Kuehne A, Zamboni N, Skotheim J M (2016) The Yeast Cyclin-Dependent Kinase Routes Carbon Fluxes to Fuel Cell Cycle Progression. *Mol Cell* 62(4): 532-545.
24. Zhao G, Chen Y, Carey L, Futcher B (2016) Cyclin-Dependent Kinase Co-Ordinates Carbohydrate Metabolism and Cell Cycle in *S. cerevisiae*. *Mol Cell* 62(4):546-557.
25. Broach J R (2012) Nutritional Control of Growth and Development in Yeast. *Genetics* 192(1):73-105.
26. Colombo S, Ronchetti D, Thevelein J M, Winderickx J, Martegani E (2004) Activation state of the Ras2 protein and glucose-induced signaling in *Saccharomyces cerevisiae*. *J Biol Chem* 279(45):46715-46722.
27. Garreau H, et al. (2000) Hyperphosphorylation of Msn2p and Msn4p in response to heat shock and the diauxic shift is inhibited by cAMP in *Saccharomyces cerevisiae*. *Microbiology* 146(9):2113-2120.
28. Costanzo M, et al. (2010) The genetic landscape of a cell. *Science* 327(5964):425-431.
29. Zaman S, Lippman S I, Schneper L, Slonim N, Broach J R (2009) Glucose regulates transcription in yeast through a network of signaling pathways. *Mol Syst Biol* 5(1):245.
30. Mösch H-U, Kubler E, Krappmann S, Fink G R, Braus G H (1999) Crosstalk between the Ras2p-controlled Mitogen-activated Protein Kinase and cAMP Pathways during Invasive Growth of *Saccharomyces cerevisiae*. *MBC* 10:1325-1335.
31. Ho J, Bretscher A (2001) Ras regulates the polarity of the yeast actin cytoskeleton through the stress response pathway. *Molecular Biology of the Cell* 12(6):1541-1555.
32. Weeks G, Spiegelman G B (2003) Roles played by Ras subfamily proteins in the cell and developmental biology of microorganisms. *Cell Signal* 15(10):901-909.
33. Cannon J F, Tatchell K (1987) Characterization of *Saccharomyces cerevisiae* genes encoding subunits of cyclic AMP-dependent protein kinase. *Mol Cell Biol* 7(8):2653-2663.
34. Cai Z, Zhang B, Li Y (2012) Engineering *Saccharomyces cerevisiae* for efficient anaerobic xylose fermentation: reflections and perspectives. *Biotechnol J* 7 (1):34-46.
35. Vilela L de F, et al. (2015) Enhanced xylose fermentation and ethanol production by engineered *Saccharomyces cerevisiae* strain. *AMB Express* 5:16.
36. Kriegel T M, Rush J, Vojtek A B, Clifton D, Fraenkel D G (1994) In vivo phosphorylation site of hexokinase 2 in *Saccharomyces cerevisiae*. *Biochemistry* 33(1):148-152.
37. Warmka J, Hanneman J, Lee J, Amin D, Ota I (2001) Ptc1, a type 2C Ser/Thr phosphatase, inactivates the HOG pathway by dephosphorylating the mitogen-activated protein kinase Hog1. *Mol Cell Biol* 21(1):51-60.
38. Santos dos L V, et al. (2016) Unraveling the genetic basis of xylose consumption in engineered *Saccharomyces cerevisiae* strains. *Sci Rep* 6:38676.
39. Nishimura K, Fukagawa T, Takisawa H, Kakimoto T, Kanemaki M (2009) An auxin-based degron system for the rapid depletion of proteins in nonplant cells. *Nat Methods* 6(12):917-922.
40. Van de Velde S, Thevelein J M (2008) Cyclic AMP-protein kinase A and Snf1 signaling mechanisms underlie the superior potency of sucrose for induction of filamentation in *Saccharomyces cerevisiae*. *Eukaryot Cell* 7(2): 286-293.
41. Shively C A, et al. (2015) Large-Scale Analysis of Kinase Signaling in Yeast Pseudohyphal Development Identifies Regulation of Ribonucleoprotein Granules. *PLoS Genetics* 11(10):e1005564.
42. Griffioen G, Thevelein J M (2002) Molecular mechanisms controlling the localisation of protein kinase A. *Curr Genet* 41(4):199-207.
43. Galello F, Moreno S, Rossi S (2014) Interacting proteins of protein kinase A regulatory subunit in *Saccharomyces cerevisiae*. *Journal of Proteomics* 109:261-275.
44. Smith F D, et al. (2017) Local protein kinase A action proceeds through intact holoenzymes. *Science* 356(6344): 1288-1293.
45. Gasch A P (2002) Yeast genomic expression studies using DNA microarrays. *Guide to Yeast Genetics and Molecular and Cell Biology—Part B*, Methods in Enzymology. (Elsevier), pp 393-414.
46. Bolger A M, Lohse M, Usadel B (2014) Trimmomatic: a flexible trimmer for Illumina sequence data. *Bioinformatics* 30(15):2114-2120.
47. McIlwain S J, et al. (2016) Genome sequence and analysis of a stress-tolerant, wild-derived strain of *Saccharomyces cerevisiae* used in biofuels research. *G3* 6(6): 1757-1766.
48. Langmead B (2010) Aligning short sequencing reads with Bowtie. *Curr Protoc Bioinformatics* 17.
49. Anders S, Pyl P T, Huber W (2014) HTSeq—A Python framework to work with high-throughput sequencing data. *Bioinformatics* 31(2):btu638-169.
50. Robinson M, McCarthy D, Smyth G (2010) edgeR: a Bioconductor package for differential expression analysis of digital gene expression data. *Bioinformatics* 26(1):139.
51. Benjamini Y, Hochberg Y (1995) Controlling the false discovery rate: a practical and powerful approach to multiple testing. *Journal of the Royal Statistical Society Series B (Methodological)* 57(1):289-300.
52. Fraley C, Raftery A E (2011) Model-Based Clustering, Discriminant Analysis, and Density Estimation. *J Am Stat Assoc* 97(458):611-631.
53. Saldanha A J (2004) Java Treeview—extensible visualization of microarray data. *Bioinformatics* 20(17):3246-3248.
54. Robinson M D, Grigull J, Mohammad N, Hughes T R (2002) FunSpec: a web-based cluster interpreter for yeast. *BMC Bioinformatics* 3(1):35.
55. Boyle E I, et al. (2004) GO::TermFinder—open source software for accessing Gene Ontology information and finding significantly enriched Gene Ontology terms associated with a list of genes. *Bioinformatics* 20(18):3710-3715.
56. Chasman D, et al. (2014) Pathway connectivity and signaling coordination in the yeast stress-activated signaling network. *Mol Syst Biol* 10(11):759-759.
57. Teixeira M C, et al. (2014) The YEASTRACT database: an upgraded information system for the analysis of gene and genomic transcription regulation in *Saccharomyces cerevisiae*. 42(D1):D161-D166.
58. Bailey T L, Williams N, Misleh C, Li W W (2006) MEME: discovering and analyzing DNA and protein sequence motifs. 34(Web Server issue):W369-73.
59. Gupta S, Stamatoyannopoulos J A, Bailey T L, Noble W (2007) Quantifying similarity between motifs. *Genome Biol* 8(2):R24.
60. Hebert A S, et al. (2014) The one hour yeast proteome. *Mol Cell Proteomics* 13(1):339-347.
61. Cox J, Mann M (2008) MaxQuant enables high peptide identification rates, individualized p.p.b.-range mass accuracies and proteome-wide protein quantification. *Nat Biotechnol* 26(12):1367-1372.
62. Cox J, et al. (2011) Andromeda: a peptide search engine integrated into the MaxQuant environment. *J Proteome Res* 10(4):1794-1805.
63. Wenger C D, Phanstiel D H, Lee M V, Bailey D J, Coon J J (2011) COMPASS: A suite of pre- and post-search proteomics software tools for OMSSA. *Proteomics* 11(6): 1064-1074.
64. Geer L Y, et al. (2004) Open mass spectrometry search algorithm. *J Proteome Res* 3(5):958-964.
65. Schwalbach M S, et al. (2012) Complex Physiology and Compound Stress Responses during Fermentation of Alkali-Pretreated Corn Stover Hydrolysate by an *Escherichia coli* Ethanologen. *Appl Environ Microbiol* 78(9): 3442-3457.
66. Mok J, et al. (2010) Deciphering Protein Kinase Specificity through Large-Scale Analysis of Yeast Phosphorylation Site Motifs. *Sci Signal* 3(109):ra12-ra12.
67. Magtanong L, et al. (2011) Dosage suppression genetic interaction networks enhance functional wiring diagrams of the cell. *Nat Biotechnol* 29(6):505-511.
68. Morawska M, Ulrich H D (2013) An expanded tool kit for the auxin-inducible degron system in budding yeast. *Yeast* 30(9):341-351.
69. Tanaka S, Miyazawa Onami M, Iida T, Araki H (2015) iAID: an improved auxin-inducible degron system for the construction of a "tight" conditional mutant in the budding yeast *Saccharomyces cerevisiae*. *Yeast* 32(8):567-581.
70. Nishimura K, Kanemaki M T (2014) Rapid Depletion of Budding Yeast Proteins via the Fusion of an Auxin-Inducible Degron (AID). *Curr Protoc Cell Biol* 64:20.9.1-16.
71. Crooks G E, Hon G, Chandonia J-M, Brenner S E (2004) WebLogo: a sequence logo generator. *Genome Res* 14(6): 1188-1190.
72. Bailey T L, Gribskov M (1998) Combining evidence using p-values: application to sequence homology searches. *Bioinformatics* 14(1):48-54.
73. Cox J, et al. (2014) Accurate Proteome-wide Label-free Quantification by Delayed Normalization and Maximal Peptide Ratio Extraction, Termed MaxLFQ. *Mol Cell Proteomics* 13 (9): 2513-2526.
74. Taus T, et al. (2011) Universal and confident phosphorylation site localization using phosphoRS. *JProteome Res* 10(12):5354-5362.
75. Sadowski I, et al. (2013) The PhosphoGRID *Saccharomyces cerevisiae* protein phosphorylation site database: version 2.0 update. *Database* 2013(0):bat026-bat026.
76. Chou M F, Schwartz D (2011) Biological sequence motif discovery using motif-x. *Curr Protoc Bioinformatics* Chapter 13:Unit 13.15-24.
77. Schwartz D, Gygi S P (2005) An iterative statistical approach to the identification of protein phosphorylation motifs from large-scale data sets. *Nat Biotechnol* 23(11): 1391-1398.
78. Chatr-aryamontri A, et al. (2017) The BioGRID interaction database: 2017 update. 45(D1):D369-D379.
79. Sharifpoor S, et al. (2011) A quantitative literature-curated gold standard for kinase-substrate pairs. *Genome Biol* 12(4):R39.
80. MacGilvray M E, et al. (2017) Network inference reveals novel connections in pathways regulating growth and defense in the yeast salt response. *bioRxiv:* 176230.
81. Thijs G, et al. (2002) A Gibbs sampling method to detect overrepresented motifs in the upstream regions of coexpressed genes. *J Comput Biol* 9(2):447-464.
82. Heidrich K, et al. (1997) Autophosphorylation-inactivation site of hexokinase 2 in *Saccharomyces cerevisiae*. *Biochemistry* 36(8):1960-1964.
83. Vega M, Riera A, Fernández-Cid A, Herrero P, Moreno F (2016) Hexokinase 2 Is an Intracellular Glucose Sensor of Yeast Cells That Maintains the Structure and Activity of Mig1 Protein Repressor Complex. *J Biol Chem* 291 (14):7267-7285.
84. Ahuatzi D, Riera A, Peláez R, Herrero P, Moreno F (2007) Hxk2 regulates the phosphorylation state of Mig1 and therefore its nucleocytoplasmic distribution. *J Biol Chem* 282(7):4485-4493.
85. Ludin K, Jiang R, Carlson M (1998) Glucose-regulated interaction of a regulatory subunit of protein phosphatase 1 with the Snf1 protein kinase in *Saccharomyces cerevisiae*. *Proc Natl Acad Sci USA* 95(11):6245-6250.
86. Thevelein J M, De Winde J H (1999) Novel sensing mechanisms and targets for the cAMP-protein kinase A pathway in the yeast *Saccharomyces cerevisiae*. *Molecular Microbiology* 33(5):904-918.
87. Gross E, Goldberg D, Levitzki A (1992) Phosphorylation of the *S. cerevisiae* Cdc25 in response to glucose results in its dissociation from Ras. *Nature* 360(6406):762-765.
88. Jian D, Aili Z, Xiaojia B, Huansheng Z, Yun H (2010) Feedback regulation of Ras2 guanine nucleotide exchange factor (Ras2-GEF) activity of Cdc25p by Cdc25p phosphorylation in the yeast *Saccharomyces cerevisiae*. *FEBS Lett* 584(23):4745-4750.
89. Gross A, Winograd S, Marbach I, Levitzki A (1999) The N-terminal half of Cdc25 is essential for processing glucose signaling in *Saccharomyces cerevisiae*. *Biochemistry* 38(40):13252-13262.
90. Jackson S P, Downs J A, Lowndes N F (2000) A role for *Saccharomyces cerevisiae* histone $H_2A$ in DNA repair. *Nature* 408(6815):1001-1004.
91. Comparison of xylose fermentation by two high-performance engineered strains of *Saccharomyces cerevisiae* (2016) Comparison of xylose fermentation by two high-performance engineered strains of *Saccharomyces cerevisiae*. 9:53.
92. Lee S-M, Jellison T, Alper H S (2014) Systematic and evolutionary engineering of a xylose isomerase-based pathway in *Saccharomyces cerevisiae* for efficient conversion yields. *Biotechnol Biofuels* 7(1):122.
93. Kim S R, et al. (2013) *Rational and Evolutionary Engineering Approaches* Uncover a Small Set of Genetic Changes Efficient for Rapid Xylose Fermentation in *Saccharomyces cerevisiae*. *PLoS ONE* 8(2):e57048.
94. Zhou H, Cheng J-S, Wang B L, Fink G R, Stephanopoulos G (2012) Xylose isomerase overexpression along with engineering of the pentose phosphate pathway and evolutionary engineering enable rapid xylose utilization and ethanol production by *Saccharomyces cerevisiae*. *Metab Eng* 14(6):611-622.
95. Cadete R M, et al. (2016) Exploring xylose metabolism in *Spathaspora* species: XYL1.2 from *Spathaspora passalidarum* as the key for efficient anaerobic xylose fermentation in metabolic engineered *Saccharomyces cerevisiae*. *Biotechnol Biofuels* 9(1):167.
96. Runquist D, Hahn-Hägerdal B, Bettiga M (2010) Increased ethanol productivity in xylose-utilizing *Saccharomyces cerevisiae* via a randomly mutagenized xylose reductase. *Appl Environ Microbiol* 76(23):7796-7802.

97. Drgon T, Sabová L, Nelson N, Kolarov J (1991) ADP/ATP translocator is essential only for anaerobic growth of yeast *Saccharomyces cerevisiae*. *FEBS Lett* 289(2):159-162.
98. Abramova N, Sertil O, Mehta S, Lowry C V (2001) Reciprocal regulation of anaerobic and aerobic cell wall mannoprotein gene expression in *Saccharomyces cerevisiae*. *J Bacteriol* 183(9):2881-2887.
99. Camarasa C, Faucet V, Dequin S (2007) Role in anaerobiosis of the isoenzymes for *Saccharomyces cerevisiae* fumarate reductase encoded by OSM1 and FRDS1. *Yeast* 24(5):391-401.
100. Rachidi N, Martinez M J, Barre P, Blondin B (2002) *Saccharomyces cerevisiae* PAU genes are induced by anaerobiosis. *Molecular Microbiology* 35(6):1421-1430.
101. Linde ter J J, et al. (1999) Genome-wide transcriptional analysis of aerobic and anaerobic chemostat cultures of *Saccharomyces cerevisiae*. *J Bacteriol* 181(24):7409-7413.
102. Wilcox L J (2002) Transcriptional Profiling Identifies Two Members of the ATP-binding Cassette Transporter Superfamily Required for Sterol Uptake in Yeast. *J Biol Chem* 277(36):32466-32472.
103. Sertil O, Cohen B D, Davies K J, Lowry C V (1997) The DAN1 gene of *S. cerevisiae* is regulated in parallel with the hypoxic genes, but by a different mechanism. *Gene* 192(2):199-205.
104. Skoneczny M, Rytka J (2000) Oxygen and haem regulate the synthesis of peroxisomal proteins: catalase A, acyl-CoA oxidase and Pex1p in the yeast *Saccharomyces cerevisiae*; the regulation of these proteins by oxygen is not mediated by haem. *Biochemical Journal* 350(1):313-319.
105. Luo Z, van Vuuren H J J (2009) Functional analyses of PAU genes in *Saccharomyces cerevisiae*. *Microbiology* 155(12):4036-4049.

What is claimed is:

1. A recombinant yeast comprising an expression cassette comprising a recombinant nucleic acid molecule comprising the nucleotide sequence of SEQ ID NO:1 encoding functional Azoospermia Factor 1 (AZF1), and a heterologous inducible promoter operably linked to the nucleotide sequence, wherein the recombinant yeast is capable of anaerobic xylose fermentation, wherein the recombinant yeast does not express ISU1, HOG1, GRE3, or IRA2.

2. The recombinant yeast of claim 1, wherein the recombinant yeast is of the genus *Saccharomyces*.

3. The recombinant yeast of claim 1, wherein the recombinant yeast is of the genus *Saccharomyces cerevisiae*.

4. The recombinant yeast of claim 1, wherein the isolated nucleic acid molecule is stably maintained in the recombinant yeast.

5. The recombinant yeast of claim 1, wherein the recombinant isolated nucleic acid molecule is integrated into a chromosome of the recombinant yeast.

6. A recombinant *Saccharomyces cerevisiae* strain, comprising a recombinant nucleic acid molecule comprising SEQ ID NO:1 encoding functional Azoospermia Factor 1 (AZF1) operably linked to a heterologous promoter, wherein the recombinant *Saccharomyces cerevisiae* strain is engineered for anaerobic xylose fermentation, wherein the strain does not express ISU1, HOG1, GRE3, or IRA2.

7. The recombinant *Saccharomyces cerevisiae* strain of claim 6, further comprising a heterologous sequence for extrachromosomal stable maintenance.

8. A method for producing ethanol by anaerobic fermentation of xylose in yeast, comprising: (a) culturing the recombinant yeast of claim 1 under ethanol producing conditions in the presence of xylose; and (b) isolating ethanol produced by the recombinant yeast.

9. A method for producing ethanol by anaerobic fermentation of xylose in *Saccharomyces cerevisiae*, comprising: (a) culturing the recombinant *Saccharomyces cerevisiae* yeast of claim 6 under ethanol-producing conditions, and (b) isolating ethanol produced by the recombinant *Saccharomyces cerevisiae*, wherein the nucleic acid molecule comprises an operably linked heterologous promoter.

10. The method of claim 9, wherein the recombinant nucleic acid molecule is integrated into a heterologous sequence for extrachromosomal stable maintenance.

11. The method of claim 9, wherein the recombinant nucleic acid molecule is integrated into a chromosome.

12. The method of claim 9, wherein the recombinant nucleic acid molecule encoding AZF1 is SEQ ID NO: 1.

* * * * *